(12) United States Patent
Hansen et al.

(10) Patent No.: US 8,432,550 B2
(45) Date of Patent: *Apr. 30, 2013

(54) METHOD AND A SYSTEM FOR DETERMINATION OF PARTICLES IN A LIQUID SAMPLE

(75) Inventors: Frans Ejner Ravn Hansen, Frederiksberg C (DK); Martin Glensbjerg, Brønshøj (DK); Börkur Arnvidarson, Reykjavik (IS); Jesper Myron Jeppesen, Brønshøj (DK)

(73) Assignee: ChemoMetec A/S, Allerod (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,010

(22) Filed: Mar. 28, 2012

(65) Prior Publication Data

US 2012/0223260 A1    Sep. 6, 2012

Related U.S. Application Data

(60) Continuation of application No. 12/062,298, filed on Apr. 3, 2008, which is a division of application No. 11/414,839, filed on May 1, 2006, now Pat. No. 8,125,643, which is a continuation of application No. 11/130,717, filed on May 17, 2005, now Pat. No. 7,068,365, which is a continuation of application No. 10/727,832, filed on Dec. 4, 2003, now Pat. No. 6,919,960, which is a continuation of application No. 09/403,958, filed as application No. PCT/DK98/00175 on May 5, 1998, now Pat. No. 6,710,879.

(30) Foreign Application Priority Data

May 5, 1997   (DK) ........................................ 0509/97
Dec. 9, 1997   (DK) ........................................ 1431/97

(51) Int. Cl.
*G01N 21/00* (2006.01)
*G01N 33/48* (2006.01)

(52) U.S. Cl.
USPC ............................................ 356/436; 356/39

(58) Field of Classification Search .................. None
See application file for complete search history.

(56) References Cited

U.S. PATENT DOCUMENTS 3,679,365 A   7/1972   Wrightman et al.
3,705,755 A   12/1972  Baer (Continued)

FOREIGN PATENT DOCUMENTS

DE   0 342 501   5/1989
DE   0 459 371   5/1991

(Continued)

OTHER PUBLICATIONS

Parthenis et al. "Blood analysis using black and white digital images." *J Biomed. Eng.* vol. 14. 1992. pp. 287-292.

(Continued)

*Primary Examiner* — Gregory J Toatley
*Assistant Examiner* — Amanda Merlino
(74) *Attorney, Agent, or Firm* — Merchant & Gould P.C.

(57) ABSTRACT

A method for the assessment of quantity and quality parameters of biological particles in a liquid analyte material. The method comprises applying a volume of a liquid sample to an exposing domain from which exposing domain electromagnetic signals from the sample in the domain can pass to the exterior, and exposing, onto an array of active detection elements such as CCD-elements, a spatial representation of electromagnetic signals having passed from the domain, the representation being detectable as an intensity by individual active detection elements, under conditions permitting processing of the intensities detected by the array of detection elements during the exposure in such a manner that representations of electromagnetic signals from the biological particles are identified as distinct from representations of electromagnetic signals from background signals.

30 Claims, 17 Drawing Sheets

U.S. PATENT DOCUMENTS

| | | | |
|---|---|---|---|
| 4,075,462 A | 2/1978 | Rowe | |
| 4,084,905 A | 4/1978 | Schreiber et al. | |
| 4,181,853 A | 1/1980 | Abu-Shumays et al. | |
| 4,243,318 A | 1/1981 | Stöhr | |
| 4,295,199 A | 10/1981 | Curry et al. | |
| 4,550,417 A | 10/1985 | Nunogaki et al. | |
| 4,601,551 A | 7/1986 | Pettingell et al. | |
| 4,643,877 A | 2/1987 | Opitz et al. | |
| 4,744,667 A | 5/1988 | Fay et al. | |
| 4,768,390 A | 9/1988 | Baker et al. | |
| 4,804,850 A | 2/1989 | Norrish et al. | |
| 4,896,967 A | 1/1990 | Douglas-Hamilton et al. | |
| 4,900,685 A | 2/1990 | Smith, III | |
| 5,081,350 A | 1/1992 | Iwasaki et al. | |
| 5,093,866 A | 3/1992 | Douglas-Hamilton et al. | |
| 5,104,221 A | 4/1992 | Bott et al. | |
| 5,106,187 A | 4/1992 | Bezanson | |
| 5,147,806 A | 9/1992 | Kamin et al. | |
| 5,196,709 A | 3/1993 | Berndt et al. | |
| 5,291,422 A | 3/1994 | Esztergar | |
| 5,306,467 A | 4/1994 | Douglas-Hamilton et al. | |
| 5,351,118 A | 9/1994 | Spinell | |
| 5,428,451 A | 6/1995 | Lea et al. | |
| 5,457,526 A | 10/1995 | Kosaka | |
| 5,473,437 A | 12/1995 | Blumenfeld et al. | |
| 5,494,800 A | 2/1996 | Smith, III | |
| 5,594,544 A | 1/1997 | Horiuchi et al. | |
| 5,663,057 A | 9/1997 | Drocourt et al. | |
| 5,713,364 A | 2/1998 | DeBaryshe et al. | |
| 5,751,839 A | 5/1998 | Drocourt et al. | |
| 5,796,480 A | 8/1998 | Igushi | |
| 5,798,222 A | 8/1998 | Goix | |
| 5,828,716 A | 10/1998 | Bisconte de Saint Julien | |
| 6,162,931 A | 12/2000 | Gee et al. | |
| 6,710,879 B1 | 3/2004 | Hansen et al. | |
| 6,731,100 B1 | 5/2004 | Hansen et al. | |
| 6,919,960 B2 | 7/2005 | Hansen et al. | |
| 7,068,365 B2 | 6/2006 | Hansen et al. | |

FOREIGN PATENT DOCUMENTS

| | | |
|---|---|---|
| EP | 0 045 971 | 2/1982 |
| EP | 0 342 501 | 5/1989 |
| EP | 0 459 371 | 5/1991 |
| EP | 0 468 100 | 1/1992 |
| EP | 0 556 971 | 2/1993 |
| EP | 0 543 514 | 5/1993 |
| EP | 0 556 971 | 8/1993 |
| EP | 0 634 640 | 5/1994 |
| EP | 0 683 395 | 5/1995 |
| EP | 0 681 177 | 11/1995 |
| EP | 0 753 732 | 1/1997 |
| GB | 2 001 434 | 7/1978 |
| GB | 2 152 660 | 11/1984 |
| JP | 56-72846 | 6/1981 |
| JP | 62274241 | 11/1987 |
| JP | 2-6729 | 1/1990 |
| JP | 4125609 | 4/1992 |
| JP | 4-188061 | 7/1992 |
| JP | 6-221986 | 8/1994 |
| JP | 8-54333 | 2/1996 |
| JP | 8-247921 | 9/1996 |
| JP | 09033423 | 2/1997 |
| NZ | 226895 | 7/1990 |
| RU | 2 060 499 | 9/1994 |
| WO | WO 90/13016 | 11/1990 |
| WO | WO 91/09297 | 6/1991 |
| WO | WO 91/09308 | 6/1991 |
| WO | WO 91/15826 | 10/1991 |
| WO | WO 92/02632 | 2/1992 |
| WO | WO 96/31764 | 10/1996 |
| WO | WO 97/07390 | 2/1997 |
| WO | WO 97/15229 | 5/1997 |
| WO | WO 98/50577 | 11/1998 |

OTHER PUBLICATIONS

Notice of Opposition filed in European Application No. 08101755.0 dated Apr. 18, 2012.

Copy of Opposition filed in European Application No. 08101755.0 dated Mar. 22, 2012.

Wittrup et al., 'Fluorescence Array Detector for Large-Field Quantitative Fluorescence Cytometry,' *Cytometry*, vol. 16, pp. 206-213,— (1994).

Chen et al, "Monitoring of red blood cell aggregability in a flow-chamber by computerized image analysis," *Clinical Hemororheology*, vol. 14, No. 4, pp. 491-508 (1994).

Chen et al, "Red blood cell aggregability is enhanced by physiological levels of hydrostatic pressure," *Biochimica et Biophysica Acta*, vol. 1192, pp. 247-252 (1994).

Chen et al, "Monitoring of erythrocyte aggregate morpology under flow by computerized image analysis," *Biorheology*, vol. 32, No. 4, pp. 487-496 (1995).

Hader et al. "Novel Method to Determine Vertical Distributions of Phytoplankton in Marine Water Columns." *Environmental and Experimental Botany*. vol. 35, No. 4 (1995), pp. 547-555.

Hader et al. "Simultaneous tracking of flagellates in real time by image analysis." *Journal of Mathematical Biology*. vol. 30 (1991), pp. 63-72.

Hader et al. "Versatile digital image analysis by microcomputer to count microorganisms." *EDV in Medizin und Biologie*. vol. 18 (2-3)(1987), pp. 37-42.

Richter et al. "Vertical Migration and Motility Responses in Three Marine Phytoplankton Species Exposed to Solar Radiation." *Photochemistry and Photobiology*. vol. 83 (2007), pp. 810-817.

Derwent Info No. XP002900128.

METHOD AND A SYSTEM FOR DETERMINATION OF PARTICLES IN A LIQUID SAMPLE

This application is a Continuation of application Ser. No. 12/062,298, filed 3 Apr. 2008, which is a Divisional of application Ser. No. 11/414,839, filed 1 May 2006, now issued as U.S. Pat. No. 8,125,643, which is a Continuation of application Ser. No. 11/130,717 filed 17 May 2005, now issued as U.S. Pat. No. 7,068,365, which is a Continuation of application Ser. No. 10/727,832 filed 4 Dec. 2003, now issued as U.S. Pat. No. 6,919,960, which is a Continuation of application Ser. No. 09/403,958, filed 1 Nov. 1999, now issued as U.S. Pat. No. 6,710,879, which is a National Stage of Application PCT/DK98/00175 filed 5 May 1998, which claims benefit of Serial No. 1431/97, filed 9 Dec. 1997 in Denmark, and which also claims benefit of Serial No. 0509/97, filed 5 May 1997, and which applications are incorporated herein by reference. A claim of priority to all, to the extent appropriate, is made.

FIELD OF THE INVENTION

This invention relates to a method and a system for the determination or assessment of at least one quantity parameter and/or at least one quality parameter of biological particles in a liquid analyte material. As an important quantity parameter can be mentioned the number of biological particles in a volume of the analyte material, such as, e.g., the number of somatic cells in milk or blood, or the number of bacteria in a urine sample. Another important example of a quantity parameter whether or not an analyte, such as a liquid analyte derived by selective enrichment of a food sample, contains a particular bacterial species, such as Salmonella typhimurium. As examples of quality parameters may be mentioned morphological properties of biological particles such as size and/or shape, or identification of one or more types of biological particles in a mixture of more than one types of biological particles.

DESCRIPTION OF RELATED ART

Determinations or assessments of the above types have been performed by various methods. One of these methods is flow cytometry; instrument for performing flow cytometry are available, e.g., from Becton, Dickinson and Company, Franklin Lakes. Flow cytometry requires rather elaborate and high cost equipment, partly because of the high accuracy of flow rate necessary to give reliable results, and partly because the high sensitivity needed to detect the weak signals from the particles in question during the relative short period of time the particle is present in the detector.

Another known method for the determination of somatic cells or bacteria in milk is based on the detection of signals from particles which are dispersed on the rim of a polished rotating disc, one such instrument available from Foss Electric, Hillerød. The accuracy in the assessment of the number of particles using this method is dependent on the physical shape of the thin film of sample dispersed on the disk, and high sensitivity is needed to detect the weak signals from the particles in question in the course of the relative short period of time the particle is present in the detector.

One known method for the determination of somatic cells in milk based on spreading a film of milk onto a ribbon-like film which is then analysed by the means of a microscope, cf. European patent 0 683 395. This method appears to requires a complex mechanical solution in order to work reliably.

Due to the relative high complexity and cost the instruments used today, most of the assessments of biological particles are carried out on in a laboratory where skilled operators operate the instruments.

DESCRIPTION OF THE INVENTION

The present invention offers substantial simplification of the assessment of quantity parameters and/or quality parameters of biological particles in liquid analyte materials and therefore makes it possible for operators without any particular skill in this fields of technique to perform the assessment. In particular, the invention makes it possible to perform the assessment in the clinic or on the farm where the sample is taken, thus making the results of the assessment available for the user substantially immediately after the sample material has been collected.

The physical dimension of an instrument based on the present invention is also such that the instrument will be well suited for transport, thus making it possible for medical doctors or veterinarians to transport the instrument to or on a location where the analysis is needed. The principle of measurement of the present invention provides a major improvement in the assessment of biological particles, such as DNA containing particles, e.g. somatic cells or bacteria, or red blood cells, in a liquid analyte material, such as milk, blood or urine, compared to the methods hitherto used for this purpose.

This invention extends the capabilities of prior devices and methods to enable more simple and reliable assessment of biological particles in liquid analyte material. The properties which can be assessed are the number of particles in a volume of the analyte material, any morphological properties such as size or area of the particles, or the identification of the type of particle being analysed. In particular it is possible to assess more than one of these properties simultaneously.

At the same time, this invention allows these analysis to be carried out with the use of considerably smaller amounts of chemicals than normally are required to do these analysis. These chemicals are often considered hazardous, either to humans and other living organism or to the environment. Furthermore, this invention presents a solution which minimises the exposure of any hazardous sample or chemicals used for the analysis by either allowing the analysis to be performed in a closed flow system or by the use of a sealed and disposable sample compartment which contains all sample material and chemicals used for the assessment and allows save transport of the sample and any chemicals.

The high cost as well as the mechanical complexity of the instruments hitherto used for the routine assessment of the number of particles in liquid analyte material has made the instruments impractical to use routinely under condition such as are normally present on dairy farms, on milk dairies, or in medical or veterinary clinics. Such analyses are of great interest, for instance, a dairy farmer can monitor the somatic cell count or bacterial count of an individual animal in order to follow the course of clinical or subclinical mastitis or infection, and to control the cell count of the bulk milk delivered to the dairy, thereby minimising the use of antibiotics and preventing the economical penalty which is often a consequence when the cell count of bulk milk exceeds predefined limits.

Medical clinics are often in the need to know the count of one or more particles in blood, urine or other biological fluids such as somatic cells or bacteria, but since such analysis are usually carried out in a central laboratory, this often delays the response of such analysis due to transport of the sample.

It was found that this invention allows the analysis of various types of biological particles, such as DNA-containing particles, red blood cells, blood platelets, yeast cells, bacteria cells, lipid globules, protein micelles, dust particles, or polymer particles, these particles normally found in liquid biological analyte material such as milk, blood, urine, faces, salvia, inflammation, of either human or animal origin, or samples originating from the petrochemical industry, the pharmaceutical industry, feed industry, food industry or the like. The method is also well suited for the detection of any other biological particle or fragments thereof, such particle being a part or a fraction of living matter and displaying properties which can be detected with the detection of electromagnetic radiation.

This invention is particularly suited for the assessment of the number of somatic cells in milk from human, cow, goat, sheep, buffalo or other animal. In particular, this invention is suited for the assessment of the number of somatic cells in milk during milking by integrating the system with the milking equipment, either in-line where the measurement is taken substantially from the milking system and analysed by an instrument which is operated synchronised with the milking, or at-line where the sample is taken before, during or after milking and measured on an instrument in manual operation, in particular it is well suited to obtain an estimate of the number of somatic cells when the purpose of the analysis is to control the number of somatic cells in the bulk of milk delivered to the dairy, for instance by directing any milk which is found to have high cell count to a separate container or outlet.

Methods according to the invention are suited for the on-line or at-line assessment of the number of somatic cells in milk when the purpose is to establish information about the health status of animals, such as cows, goats, sheep or buffaloes, especially in connection with clinical or sub-clinical mastitis.

The method according to the invention is suited for the assessment of the number of somatic cells in milk when the objective of the analysis it to generate information used in a heard improvement scheme, or when the objective of the analysis is to obtain a quality parameter used in a payment scheme. These analyses are normally carried out on a central laboratory, by the use of complex instruments.

According to the invention, an array of detection elements can be utilised in combination with appropriate electronic components, to accomplish the assessment of biological particles in a analyte material by placing a portion of the analyte material in a sample compartment, the sample compartment in many embodiments of this invention being two windows of glass, or other transparent material, separated by a spacer with inlet and outlet which allows the sample to be replaced between measurements; in one embodiment, the sample compartment is a tube, substantially circular, or substantially elliptical in profile. The presence of a particle will normally cause the signal from a detection element to deviate from a normal level, e.g. a base-line level, either towards higher signal intensity or toward lower signal intensity, but for the sake of clarity in the following it will be assumed that such deviation is toward higher signal intensity.

The present invention is based on the arrangement of the sample in such a manner that it extends over a "window" of a substantial area and detection of signals from the samples in the form of an "image" on an array of detection elements, the array of detection elements comprising individual elements each of which is capable of sensing signals from a part of the sample window area, the array as a whole being capable of sensing signals from substantially all of the sample window area, or at least a well defined part of the sample window area.

As will appear from the following, the arrangement of the sample and the detection elements in this way will allow the determination of the number of the particles per volume in a much more simple and economic manner, while retaining a high accuracy of the determination. Also, as will be explained in the following, the use of an array of detection elements "observing" an exposed area of the sample makes it possible to use quite simple means for generating signals from the sample and quite simple and sensitive detection means.

Thus, an aspect of the invention can be expressed as a method for the assessment of the number of particles in a volume of liquid sample material, the method comprising arranging a sample of the liquid sample material in a sample compartment having a wall defining an exposing area, the wall allowing signals from the sample to pass through the wall and to be exposed to the exterior, forming an image of signals from the sample in the sample compartment on an array of detection elements, processing the image on said array of detection elements in such a manner that signals from said particles are identified as distinct from the sample background, and, based on the signals from said particles identified assessing the number of particles in a volume of said liquid sample material.

Expressed in another and more general way, this aspect of the invention relates to a method for the assessment of at least one quantity parameter and/or at least one quality parameter of biological particles in a liquid analyte material, comprising applying a volume of a liquid sample representing the analyte material, or particles isolated from a volume of liquid sample representing the analyte material, to an exposing domain from which exposing domain electromagnetic signals from the sample in the domain can pass to the exterior, exposing, onto an array of active detection elements, an at least one-dimensional spatial representation of electromagnetic signals having passed from the domain, the representation being one which is detectable as an intensity by individual active detection elements, under conditions which will permit processing of the intensities detected by the array of detection elements during the exposure in such a manner that representations of electromagnetic signals from the biological particles are identified as distinct from representations of electromagnetic signals from background signals, the size of the volume of the liquid sample being sufficiently large to permit the assessment of the at least one quantity parameter or the at least one quality parameter to fulfil a predetermined requirement to the statistical quality of the assessment based on substantially one exposure, processing the intensities detected by the detection elements in such a manner that signals from the biological particles are identified as distinct from background signals, and correlating the results of the processing to the at least one quantity parameter and/or the at least one quality parameter of the liquid analyte material.

The liquid sample representing the analyte material may be a liquid sample consisting of the liquid analyte material per se (optionally and often preferably with added chemical substances facilitating the assessment, such as will be explained in the following), or it may be a sample which has been derived from the liquid analyte material by dilution, concentration, extraction, or other modification. In this connection it is, of course, normally essential that there is an unambiguous correlation between the volume of the liquid sample representing the liquid analyte material and the volume of the liquid analyte material in question, so that the necessary correlation to a concentration in the liquid analyte can be established. As mentioned above, the liquid analyte material may in itself be a derivative of another material the properties of which are to be analysed using the method of the invention;

thus, e.g., the liquid analyte may be a liquid enrichment culture derived from a food product, e.g. poultry.

Alternatively, particles isolated from a volume of a liquid sample representing the liquid analyte material may be the material from which the exposure onto the array of detection elements is made. This is the case, e.g., when a liquid sample representing the liquid analyte material has been filtered through a filter material, and the filter material with the retained particles, often after addition of chemicals facilitating the assessment, cf. below, such chemicals having been added before or normally after the filtration, is arranged in the domain from which the exposure is made, normally a sample compartment suited for housing the filter.

As mentioned above, the exposure of the electromagnetic signals having passed from the domain onto the array of detection elements will normally correspond to forming an "image" of the domain (such as an exposing area of a wall part of a sample compartment) on a two-dimensional array of detection elements, but it is also possible to use a one-dimensional spatial representation, obtained by suitable optical means, in which case the array of detection elements need not be more than one-dimensional, such as a linear array of detection elements. In special embodiments, a linear array of detection elements can also be used for receiving a two-dimensional image of electromagnetic radiation, provided the area of each element is sufficient to receive signals from a sufficient volume to allow the quality requirements to the determination.

The intensity detected by the array of detection elements may be a charge built up due to the electromagnetic radiation, or it may be, e.g., the intensity of a current passing through the individual element as a result of the electromagnetic radiation.

The conditions of the exposure with respect to the various parameters involved, such as will be explained in greater detail below, are adapted so that the intensities detected by the array of detection elements can be processed, using suitable processing means, typically image processing means and methods, in such a manner that the intensities which have been detected as representations of electromagnetic signals from the biological particles are identified as distinct from representations of background signals.

The size of the volume of the liquid sample on which measurement is made, or from which the particles are isolated, should be sufficiently large to permit the assessment of the at least one quantity parameter or the at least one quality parameter to fulfil a predetermined requirement to the statistical quality of the assessment based on substantially one exposure. As will be explained in the following, it is a characteristic feature of the present invention that it permits the gathering of sufficient information in one exposure to allow a high statistical quality in spite of the fact that the assessment can be performed in an extremely simple manner. One reason for this is that the method of the invention is normally performed using much smaller enlargements of the image projected onto the array of detection elements than has hitherto been considered possible, and in some cases even reductions, in contrast to enlargements. For a number of applications, the degree of enlargement is just around 1:1, in contrast to most automated microscopy methods which use larger enlargements and several observations. In connection with the present invention, the term "substantially one exposure" is to be understood as one exposure or in some cases just a few exposures such as two, three or four exposures, but the by far preferred embodiment it so use just one exposure, such as is made possible by the invention. The exposure may, under certain circumstances, be performed as a number of sub-exposures before the intensity detected by the array elements is processed, but this is normally not necessary or preferred.

The formation of an image of the sample on the array of detection elements may be performed by arranging the array of detection elements in close contact or substantially in close contact with the exterior of the exposing wall of the sample compartment, or by using an image-forming means, such as a lens comprising one or several elements, arranged in the light path between the exposing wall of the sample compartment and the array of detection elements.

The wall of the sample compartment defining an exposing area may be a flat or curved wall.

The sample in the sample compartment can be replaced by the means of a flow system, which is driven by a pump or a pressurised gas, preferably air. In many embodiments of the present invention the flow in said flow system is controlled by one or more valves which can adjust the flow speed of the sample.

In many preferred embodiments of the present invention the wall of the sample compartment is a plane wall, and the array of detection elements is an array extending in a plane parallel to the plane of the wall. However, dependent on the manner in which the image of the sample is formed on the array of detection elements, the configuration of each of the exposing wall and the array may be designed in many different ways, such as where both the exposing wall and the array are configured as sections of a circular cylinder, such as where the exposing wall is convex and the array is concave with substantially the same radius, whereby they can easily be brought in contact or in substantial contact with each other, or where both the exposing wall and the detection array are concave, and a lens is used for formation of the image of the sample on the array. Many other configurations are, of course possible, such as where both the exposing wall and the array are sections of spheres, etc.

The sample compartment may be a chamber which can easily be removed from the instrument when a new sample or sample material is to be measured. Such removable sample compartment is preferably used for a limited number of measurements and preferably only one. Apart from allowing a more simple mechanical construction of an instrument with the absence of any flow system, one advantage of such removable sample compartment is that it can contain the sample in a closed container before, during and after analysis, thus allowing more safe handling of hazardous material. In many embodiments of the present invention such removable sample compartment can, prior to the introduction of any sample material, contain one or more component or device used for chemical or physical modification of the sample prior to analysis.

Electronical devices or a computer equipped with suited software can be used to condition a signal which originates from any detection element used, preferably in such a way as to make the quantification of the signal from any detection element more reliable or less time consuming, for instance by converting one type of signal to another signal suited for processing, and/or by providing means for the amplification of the signal. Often it is preferred that the signal from any detection element is adjusted for any bias, and/or for any variation in sensitivity which might be present in the signals, this adjustment preferably being performed by taking into account information from neighbouring detection elements, or by using similar information from a previous measurement. Another useful property of such signal conditioning is the conversion of a substantially analogue signal to a digitised value which is better suited for further processing using a digital data processing system; such digitalisation could be a threshold-like activation of two or more output lines in such a way that the input level of any signal would cause a change the status of these output lines, preferably in such a way that the level of the input signal could be estimated. A preferred method of digitalisation is one which allows the level of the input signal to be converted to a number according to the binary number system.

It is often preferred that the digital representation of the level of any input signal produces a substantially linear function, and in many preferred embodiments of this invention it is preferred that the digital representation produces a substantially non-linear function, for instance a logarithmic function, such non-linear function being preferred when the dynamic range of the input level is high.

In some implementations of this invention, it is preferred to use a one-dimensional array of detection elements, preferably included in one chip, the identification of a particle present in the sample which is measured being done by comparing the level of signal from each detection element with a predefined level, or preferably to a level which is estimate on the basis of the signals from neighbouring detection elements, preferably on the basis of the signals from previous measurements, and if a signal is found to be above this discriminating level it is assumed that a particle was present, and a counter is incremented accordingly. Furthermore, it is possible to detect the presence of two particles measured at once for instance by comparing the intensity of a signal to a known or determined limits in such a way that signals above such limit indicate the presence of two particles. More than one such limit can be used to identify any situation where three, four or more particles are present, or an empirical or theoretical relationship can be constructed between the total number of particles present, the possibilities of signals from two or more particles being detected simultaneously by a detection element.

As mentioned above, it is often preferred that an optical system is used to focus any signal from the sample onto the detection elements, and in some cases, it is preferred that such focusing produces an image of a particle with an average size which is of about the same size as the detection elements used, and in certain cases preferably smaller, such that the image of the entire particle is substantially within the boundaries of the detection element.

In other embodiments of this invention, similar to the one described above using a one dimensional array of detection elements or a two-dimensional array of detection elements, it is preferred that an optical system is used to focus any signal from the sample onto the detection elements in such a way as to produce an image which is of the same size as the detection elements used, or in some cases preferably greater, the method being used to identify the presence of a particle taking into account also the extension of the particle in the dimension along the row of detection elements as well as the height of the measured signal from each detection element. Such embodiment of this invention allows the estimation of some morphological properties of the particles which are measured, such as the size. Also under those conditions it is possible to detect the presence of two ore more particles which are focused on substantially the same detection elements, for instance by classifying the signal intensity.

It was surprisingly found that a one dimensional array of detection elements, where the width of the array of detection elements was considerably greater than the height of each detection element, one commercially available from Hamamatzu (S3902-128Q), could be excellently used for the assessment of the number of particles and thus enabling the detection of signals from a greater volume of the sample in each scanning of the detection elements. Furthermore, it was discovered that the use of even a focusing device which distorts the dimensions of the image, relative to the original, in such a way that for instance the image of a circle has a shape which is similar to an ellipse, also gave similar advantage as the use of detection elements with great height, and further it was found that with a combination of the above-mentioned detection elements and a distorting focusing device it was possible to obtain a useful assessment on a large detection volume.

The use of a series of one dimensional arrays of detection elements, preferably incorporated in a single chip, is often found to be useful in the assessment of biological particles present in a sample, one commercially available charge coupled device (CCD) is available from Sony (ICX 045 BL). Another array of detection elements suited for many embodiments of this invention is an image sensor based on CMOS technology which makes detection possible with the use of limited electrical effect, as well as offering on-chip integration with other CMOS based technologies such as signal condition and signal processing, one such has been demonstrated by Toshiba comprising 1318×1030 elements each about 5.6 µm×5.6 µm in size using only 30 mW effect in use.

The assessment of biological particles in a sample can be performed by treating each line of such two dimensional array of detection elements in substantially the same manner as an array of one dimensional detection elements.

Some embodiments of this invention allow the simulation of high detection elements by the electronical or computational addition of information from two or more lines of detection elements into one array of information which is thereafter treated in the substantially the same manner as a single one dimensional array of detection elements, thus allowing substantially simpler and less time consuming interpretation of the measured information.

In some embodiments of this invention the assessment of the number of particles in a first line of detection elements is based on any results, such as position and/or intensities observed in a second line of detection elements already being processed, thus allowing the correction of signals which extend across two or more lines of detection elements.

The inclusion of a focusing device for the focusing of a signal from the sample onto the detection elements in such a manner as to maximise the collection angle, the collection angle being defined as the full plane angle within which a signal is detected, has in many situations been found to give improved conditions for an assessment. Surprisingly it was found that such a wide collection angle, even to the extent that the objective used in the focusing distorted the aspect ratio of the image of any particle differently across the plane in which the detection elements were placed, or produced variation in the focusing across the sample being analysed, or reduction of the focusing quality, could be used in the assessment of the number of particles.

It is possible to make the assessment of biological particles in a sample by using a calculation mean, preferably a digital computer, one commercially available from Analogue Devices (ADSP 2101), equipped with storage capacity which can only store information in amount substantially equivalent to a small fraction of the total number of detection elements, the assessment of the number of objects then being based on substantially real time processing of data, preferably in such a way that the measured information from each detection element, or a line of detection elements, or two or more lines of detection elements, is used for the assessment, substantially without any delay, such as a delay which would otherwise be caused by storing the measured information.

However, it is often preferred to store substantially all measured information by the use of a first calculation mean, preferably a digital computer, before the processing of the information by a second calculation mean, preferably a digital computer, and thus allowing the measured information to be processed at substantially the same rate it is obtained, but with a substantial time delay between the measurement of any information and the processing of the same information; preferably, this is accomplished by using only one calculating mean, preferably a digital computer, equipped with enough resources to accomplish the task.

When using a sample compartment used for the analysis of more than one sample material, for instance when the sample is introduced by means of a flow system, it is often found that one or more of the particles of interest, or fractions of particles, adhere to the sample compartment in such a way that the flow used to replace the sample material is not capable of removing said adhering particles. Thus if such adhering particles are situated in a place which is exposed to the sensing device, it will be included in two or more observation although the sample has been substantially replaced between observations. In many embodiments of the present invention the influence of said adhering particles on the observation can be substantially eliminated by combining two observations in such a way that the result from a first observation is adjusted by the result from a second observation, said second observation being one of many observations taken prior to said first observation or a combination of more than one of many observations taken prior to said first observation, preferably an observation taken substantially immediately prior to said first observation, said adjustment being a simple subtraction of said second observation from said first observation. The result of said adjustment then contains information where any objects present in said first observation have positive intensity, and any object present in said second observation has negative intensity and any object present in both first and second observation have substantially zero intensity. The task of any method used for the assessment of the number of objects or the determination of any morphological properties of an object is then to only treat those intensities which have substantially positive values. In a similar way it is possible to analyse the results of two or more observation taken from different samples from the same sample material by combining those observations as described above and subsequently to analyse both the positive and negative signals, for instance by treating all signals as being positive. In this way it possible to analyse 2, 4, 6, 8 or more observations simultaneously for instance in situations where the effort of analysing an observation is greater than the effort of making an observation.

This invention allows the sample material to be a substantially aqueous solution, or substantially organic solution, or a mixture of two or more immiscible phases, some of which can be liquid, some of which can be solid and some of which can be a suspension, into which the particles of interest are suspended. In many preferred embodiments of this invention the sample material to by analysed has been modified or its chemical or physical properties substantially changed compared to the analyte material by either the addition of, or the removal of one or more components, or by introducing the sample to one or more chemical, mechanical or physical treatments prior to analysis. Preferably the effect of any such alteration or modification is the enhancement of any measurable signal used for the analysis, or a suppression of any interfering phenomenon, or it has the effect of prolonging the working life of the sample.

It is often preferred that the signal which is detected is a photoluminescence signal, originating from a molecule, or a fraction of a molecule having fluorophore properties, naturally contained within or on the particle which is measured.

The particles which are to be detected are often "coloured" with one or several molecules which bind to the particle, are retained within the particle, or otherwise interact with the particle, the effect of this "colouring" being the enhancement of any signal for the particle, or being the direct source of a signal which thereby can be used to detect the particle.

In many aspects of the invention the effect of the "colouring" is to cause, or enhance, the attenuation of electromagnetic radiation such as visible light, or preferably to cause, or enhance, the emission of electromagnetic radiation such as chemiluminescence, or photoluminescence, e.g. fluorescence or phosphorescence, when exited with radiation which is substantially higher in energy that the emitted photoluminescence. One such "colouring" is the addition of Ethidium Bromide (EtBr) to the sample, where EtBr interacts with DNA material present in the sample, giving rise to fluorescence at approximately 605 nm when exited with light at approximately 518 nm (Handbook of Fluorescent Probes and Research Chemicals, page 145). This makes it possible, in the combination with the appropriate set of optical filters, to count a DNA-containing particle where EtBr can interact with the DNA, such particles are for instance cells containing DNA, in particular DNA containing somatic cells or bacteria, such as those present in milk, blood or urine.

It was surprisingly found that it was possible to use concentrations of fluorophore which were substantially lower than those normally used in system, often less than $\frac{1}{10}$th or $\frac{1}{100}$ or even less than $\frac{1}{1000}$; in particular this is advantageous where added fluorophore exhibits relatively similar properties in free form as in bound form, with regard to intensity and wavelength characteristics. As expected, such condition inherently reduce any signal emitted from a coloured particle, but surprisingly it was found that the ratio of the signal intensity in bound form to free form shifted in favour of bound signals. In particular it was found that a level of signal from fluorophore in free form in the sample which was comparable, and preferably less, in intensity to any random electronical signal (noise) and/or comparable in intensity to, and preferably less than, any other interfering signal was to be preferred.

It is often preferred that the liquid in which particles which are to be measured are suspended, is substantially at stand-still, where stand-still is defined as the situation where at least a part of the image of a particle does not move any more than it is contained substantially within the boundary of the same detection elements during one measurement period. The stand-still situation is preferably such that at least a part of the image of a particle does not move any more than it is contained substantially within the boundary of the same detection element during at least two measurement periods, thus allowing the detection of any weak signals which might indicate the presence of a particle.

In other embodiments of this invention, normally less preferred, the liquid in which particles which are to be measured are suspended, is substantially moving during measurement, in such a way that at least a part of the image of a particle gives rise to signal in two or more adjacent detection elements during one measurement period, or in such a way that at least a part of the image of a particle gives rise to signal in two or more adjacent detection elements during at least two measurement periods.

The liquid in which particles which are to be measured are suspended can be moving in more than one direction during measurement, for instance by controlling two sources of force, preferably which can be applied perpendicular to each other, thus giving the opportunity to move the sample in a predefined pattern, which can be used to improve the performance of any image processing device used to analyse the measured signal.

It is possible to perform more than one measurement and thus allowing a more accurate and/or sensitive assessment of the number of particles, for instance by measuring the same portion of the sample more than once and combining the results in order to improve the signal to noise ratio, and/or to measure more than one portion of the sample in order to increase the total number of particles which are counted to reduce the error in the assessment since the error in the particle count will normally follow count statistics where the relative error is expected to behave similar to one over the square root of number of counts. However, it is a characteristic feature of the present invention that its general character of detection based on a relatively large sample volume giving a large amount of information makes it possible to meet a predetermined statistical standard based on substantially one exposure.

In some embodiments of this invention the number of measurements which are taken is defined by a real time estimate of the number of particles already counted thus performing relatively fewer measurements when the sample contains a high number of particles and relatively more measurements when the sample contains a low number of particles, preferably by defining an approximate lower limit for the total number of counted particles in such a way as an appropriate accuracy in the measurement is obtained.

It is possible to assess the biological particles in a relatively short time thus allowing a high number of samples to be analysed per hour, often more than 400, and even as many as 1000 or more analysis per hour. In many preferred embodiments of this invention an even higher number analysis per hour is achieved by including more than one measurement unit, the measurement units working in parallel in a single instrument.

In many embodiments of this invention the signals which are detected are attenuation of electromagnetic radiation, for instance caused by absorption or scattering, and in many preferred embodiments of this invention the signals which are detected are emitted from the particles or the samples, for instance emission of photoluminescence (e.g. fluorescence and/or phosphorescence) or raman scatter, and in other embodiments of this invention the signals which are detected are caused by scatter.

Often more than one of the previously mentioned signals are detected simultaneously thus allowing more accurate or sensitive assessment of the number of particles or the assessment of any morphological property or to allow classification of a particle present in the sample, preferably by the use of more than one set of detection elements.

A monochromatic device can be used to separate electromagnetic radiation into one or more wavelength components before one or several of these wavelength components are transmitted onto the sample either one at a time or more than one at a time, preferably when more than one wavelength component is transmitted onto the sample simultaneously the wavelength components are transmitted onto different portions of the sample thus giving an opportunity to obtain qualitative as well as quantitative information about particles in the sample. This is in particular of interest when the sample contains particles which respond differently to different wavelength components.

Light which can be transmitted onto the sample can be focused by a focusing system, comprising one or more lenses. The effect of such a focusing system is often to increase the effective efficiency of the light source. As light source it is possible to use a thermal light source, such as a halogen lamp, or a gas lamp such as a xenon lamp, a light emitted diode, a laser or a laser diode. It is often preferred to use more than one light source for the purpose of increasing the flux of light onto the sample, for instance by using two or more light emitting diodes. It is also possible to use more than one light source where some of the light sources have different electromagnetic properties.

A monochromatic device can be used to separate electromagnetic radiation emitted from, or transmitted through the sample into one or more wavelength components before such electromagnetic radiation is detected by a detection element, either in such a way that one wavelength is measured at a time or in such a way that more than one wavelength components are measured at a time. This is in particular of interest when the sample contains particles which respond differently to different wavelength components for instance when a particle is capable of emitting photoluminescence with different properties dependent on the nature of the particle. This effect can also be produced by the use of more than one type of light source which have different wavelength characteristics, preferably in combination with a monochromatic device.

In many preferred embodiments of this invention electromagnetic radiation, such as UV or visible light is transmitted onto the sample, in order to give rise to photoluminescence, in a set-up where the light source, the sample compartment and the detection elements all are situated approximately on the same axes, preferably where the sample compartment is situated between the light source and the detector elements. Surprisingly it was found that under these conditions it was possible to remove substantially all the excitation light which was transmitted through the sample by means of filters, even in situation where high amounts of energy were used for the excitation. Further in many preferred embodiments of this invention it was found that it was possible to increase the efficiency of the electromagnetic radiation used for excitation by placing a reflecting device between the sample compartment and the detector which could reflect at least a portion of the energy transmitted through the sample compartment back towards the sample compartment, preferably where at least one of the surfaces which define the sample compartment was reflecting, preferably this reflecting device is one which has different reflectance properties at different wavelength, preferably in such a way that it is substantially transparent to the photoluminescence signal. One such reflecting device is a dichroic mirror.

It is often preferable to use one or several state of the art image processing techniques, such as 2 dimensional filtering or image identification, to assess the number of particles, or any morphological property of a particle.

As mentioned above, it is a particular feature of the invention that compared to traditional microscopy methods, the enlargement is from relatively small to very small. Thus, it is often preferred that the spatial representation exposed onto the array of detection elements is subject to such a linear enlargement that the ratio of the image of a linear dimension on the array of detection elements to the original linear dimension in the exposing domain is smaller than 40:1, normally at the most 20:1, preferably smaller than 10:1 and in many cases even at the most 6:1 or even smaller than 4:1.

The enlargement is suitably adapted to size of the particles to be determined Thus, for example, when the particles the parameter or parameters of which is/are to be assessed are of a size of between $\frac{1}{3}$ μm to 3 μm, the above-mentioned ratio is preferably in the range between 40:1 and 1:10, more preferably in the range between 20:1 and 1:10, such as in the range between 10:1 and 1:10. In most embodiments which have proved to give excellent results in practice, the ratio is in the range between 6:1 and 2:1.

When the particles the parameter or parameters of which is/are to be assessed are of a size between 3 µm and 100 µm, the above-mentioned ratio is normally in the range between 3:1 and 1:100, preferably in the range between 2:1 and 1:100. In many practical embodiments, the ratio will be in the range between 2:1 and 1:2. It can be interesting, in particular with small high precision detection elements, to work with very small rations, such as in the range between 1.4:1 and 1:100, e.g., in the range between 1:1 and 1:100.

Another way of expressing the ratio at which the image should preferably be formed on the array is to consider the imaging of the individual particle on the detection elements. It is often preferred that the individual particles the parameter or parameters of which is/are to be assessed are imaged on at the most 25 detection elements, in particular on at the most 16 detection elements and more preferred at the most 9 detection elements. It is even more preferred that the individual particles the parameter or parameters of which is/are to be assessed are imaged on at the most 5 detection elements, or even on at the most 1 detection element. The larger number of elements per particle will provide more information on the individual particles, while the smaller number of elements per particle will increase the total count that can be made in an exposure.

As mentioned above, it is one of the characterising features of the present invention that a relatively large volume of sample can be exposed to the detection array. The sample is contained in the interior of the domain or sample compartment, which normally has an average thickness of between 20 µm and 2000 µm, usually between 20 µm and 1000 µm and in many practical embodiments between 20 µm and 200 µm. Normally, the domain or sample compartment has dimensions, in a direction substantially parallel to the array of detection elements, in the range between 1 mm by 1 mm and 10 mm by 10 mm, but is will be understood that depending on the design, it may also be larger and, in some cases, smaller.

The volume of the liquid sample from which electromagnetic radiation is exposed onto the array is normally in the range between 0.01 µl and 20 µl. When the particles the parameter or parameters of which is/are to be assessed are of a size of between ⅓ µm to 3 µm, the volume of the liquid sample from which electromagnetic radiation is exposed onto the array is normally in the range between 0.01 µl and 1 µl. When the particles the parameter or parameters of which is/are to be assessed are of a size of between 3 µm to 100 µm, the volume of the liquid sample from which electromagnetic radiation is exposed onto the array is normally in the range between 0.04 µl and 4 µl.

As mentioned above, the sample is preferably at stand still during the exposure. However, in another embodiment, the sample in the domain or sample compartment is moved through the domain or sample compartment during the exposure, and the exposure is performed over a sufficiently short period of time so substantially obtain stand still condition during the exposure. In either case, there is a close control of the volume of the sample from which the exposure is made, which is one very preferred feature of the present invention.

When at least a major part of the electromagnetic radiation emitted from the sample during exposure originates from or is caused by electromagnetic radiation supplied to the sample from a light source, it is highly preferred at least a major part of the radiation from the light source having a direction which is transverse to the wall of the sample compartment or a plane defined by the domain, such as substantially perpendicular to the plane defined by the domain (or an increment plane if the compartment wall is curved), or between perpendicular and 10 degrees, preferably between perpendicular and 20 degrees, more preferably between perpendicular and 30 degrees and still more preferably between perpendicular and 45 degrees. This is in contrast to the case where the radiation enters from an edge, parallel to the plane of the sample compartment, which is considered highly disadvantageous as it will, for many sample types, give rise to sufficient illumination of only a small rim part of the sample.

As mentioned above, the size of the volume is suitably adapted to the desired statistical quality of the determination. Thus, where the determination is the determination of the number of particles in a volume, or the determination of the size and/or shape of particles, the size of the volume of the liquid sample is preferably sufficiently large to allow identification therein of at least two of the biological particles. More preferably, the size of the volume of the liquid sample is sufficiently large to allow identification therein of at least four of the biological particles. This will correspond to a repeatability error of approximately 50%. Still more preferably, the size of the volume of the liquid sample is sufficiently large to allow identification therein of at least 10 of the biological particles. This will correspond to a repeatability error of approximately 33%. Even more preferably, the size of the volume of the liquid sample is sufficiently large to allow identification therein of at least 50 of the biological particles. This will correspond to a repeatability error of approximately 14%. Evidently, where possible, it is preferred to aim at conditions where the size of the volume allows identification of even higher numbers. Thus, when the size of the volume of the liquid sample is sufficiently large to allow identification therein of at least 100 of the biological particles, it will correspond to a repeatability error of approximately 10%, and when the size of the volume of the liquid sample is sufficiently large to allow identification therein of at least 1000 of the biological particles, it will correspond to a repeatability error of as low as approximately 3%.

Expressed in another, more specific manner, one main aspect of the present invention is defined as a method for the assessment of at least one quantity parameter and/or at least one quality parameter of biological particles in a liquid analyte material, comprising applying a volume of between 0.01 µl and 20 µl of a liquid sample representing the liquid analyte material, or particles isolated from a volume of a liquid sample representing the liquid analyte material, to an exposing domain from which exposing domain electromagnetic signals from the sample in the domain can pass to the exterior, exposing, onto an array of active detection elements, an at least one-dimensional spatial representation of electromagnetic signals having passed from the domain, the representation being one which is detectable as an intensity by individual active detection elements, under conditions which will permit processing of the intensities detected by the array of detection elements during the exposure in such a manner that representations of electromagnetic signals from the biological particles are identified as distinct from representations of electromagnetic signals from background signals, the conditions involving such a linear enlargement that the ratio of the image of a linear dimension on the array of detection elements to the original linear dimension in the exposing domain is smaller than 10:1, and such that the individual particles the parameter or parameters of which is/are to be assessed are imaged on at the most 25 detection elements of the array of detection elements, the sample in the domain or sample compartment being at stand still during the exposure, and in the case where at least a major part of the electromagnetic radiation emitted from the sample during exposure originates from or is caused by electromagnetic radiation supplied to the sample from a light source, then at least a major part of the radiation from the light source having a direction which is transverse to the wall of the sample compartment or a plane defined by the domain, processing the intensities detected by the detection elements in such a manner that signals from the biological particles are identified as distinct from background signals, and correlating the results of the processing to the at least one quantity parameter and/or the at least one quality parameter of the liquid analyte material.

As mentioned above, the signal which is detected by the detecting elements originates from one or several types of molecules of types which bind to, are retained within, or interact with, the biological particles, such molecules being added to the sample or the isolated particles before or during exposure, the molecules being molecules giving rise to one or several of the following phenomena: attenuation of electromagnetic radiation, photoluminiscence when illuminated with electromagnetic radiation, scatter of electromagnetic radiation, raman scatter. In the presently most preferred embodiments an effective amount of one or more nucleic acid dyes and/or one or more potentiometric membrane dyes is added.

The duration of the exposure is in normally the range from 100 milliseconds to 5 seconds, in particular in the range of 0.5 to 3 seconds. The exposure may be performed as multiple exposures before the intensities detected by the detection elements are processed, but it is normally preferred that the exposure is performed as a single exposure.

A number of embodiment and variants of the invention appear from the figures and examples which follow, as well as of from the following detailed description of embodiments.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiments of the herein disclosed invention are meant to be included as come within the scope of the claims.

Figure 1:
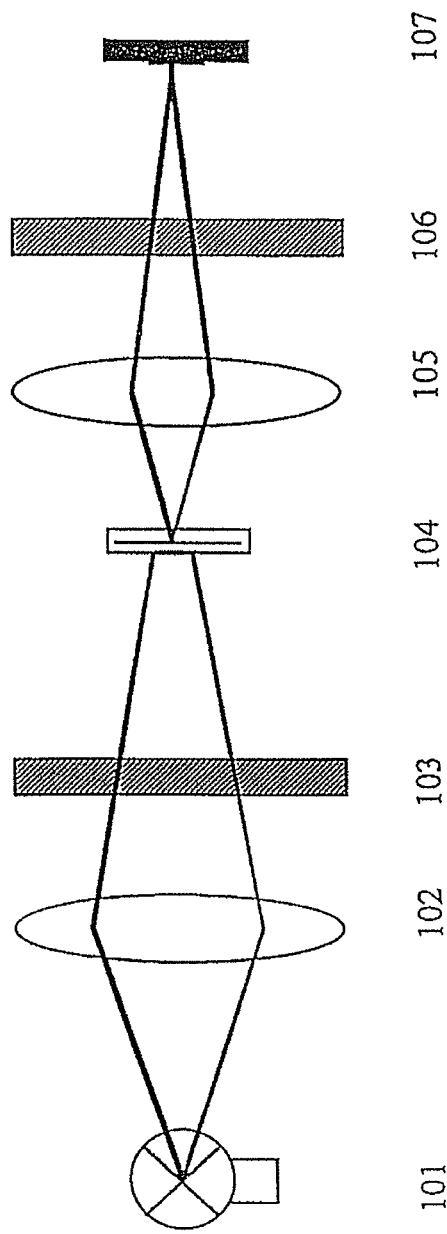
FIG. 1 illustrates one embodiment of this invention, particularly suited for the assessment of particles by the use of fluorescence.

One aspect of the invention concerns a method for compression of intensity information representing distinct objects scattered over an area, an object being represented by a variation in the intensity information.

The information existing in the form of varying degrees of measurable intensity of a physical property distributed over a confined area divided into sub-areas, each of which sub-areas having assigned thereto an index uniquely identifying the sub-area. According to the invention the method comprising determination of the intensity of the physical property.

One such method of determining the intensity of the physical property could be a read-out of the electrical signal from an array of detection element such as CCD-elements exposed to electromagnetic radiation radiated from the objects scattered oven an area. Another such method could be by exposing a photografich film to electromagnetic radiation radiated from the objects scattered over an area, thereby generating a "picture" of the intensity of the physical property which then could be digitized in such a manner that for instance a number is assigned to a distinct interval of intensities represented by for instance gray-scale in the "picture"

When the determination of the intensity has been done the compression could be performed by the following:

a) defining a sub-area of interest situated in a group of sub-areas comprising of at least 2×2 sub-areas situated adjacent to each other, b) evaluating in said sub-area of interest at least one directional derivative(s) of the measurable intensity in the sub-area of interest with respect to predetermined geometrical direction(s) in the plane of the confined area, the directional derivative(s) is (are) based on measurable intensities in sub-areas situated adjacent to or in proximity of the group of sub-area, c) based on the evaluation of the at least one directional derivative an attribute is assigned to the value assigned to said sub-area of interest; the attribute represent an adjusted measurable intensity and/or information(s) related to a predetermined strategy for adjustment of the measurable intensity in the sub-area of interest or sub-areas situated adjacent to or in proximity to the sub-area of interest.

The steps a)-c) can be performed for substantially all sub-areas of the confined area.

The evaluation of the directional derivatives is used to give an indication of where the center of an object is situated relative to the confined area and to give a measure of which of the sub-area in the confined area which is subject to be a sub-area in which information from neibouring sub-areas should be assigned to. Such information could be the intensity information.

The steps a)-c) can be repeated successively for some of the sub-areas or for all of the sub-areas.

The use of the attribute enables the possibility of storing information of the about the sub-area of interest such that an elliptical, hyperbolical or and parabolic method (in a mathematical understanding) can be used as a strategy for distribution of intensity information from some of sub-areas to selected sub-areas in the confined area, the number of selected sub-areas are lower in number than the sub-areas contained in the confined area.

EXAMPLE 1

Detection of Fluorescence Signals from Ethidium Bromide (EtBr) Bound to DNA in Somatic Cells in Milk at Different Initial Concentration Levels of Ethidium Bromide The sample material was cow bulk milk. To each of three portions of the same sample material, used for the below Experiments A, B and C, was added a buffer in the ratio of two parts by volume of buffer solution to one part by volume of milk. The buffer solutions were identical except that they contained different amounts of EtBr. The buffer solutions were prepared according to the guidelines of International IDF standard 148A:1995—"Method C, concerning Flouro-Opto-Electronic Method" (Experiment A, EtBr concentration 33 µg/ml); for Experiment B, the concentration of EtBr was 10% of the prescribed amount, and for Experiment C, it was 1% of the prescribed amount.

The resulting sample materials were measured in a set-up as follows (cf. FIG. 1): A halogen lamp 101 of type OSRAM (41890 SP 12V, 20 W, 10 degree reflector) was used as a light source emitting electromagnetic radiation onto the sample contained in a sample compartment 104 through a collecting lens 102 and through an optical filter 103 selectively transmitting light in the waveband between 400 and 550 nm (Ferroperm SWP 550). Any fluorescence signal originating from the sample was focused using a lens 105 with a collection angle of approximately 10 degrees and producing an image which was approximately 4 times larger than the source on a two-dimensional array of detection elements 107, constituted by a CCD of the type Loral Fairchild (CCD 222). An optical filter 106 selectively transmitting light in a waveband between 600 and 700 nm (Schott OG590 and KG5, thickness 3 mm) was inserted between the sample compartment and the array.

The final concentration of EtBr in each experiment and the operation of the light source and the detector elements was as follows:

| Experiment | EtBr (µg/ml) | Lamp (Volt) | CCD Integration time (ms) |
|---|---|---|---|
| A | 33 | 12 | 800 |
| B | 3.3 | 12 | 800 |
| C | 0.33 | 13 | 1600 |

The data from the two dimensional array of detection elements was digitised and collected on a computer (not shown) for later analysis.

Results

Figure 2:
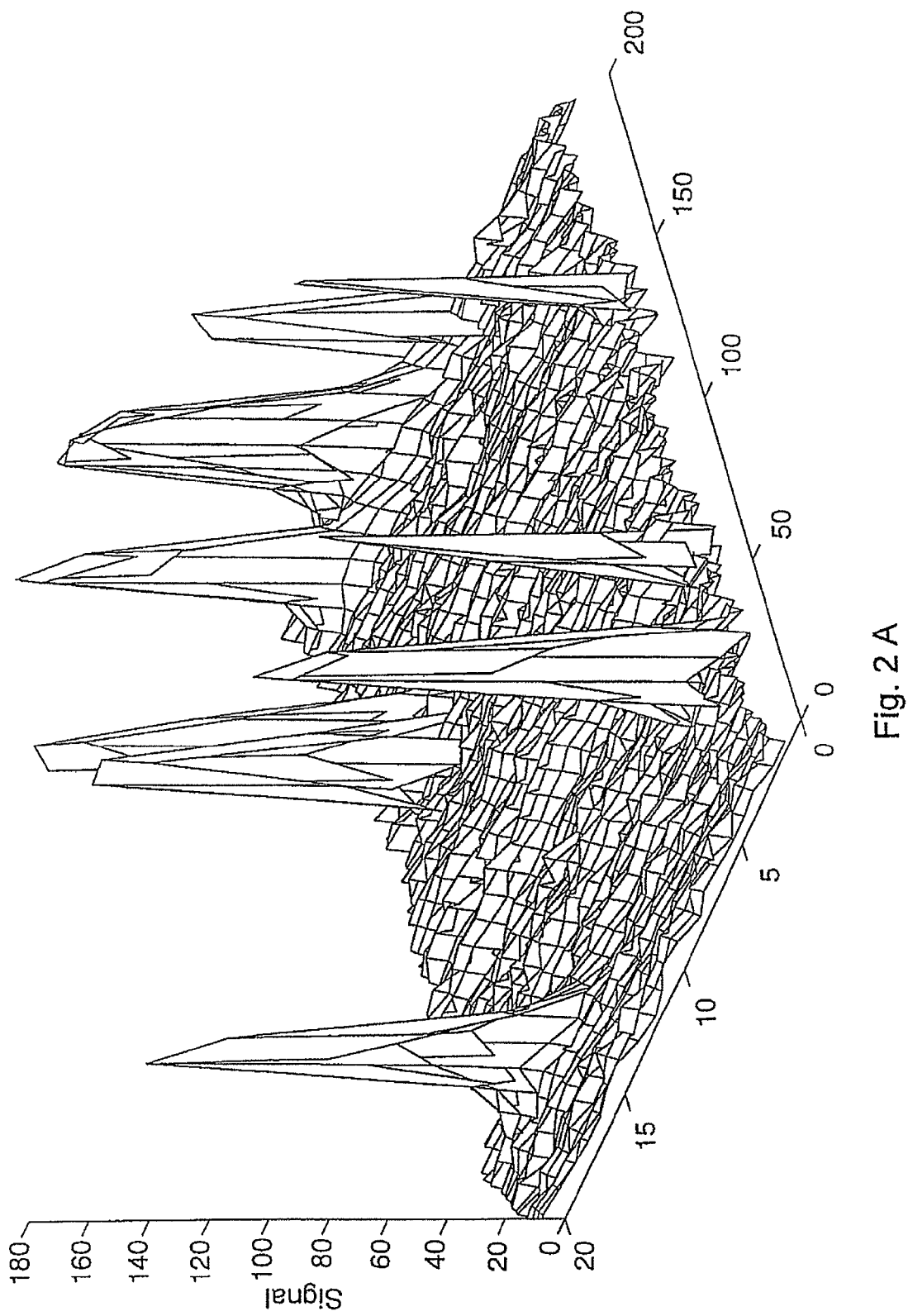
FIG. 2 illustrates the effect of varying the initial concentration of fluorescent labelling dye.
Figure 2:
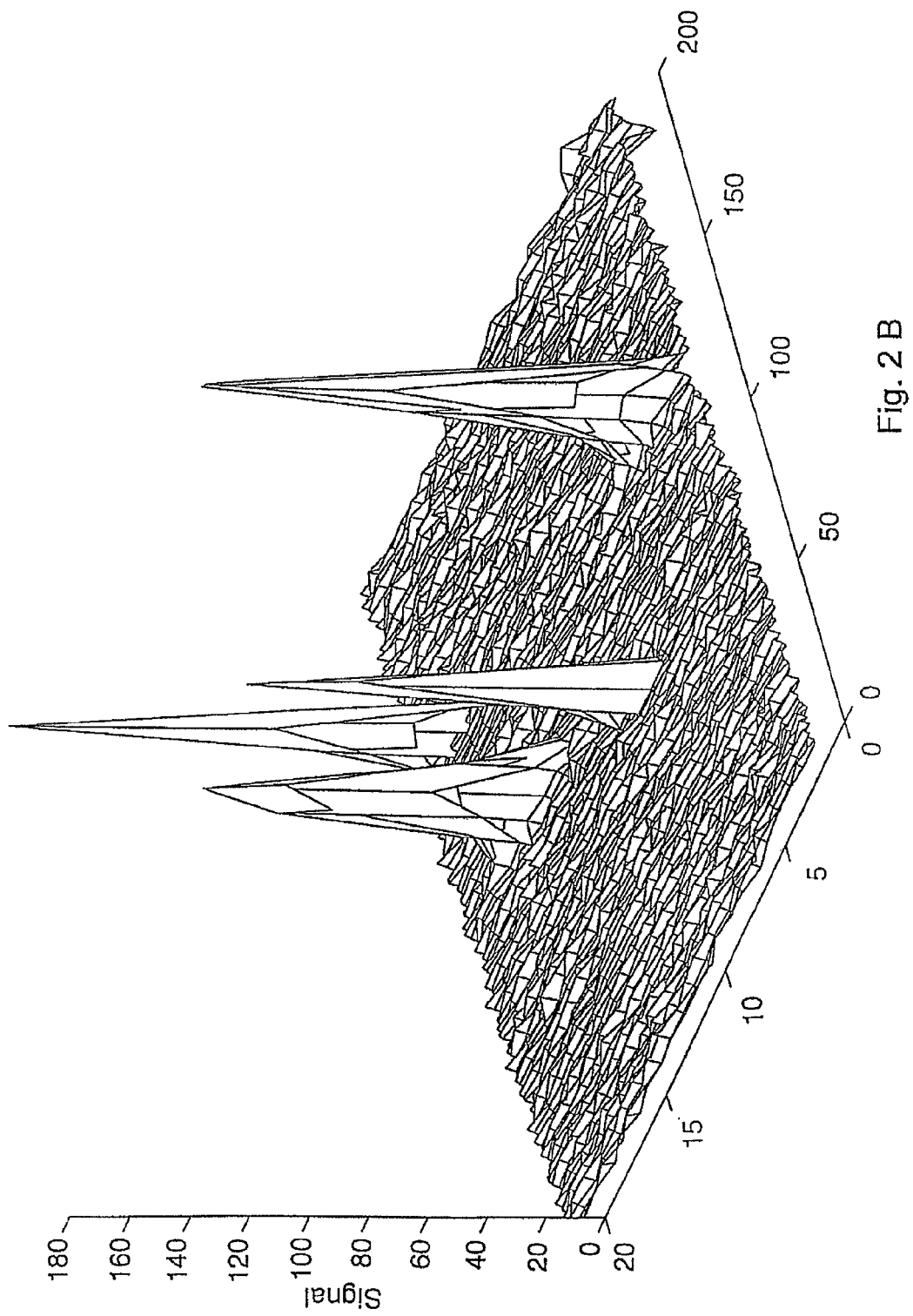
Figure 2:
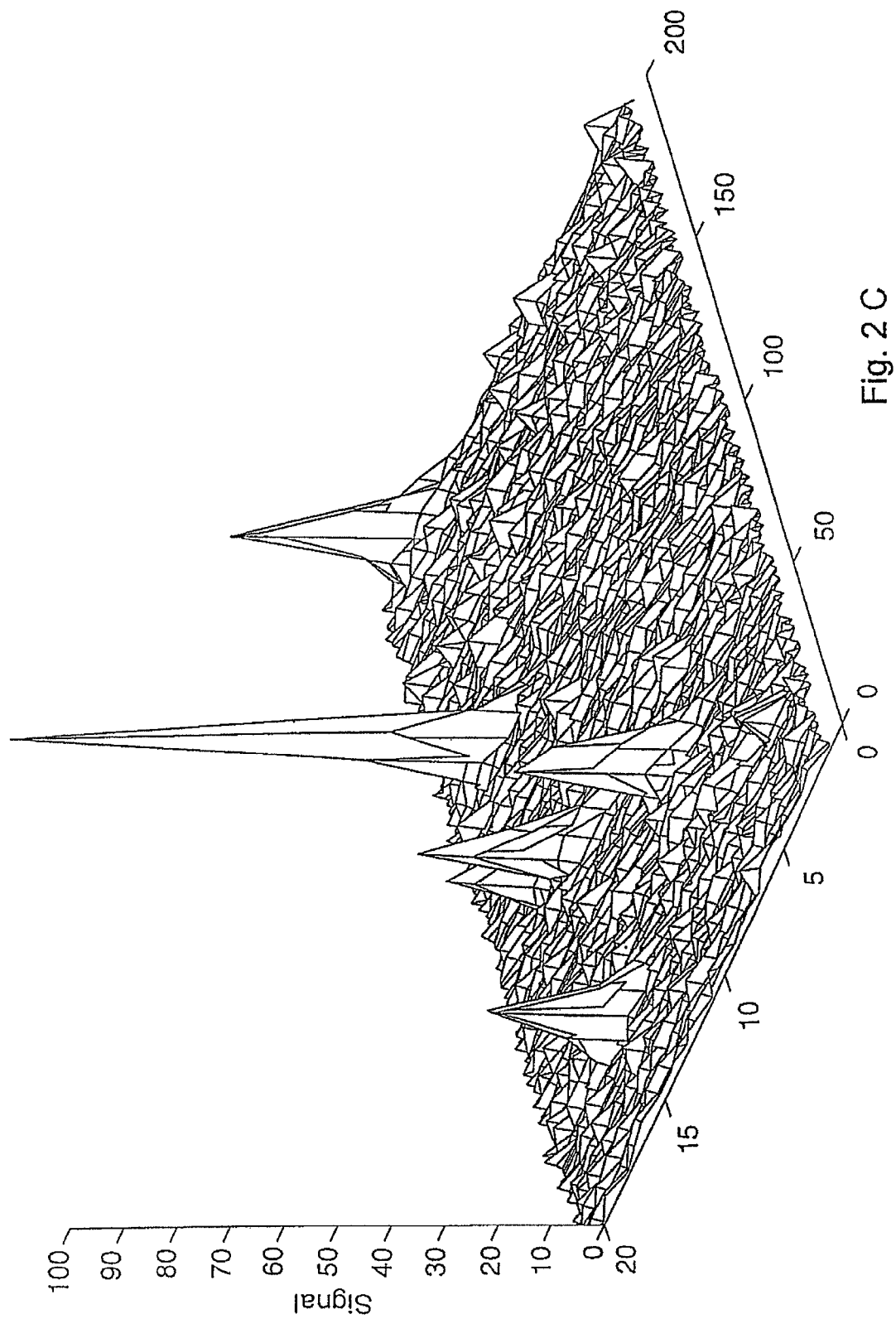

Data from the two dimensional array of detection elements was used to produce images in which the intensity detected by each element is illustrated as height over a graphic representation of the array. An illustration of this type of typical signals from each experiment is shown in FIG. 2, where FIG. 2A is a representation of intensities as observed in experiment A, FIG. 2B is a representation of intensities as observed in experiment B, and FIG. 2C is a representation of intensities as observed in experiment C. Peak-like structures in the figures, distinct from representations of electromagnetic signals from the sample background, are representations of EtBr bound to DNA in somatic cells contained in the milk samples.

In all cases the figures are the numerically positive result of the subtraction of one measurement from the sample, from another measurement of a different portion of the sample, by using the formula: $Signal_{(ij)}=ABS(meas1_{(ij)}-meas2_{(ij)})$, where i and j refer to the row and column of the CCD, thus suppressing any systematic bias of the measurement system.

In experiment A, illustrated in FIG. 2A, the signal intensity was such that a majority of the cells showed signals which caused charge overflow on the CCD, resulting firstly in the cut-off of the signal due to the fact that the signal was outside the range of the detector elements, and secondly in broadening of the signal top due to charge transfer from overloaded detection elements to neighbouring detection elements. In addition it is obvious that the variation in the signals of the background is high, presumably due to interaction between free EtBr and the sample matrix (for instance fat globules and protein micelles).

FIG. 2B illustrates typical signals as observed in Experiment B. Experiments A and B were identical apart from the concentration of EtBr used, and the beneficial effect of the lowering of the EtBr concentration on the signal intensity and signal broadening is evident. In addition, the random variation in the background is about ½ of the variation observed in experiment A.

FIG. 2C illustrates typical results from Experiment C. In this experiment, the intensity of excitation light as well as the integration time of the detection elements were increased. The result from experiment C is that the signals are considerably weaker than in experiment B, with a background signal of similar magnitude.

Conclusion

The above results illustrate that it is possible to detect signals from somatic cells using concentrations of EtBr which are considerably lower than concentrations normally used for the fluorescence detection of DNA-containing particles.

One preferred embodiment of this invention is based on an optical system which has a collection angle of between 40 and 70 degrees, as compared to the 10 degrees used in the present example; and this will result in the collection of approximately 10 to 300 times as much energy, making it possible to reduce the concentration of the reagent even further.

EXAMPLE 2

Removal of Signal Bias by Combination of Measurements from a Linear Array of Detection Elements Removal of systematic signal bias can be of interest in the processing of measured signals. In the present example a linear array of detection elements of the type Hamamatsu (S3902-128Q) was used in an arrangement similar to the one illustrated in FIG. 1. Under the conditions used, the array of detection elements gave a readout which had a systematic bias between detection elements with even index and detection elements with odd index. A series of 2 measurements was carried out using water as sample material.

Results

Figure 3:
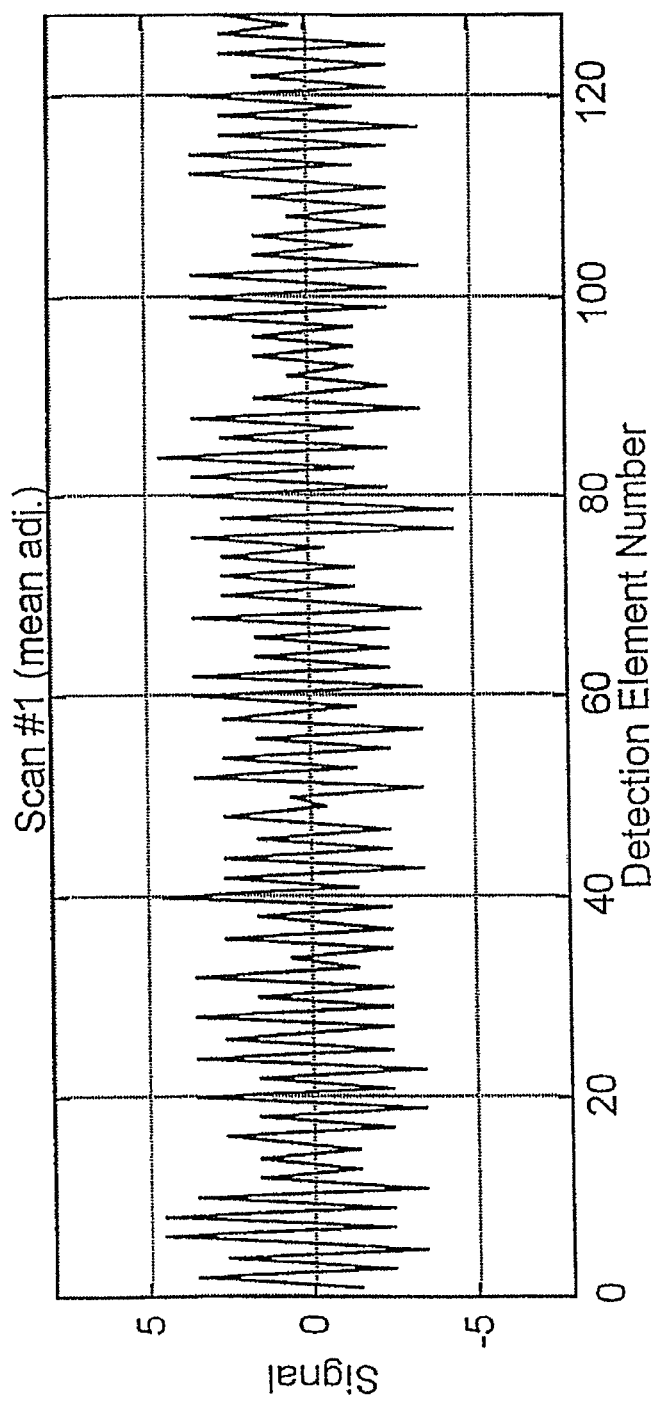
FIG. 3 illustrates the possible removal of systematic bias by the subtraction of measured signals.
Figure 3:
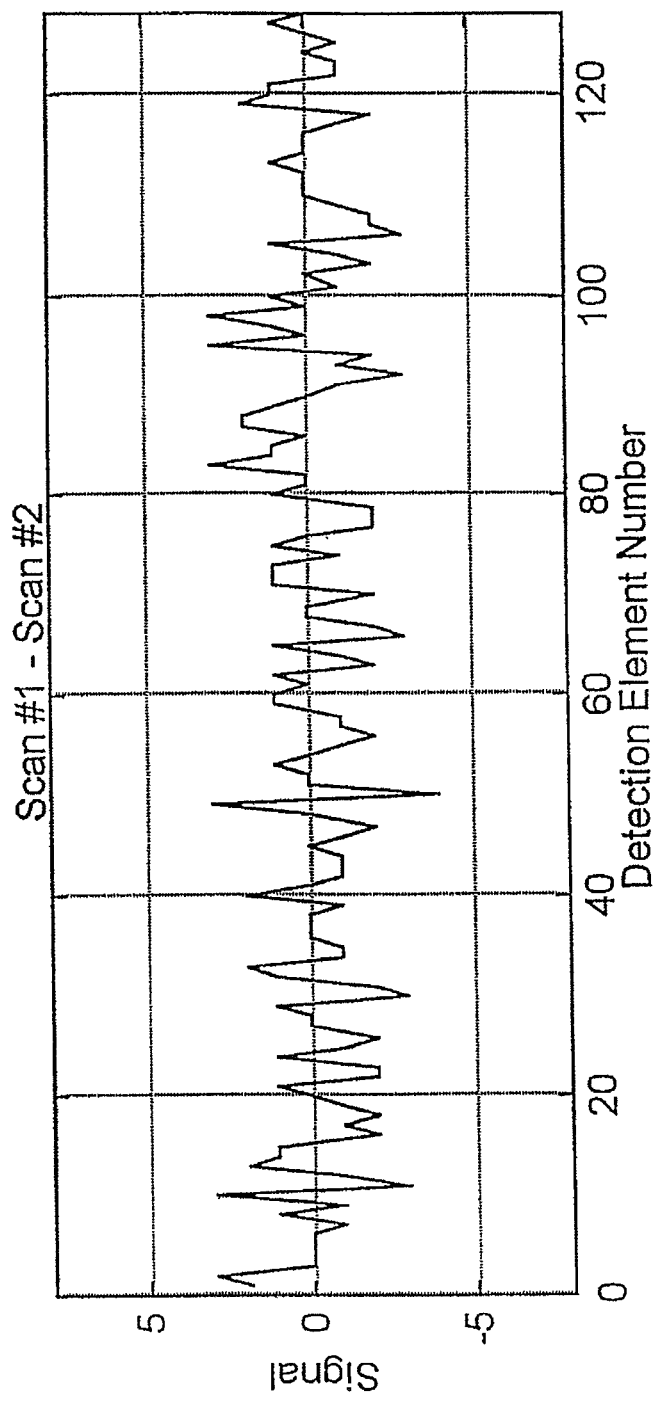

FIG. 3 shows the results of the measurements of water. FIG. 3A shows the result from the first measurement after the measurement had been adjusted for the mean bias. From FIG. 3A it is apparent that there is a clear difference in the signal intensity of odd and even detection elements, in that elements with an odd index have generally lower signal. FIG. 3B shows the result of scan 1 after the results from scan 2 have been subtracted. What is apparent is that the systematic effect of odd and even detection elements has been substantially removed, resulting in a signal with a baseline which can be expected to have variations of more random character; the amplitude of this noise can be expected to have an amplitude of approximately 1.41 the amplitude of any random noise present in one measurement.

Conclusion

The conclusion from the above result is that it is possible to remove a systematic bias by subtracting one measurement from another. In addition to variations in the detecting system, systematic bias can be caused by many other factors, such as particles adhering to the wall in a flow system, variations in the intensity of excitation light from a light source consisting of a plurality of elements such as light-emitting diodes, etc. Compensation for systematic bias, performed, e.g., as illustrated in the present example and in Example 1, will enhance the distinction between representations of electromagnetic signals from the biological particles and representations of electromagnetic signals from the sample background. However, for many applications, the inherent distinction obtained using the method of the present invention will be adequate or more than adequate even without a compensation for systematic bias. The use of disposable sample compartments used only once will rule out any problems ascribable to adhering particles in a flow system.

EXAMPLE 3

Optical Configuration for Wide Angle Collection of Signal from a Sample

It can be demonstrated that the intensity of any signal collected from a sample is dependent on the square of the collection angle. In conventional automated microscopy, the collection angle is at the most 20 degrees and normally considerably lower, such as 1-5 degrees. Because of the low magnification (or no magnification) which can be used according to the present invention, and the robust processing made possible thereby, a much larger collecting angle can be used. In the present example two different optical arrangements are used to obtain a collection angle of approximately 40 and approximately 70 degrees, respectively.

Figure 4:
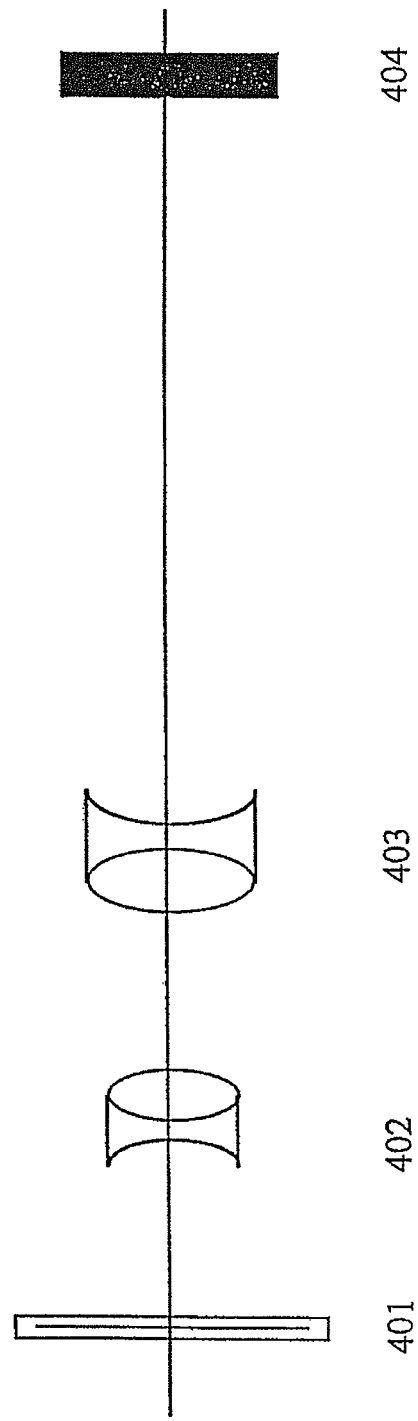
FIG. 4 illustrates an optical arrangement allowing collection of signals with a collection angel of approximately 40 degrees.

FIG. 4 illustrates an optical arrangement which produces a collection angle of approximately 40 degrees when collecting a signal from a sample compartment 401 and projecting it onto detection elements 404, by using two achromatic lenses, one 402 of the type Melles Griot 01 (LAO 014: F=21 mm, D=14 mm) and another one 403 of the type Melles Griot 01 (LAO 111: F=80 mm, D=18 mm).

Figure 5:
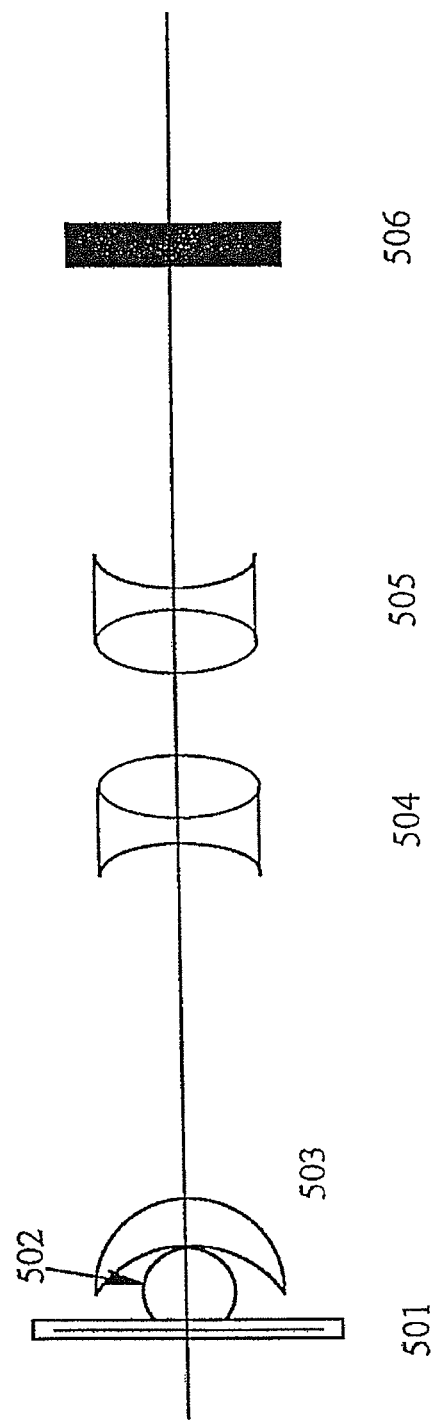
FIG. 5 illustrates an optical arrangement allowing collection of signals with a collection angle of approximately 70 degrees.

FIG. 5 illustrates an optical arrangement which produces a collection angle of approximately 70 degrees when collecting a signal from a sample compartment 501 and projecting it onto detection elements 506, by using one immersion lens 502 with radius of approximately 5 mm and width of approximately 8.3 mm, and one aplanatic meniscus lens 503 with one radius of approximately 12.5 mm and one radius of approximately 10.5 mm, and two identical achromatic lenses 504 and 505 of the type Melles Griot 01 (LAO 028: F=31 mm, D=17.5 mm).

EXAMPLE 4

Components of a Disposable Measurement and Sampling Unit

Figure 6:
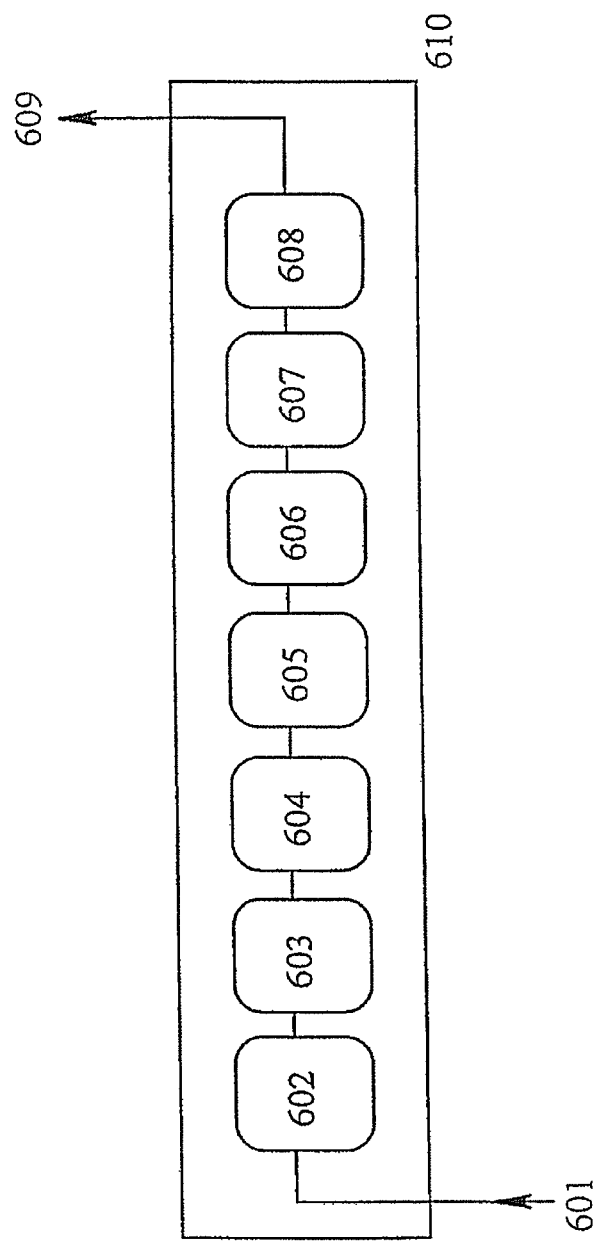
FIG. 6 illustrates components used for a flow system.

The components of a flow system which can be used for the assessment of biological particles according to principles of the present invention are given in FIG. 6. The components in FIG. 6 are as follows: An inlet 601 where the sample is introduced to the flow system, a pump 602 situated upstream from the sample compartment, a valve 603 controlling the inlet flow of the sample, means 604 allowing introduction of one or several intentionally added chemical components, means 605 which allow the mixing of the sample and one or several chemical components and/or any other mechanical or physical operation such as retaining particles, a sample compartment 606, a valve 607 controlling the flow from the sample compartment, a pump 608 situated downstream of the sample compartment, an outlet 609 from the flow system and a unit 610 housing one or several of the components of the flow system.

Depending on the nature of the sample which is to be analysed and other factors associated with the sampling and measurement, the preferred flow system would not always comprise all the components arranged as shown in FIG. 6, or one or more of the components could be integrated into one component. The present example discusses several possible constructions.

A—A Flow System Contained in a Disposable Unit

Several applications of the present invention can be based on a flow system contained in a removable and disposable unit or in a unit which can be regenerated. Such a system will have a number of advantages, including the following: Elimination of a stationary flow system that would need maintenance such as cleaning. The possibility of being able to sample and measure without any further handling of a sample, which makes the handling of hazardous material more safe.

One such flow system unit 610 is based on following components: An inlet 601 where the sample can be introduced in the flow system unit, preferably a valve 603 close to the inlet or integrated with the inlet and allowing liquid sample to flow only in one direction, preferably a chemical container 604 for any addition of chemical components, preferably a mixing chamber or a manifold 605 allowing the sample and any chemical components to mix, a sample compartment 606 where a measurement of any signal from the sample will be made, a valve 607 controlling the flow of the sample through the sample compartment, preferably a valve which can allow gas or air to pass freely but which closes substantially irreversibly upon contact with the sample, and finally a pump 608 capable of moving the sample from the inlet to or past the valve 607.

When it is intended that any sample entering the inlet can be retained within the flow system unit upon completion of the analysis, an outlet from the flow system unit through which the sample could leave the system will normally not be provided. Upon completion of the analysis, such a flow system unit can be safely disposed of or regenerated regardless of the nature of the sample or any chemical components added to the sample.

B—A Flow System Contained in a Disposable Unit for the Sampling of Large Volumes Analysed by Multiple Measurements For some purposes, it may be interesting to be able to measure relatively large volumes of sample material by multiple measurements of a number of individual samples taken from a larger volume. This may, for example, apply when assessing the possible presence and, if present, the concentration, of bacteria which are objectionable even when being present in very small numbers, such as Salmonella. In such a case, it may be of interest to perform a small, or a large, series of measurements of "normal volume" samples taken from a larger, but well-defined, volume of sample material, and then optionally relating the results from the small or larger series of volumes to the well-defined larger volume. According to the present invention, also this can be accomplished using a flow system contained in a removable and disposable unit or a unit which can be regenerated. There can be several advantages of such a system, including: Improved sensitivity and precision due to multiple measurements and thereby measurement of a larger total volume. Elimination of a stationary flow system which would need maintenance such as cleaning. The possibility of being able to sample once and then measure several times without any further handling of a sample makes the handling of hazardous material more safe.

One such flow system unit 610 can be based on following components: An inlet 601 where the sample can be introduced in the flow system unit, preferably a valve 603 close to the inlet or integrated with the inlet and allowing liquid sample to flow only in one direction, preferably a chemical container 604 for any addition of chemical components, preferably a mixing chamber or a manifold 605 allowing the sample and any chemical components to mix and having volume at least corresponding to the volume of the large sample with added chemical components, a sample compartment 606 of a "normal volume" where measurement of any signal from the sample is made sequentially on a series of samples withdrawn from the large sample, a valve 607 controlling the flow of the individual sample through the sample compartment, and finally a pump 608 which, in connection with the individual measurements, is capable of passing at least a portion of the sample contained in the mixing chamber to the sample compartment for the measurement, the pump preferably having capacity to retain, in a large sample entering mode, at least the volume of sample entering the inlet.

The flow system would need the controlling of at least one valve and/or a pump allowing different portions of the sample to be analysed at a time.

C—A Flow System Contained in a Disposable Unit for the Sampling of Large Volumes Analysed by a Single Measurement It is often of interest to be able to measure a large volume of sample. Also this can be accomplished using a flow system contained in a removable and disposable unit or a unit which can be regenerated. The advantage of such system would include: Improved sensitivity and precision due to measurement of a large volume. Elimination of a stationary flow system that would need maintenance such as cleaning. The possibility of being able to sample and measure without any further handling of a sample makes the handling of hazardous material more safe.

One such flow system unit 610 could be based on the following components: An inlet 601 where the sample is introduced in the flow system unit, preferably a pump 602 or a valve 603 close to the inlet or integrated with the inlet and allowing liquid sample only to flow in one direction, passing the sample to a particle retaining means 605 preferably containing means to hold at least the volume of sample entering the inlet, or connected to an outlet 609 allowing the sample to leave the flow system unit, preferably a chemical container 604 for any addition of chemical components connected to the particle retaining means, preferably a mixing chamber of manifold 605 allowing the sample and any chemical components to mix, a sample compartment 606 where a measurement of any signal from the sample would be made, a valve 607 controlling the flow of the sample through the sample compartment, preferably a valve which can allow gas or air to pass freely but closes substantially irreversibly upon contact with the sample, and finally a pump 608 capable of passing at least a portion of the sample contained in the particle retaining means through the chemical component container to the sample compartment for the measurement.

With slight variation in the arrangement of the components it would be possible to measure the signal from the particles in the sample while still retained on or in the particle retaining means. One possible arrangement could be to include the particle retaining means in the sample unit, and passing the sample through the sample unit. Then preferably to pass any chemical component through or into the sample compartment to allow the mixing with any retained particle and finally to perform the measurement.

D—A Stationary Flow System for the Measurement of Several Samples

In many applications it would be of interest to be able to measure more than one sample without the replacement of any part of the flow system between analysis. Such a flow system would normally be a stationary part of an analytical instrument.

One such flow system could be constructed as follows: an inlet 601 where the sample enters the flow system and a pump 602 for the flowing of the sample, preferably a valve 603 for controlling the flow, preferably a reservoir for chemical components 604 which can preferably contain chemical components for the measurement of more than one sample, preferably a mixing chamber 605 for the mixing of the sample and any chemical component, a sample compartment 606 for the measurement of a signal from the sample, preferably a valve 607 controlling the flow of sample through the sample compartment, and an outlet 609 where the sample leaves the flow system.

EXAMPLE 5

Figure 7:
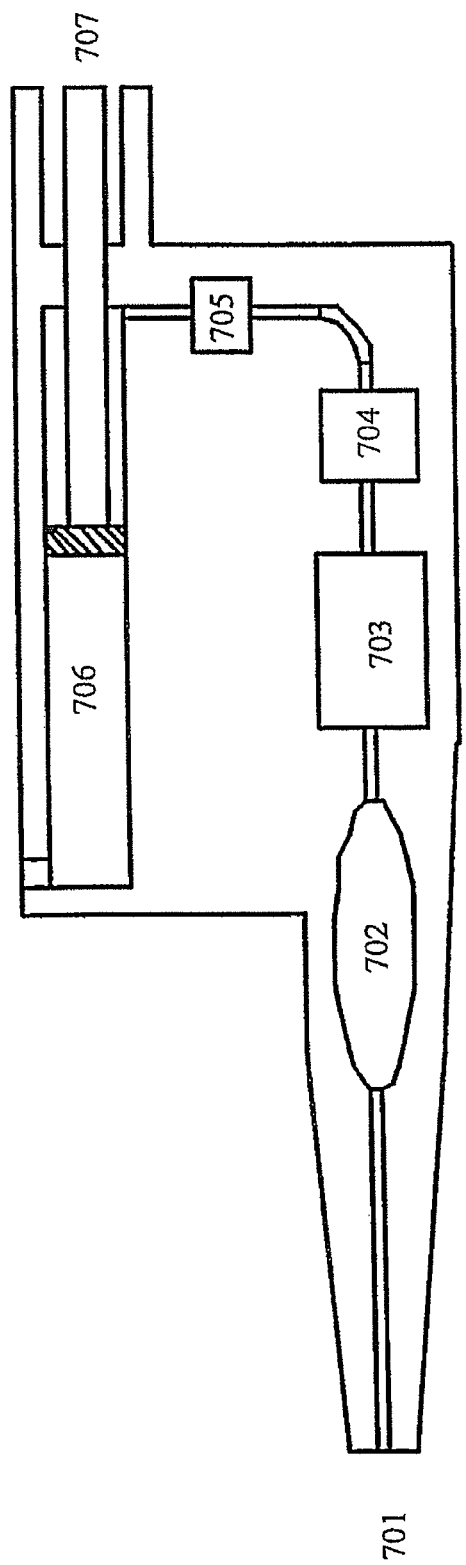
FIG. 7 illustrates a disposable measurement and sampling cell for the assessment of the number of somatic cells in a volume of milk.

A Disposable Measurement and Sampling Unit for the Assessment of the Number of Somatic Cells in a Volume of Milk The components of a flow system which can be used for the assessment of somatic cells in milk are shown in FIG. 7:

An inlet 701 where the sample is introduced to the flow system, a compartment 702 containing reagents prior to analysis, a compartment 703 which allows a substantially homogeneous mixing of the milk with the reagents, a sample compartment 704, a valve 705 controlling the flow from the sample compartment, a piston pump capable of producing vacuum, consisting of a chamber 706 with connection to the flow system and the exterior and a piston 707 which has such dimensions that it fits closely in the chamber, thus resulting in a low pressure on the flow system side of the pump chamber when moved into the chamber.

Prior to analysis, the sample inlet is immersed in the milk sample to be analysed. While the sample inlet is immersed in the milk sample, the sample is introduced to the flow system of the disposable measurement and sampling unit by moving the piston at least partially into the pump chamber. The vacuum produced should be of such magnitude that the milk sample flows through the reagent compartment, thus dissolving or suspending at least a portion of the reagents present in the compartment, and into the mixing compartment.

Preferably, the mixing compartment has a sufficiently large volume to secure that it becomes only partially filled with the milk and any reagents dissolved or suspended, thus allowing the content of the mixing compartment chamber to flow freely in the chamber and thus to be effectively mixed.

After the mixing has been completed, the piston is moved further into the pump chamber, thus producing vacuum capable of passing the milk sample into the sample compartment and further into the valve which closes upon contact with the sample thus substantially stopping the flow of sample through the sample compartment.

The dimension of the reagent compartment should be adequate to allow the storage of the reagents used, for instance 2 mg Triton X100 (t-Octylphenoxypolyethoxyethanol) and 5 µg Propidium Iodide (CAS-25535-16-4). The shape of the void inside of the reagent compartment should preferably be such as to enhance the solvation or suspension of the reagents contained in the compartment prior to analysis.

The mixing compartment has a volume of about 200 µl, depending on the total amount of milk used for the analysis. The shape of the void of the mixing compartment should be such as to allow any liquid to flow from one boundary to another thus allowing a thorough mixing.

The sample compartment consists of two substantially parallel planes forming a void with the approximate dimensions of 10×10×0.07 mm (height, with, depth). Depending on the method used for the production of the unit, then either the average depth of the sample compartment is substantially identical for all individual disposable measurement and sampling units thus allowing reproducible volumes of milk to be present in the sample compartment during analysis or it is possible to label each individual disposable measurement and sampling unit, this label identifying the approximate depth of the sample compartment thus allowing the instrument to compensate the assessment of somatic cells in milk for the varying depth of the sample compartment.

The valve used in the disposable measurement and sampling unit is one which is capable of letting air pass through until a liquid comes in contact with it. When a liquid has been in contact with the valve it is substantially irreversibly closed thus allowing neither liquid nor air to pass through it. One such valve can be constructed by using fibre material from Porex Technologies GmbH, German (XM-1378, EDP#NS-7002).

EXAMPLE 6

Figure 8:
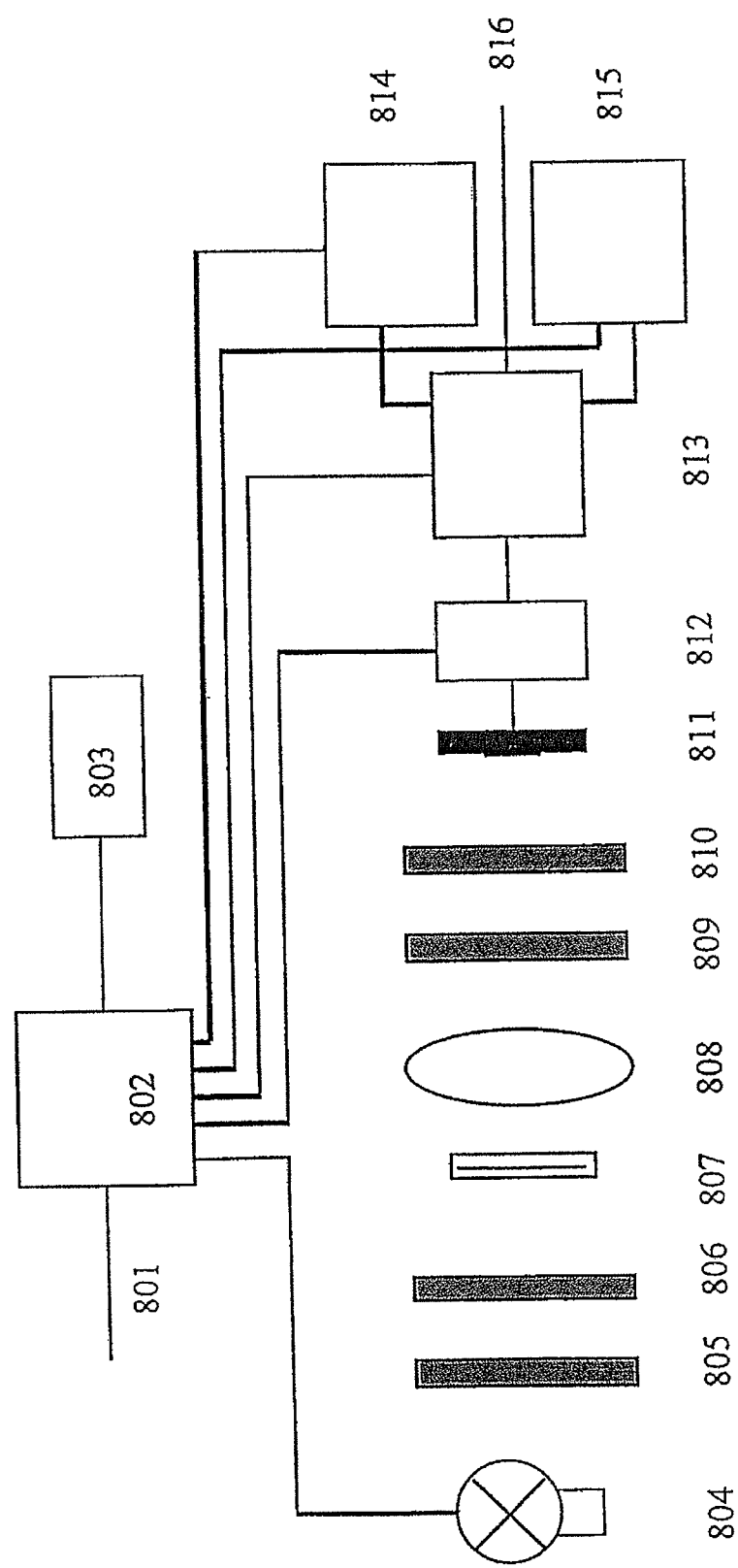
FIG. 8 illustrates an instrument for the assessment of the number of somatic cells in a volume of milk.

An Instrument for the Assessment of the Number of Somatic Cells in a Volume of Milk FIG. 8 illustrates an instrument which can be used for the assessment of the number of somatic cells in a volume of milk sample. The instrument is powered by either an external power source 801 or by an internal power source such as a lead acid (12V 2.2 Ah) rechargeable battery 803, manufactured by Wetronic Inc. (WE12-2.2).

The Power supply/battery charger 802 supplies the different units of the instrument. The power supply can use power from either the external or the internal power source, and is capable of switching between the two sources during operation. It is possible to reduce the power consumption when the instrument is in stand-by.

The assessment of the number of somatic cells is performed by detecting a fluorescence signal originating from a fluorochrome bounded to DNA within somatic cells present in the sample compartment 807. The sample compartment is defined by two substantially parallel planes of transmitting material thus forming a compartment with dimensions of about 10×10×0.7 mm (height, width, depth).

The fluorescence is generated by passing light of high energy (excitation light of wavelength 550 nm or less) through the sample compartment, with direction towards the detection module 811. The source 804 of the excitation light can be either a halogen lamp of type OSRAM-64255 (8V, 20 W Photo Optic Lamp) or a number of light emitting diodes, for instance 4 or more, of type NSPG-500S or NSPE-590S (Nichia Chemical Industries Ltd., Japan).

In order to remove substantially any component from the excitation light with wavelength above 550 nm from reaching the sample compartment, an optical filter 805 is inserted in the light path. This filter of the type Ferroperm SWP550, double sided interference filter on a 2 mm substrate (Hoya, CM-500) which absorbs infra-red radiation.

To further preventing infra-red radiation from reaching the sample compartment a heat absorbing filter 806 is placed in the light path. This filter is of the type Schott KG5 or KG3 (3 mm in thickness). This filter can be omitted if light emitting diodes are used as light source.

The light emitted from the sample compartment is focused onto the sensors of the detection module by the use of at least one lens 808. This lens is a standard ×4 microscope objective with numerical aperture of 0.10 (Supplied by G. J. Carl Hansens Eftf., Denmark). The lens is arranged in such a way as to give an image of an object in the sample compartment on the sensors of the detection module which has approximately the same size as the original object (magnification approximately ×1).

In order to remove substantially any component from the light emitting from the sample compartment with wavelength below 575 nm from reaching the detection module, an optical filter 809 is inserted in the light path. This filter is of the type Schott OG590 (thickness 3 mm).

To further prevent infra-red radiation from reaching the detection system a heat absorbing filter 810 is placed in the light path. This filter is of the type Schott KG5 or KG3 (3 mm in thickness). This filter can be omitted if light emitting diodes are used as light source.

The filtered light from the sample compartment is detected by a charge couple device (CCD) 811 of the type GCA325KBL (supplied by L&G Semicon). The CCD is equipped with 510×492 detection elements.

The electrical information from the CCD is amplified and measured by an analogue to digital converter module 812 (ADC).

The operation of the instrument is controlled by the computer unit 813. The computer is a Motorola DSP56824 16 bit digital signal processor, equipped with non-volatile storage capacity for long time storage (EEPROM) as well as volatile storage capacity (RAM). The computer gathers information about the measured light intensity of each detection element of the CCD from the ADC module and uses it for the assessment of the number of somatic cells in the milk sample present in the sample compartment. The computer module is equipped with a real time clock.

The result of the assessment of the number of somatic cells in the milk sample is presented on a display 815 of type MDLS16166-3V (supplied by Varitronix).

The result of the assessment of the number of somatic cells in the milk sample can also be transmitted to an external computer (not shown) by the use of the output port 816.

The user of the instrument can control its operation, and enter relevant information through a collection of keys forming a key-pad 814. The key-pad is a 16 keys module of type ECO 16250 06 SP.

EXAMPLE 7

An Instrument for the Assessment of the Number of Bacteria in a Volume of Aqueous Sample FIG. 8 illustrates an instrument which can be used for the assessment of the number of bacteria in a volume of aqueous sample. The instrument is powered by either an external power source 801 or by an internal power source such as a lead acid (12V 2.2 Ah) rechargeable battery 803, manufactured by Wetronic Inc. (WE12-2.2).

The Power supply/battery charger 802 supplies the different units of the instrument. The power supply can use power from either the external or the internal power source, and is capable of switching between the two sources during operation. It is possible to reduce the power consumption when the instrument is in stand-by.

The assessment of the number of somatic cells is performed by detecting a fluorescence signal originating from a fluorochrome bounded to DNA within somatic cells present in the sample compartment 807. The sample compartment is defined by two substantially parallel planes of transmitting material thus forming a compartment with dimensions of about 10×10×0.7 mm (height, width, depth).

The fluorescence is generated by passing light of high energy (excitation light of wavelength 550 nm or less) through the sample compartment, with direction towards the detection module 811. The source 804 of the excitation light can be either a halogen lamp of type OSRAM-64255 (8V, 20 W Photo Optic Lamp) or a number of light emitting diodes, for instance 4 or more, of type NSPG-500S or NSPE-590S (Nichia Chemical Industries Ltd., Japan).

In order to remove substantially any component from the excitation light with wavelength above 550 nm from reaching the sample compartment, an optical filter 805 is inserted in the light path. This filter of the type Ferroperm SWP550, double sided interference filter on a 2 mm substrate (Hoya, CM-500) which absorbs infra-red radiation.

To further preventing infra-red radiation from reaching the sample compartment a heat absorbing filter 806 is placed in the light path. This filter is of the type Schott KG5 or KG3 (3 mm in thickness). This filter can be omitted if light emitting diodes are used as light source.

The light emitted from the sample compartment is focused onto the sensors of the detection module by the use of a lens 808. This lens can be a standard ×4 microscope objective with numerical aperture of 0.10 (Supplied by G. J. Carl Hansens Eftf., Denmark) or a standard ×10 microscope objective. The lens is arranged in such a way as to give an image of an object in the sample compartment on the sensors of the detection module which has approximately four to six times larger than the original object (magnification approximately between ×4 and ×6).

In order to remove substantially any component from the light emitting from the sample compartment with wavelength below 575 nm from reaching the detection module, an optical filter 809 is inserted in the light path. This filter of the type Schott OG590 (thickness 3 mm).

To further remove infra-red radiation from reaching the detection system a heat absorbing filter 810 is placed in the light path. This filter is of the type Schott KG5 or KG3 (3 mm in thickness). This filter can be omitted if light emitting diodes are used as light source.

The filtered light from the sample compartment is detected by a charge couple device (CCD) 811 of the type GCA325KBL (supplied by L&G Semicon). The CCD is equipped with 510×492 detection elements.

The electrical information from the CCD is amplified and measured by an analogue to digital converter module 812 (ADC).

The operation of the instrument is controlled by the computer unit 813. The computer is a Motorola DSP56824 16 bit digital signal processor, equipped with non-volatile storage capacity for long time storage (EEPROM) as well as volatile storage capacity (RAM). The computer gathers information about the measured light intensity of each detection element of the CCD from the ADC module and uses it for the assessment of the number of bacteria in a volume of aqueous sample present in the sample compartment. The computer module is equipped with a real time clock.

The result of the assessment of the number of bacteria in a volume of aqueous sample is presented on a display 815 of type MDLS16166-3V (supplied by Varitronix).

The result of the assessment of the number of bacteria in a volume of aqueous sample can also be transmitted to an external computer (not shown) by the use of the output port 816.

The user of the instrument can control its operation, and enter relevant information through a collection of keys forming a key-pad 814. The key-pad is a 16 keys module of type ECO 16250 06 SP.

EXAMPLE 8

The Assessment of the Number of Somatic Cells in a Volume of Milk According to the Present Invention Compared to the Results of a Routine Instrument The result of the assessment of the number of somatic cells in a volume of milk according the present invention was compared to the results obtained from a FossoMatic 400 routine instrument (Foss Electric, Denmark).

191 milk samples from individual cows, were measured on the FossoMatic instrument according to the instructions provided by the producers (Foss Electric, Denmark).

Upon the completion of the measurement on the FossoMatic a 1 ml (±2%) portion of the remaining sample was taken and mixed with 1 ml (±1%) of aqueous reagent solution, resulting in a milk solution containing 0.25% (w/v) Triton X-100 (t-Octylphenoxypolyethoxyethanol) and 25 µg/ml propidium iodide (CAS-25535-16-4).

The assessment of the number of somatic cells in a volume of milk was performed on an instrument according to the present invention, equipped with an excitation module comprising a halogen light source, OSRAM-64255 (8V, 20 W Photo Optic Lamp), an optical filter, Ferroperm SWP550 (double sided interference filter on a 2 mm substrate (Hoye, BG-39) which absorbs infra-red radiation) and a heat absorbing filter, (Schott KG5, 3 mm in thickness), and a detection module comprising a focusing lens, standard ×4 microscope objective with numerical aperture of 0.10, arranged in such a way as to give a magnification of approximately ×1 on the sensor elements, an optical filter, (Schott OG590, thickness 3 mm), and a heat absorbing filter, Schott KG5 (3 mm in thickness), and a CCD detector, SONY-CX 045 BL.

A portion of the milk solution was placed between two substantially parallel plates of glass, placed approximately in the focus plane of the detection module, and irradiated by excitation light emitted from the excitation module. The distance between the two parallel glass plates was approximately 100 µm. The volume being detected by the detection module, defined by the size of the CCD, the magnification used, and the distance between the parallel glass plates was equivalent to approximately 1 µl, thus containing approximately 0.5 µl of milk.

The sample compartment was a stationary flow cell. The milk solution was placed into the sample compartment by the use of a peristaltic pump, situated down-stream from the sample compartment. In order to reduce the movement of the sample inside the flow cuvette a valve was placed in the flow system, immediately adjacent to the sample compartment.

Each observation was based on the measurement of two portions of the milk solution. The two measurement were treated in such manner that the second measurement was numerically subtracted from the first measurement discarding all values having negative result by assigning zero these values. The number of somatic cells represented in each observation was determined by identifying and counting the number of "peaks" in the resulting observation.

The assessment of the number of somatic cells in a volume of milk was presented as the number of counted peaks in two observations from the same sample solution, thus presented as the number of somatic cells per 1 µl of milk.

Figure 9:
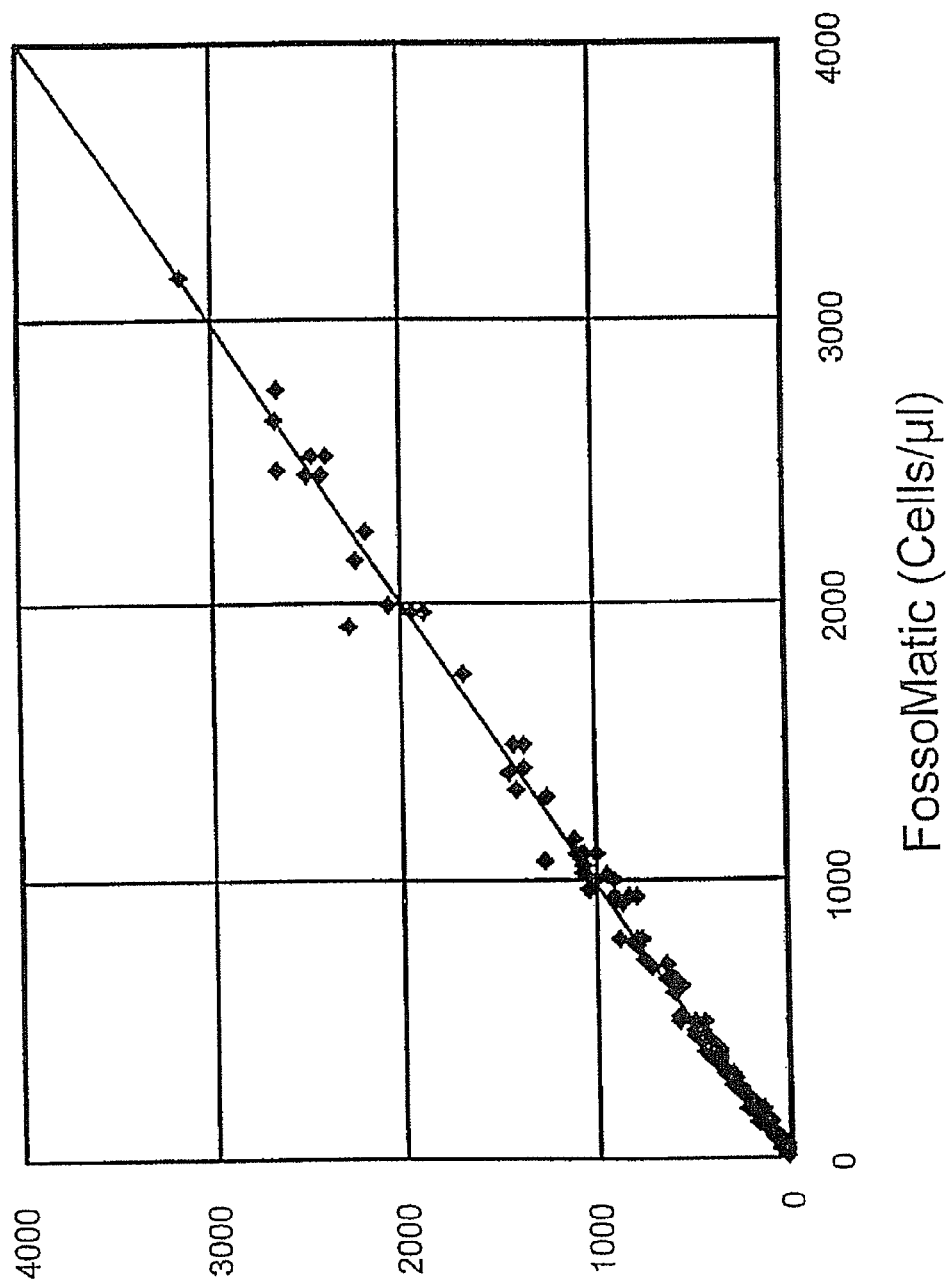
FIG. 9 is a graph of the assessment of the number of somatic cells in 1 µl of milk plotted against results obtained by a FossoMatic routine instrument.
Figure 9:
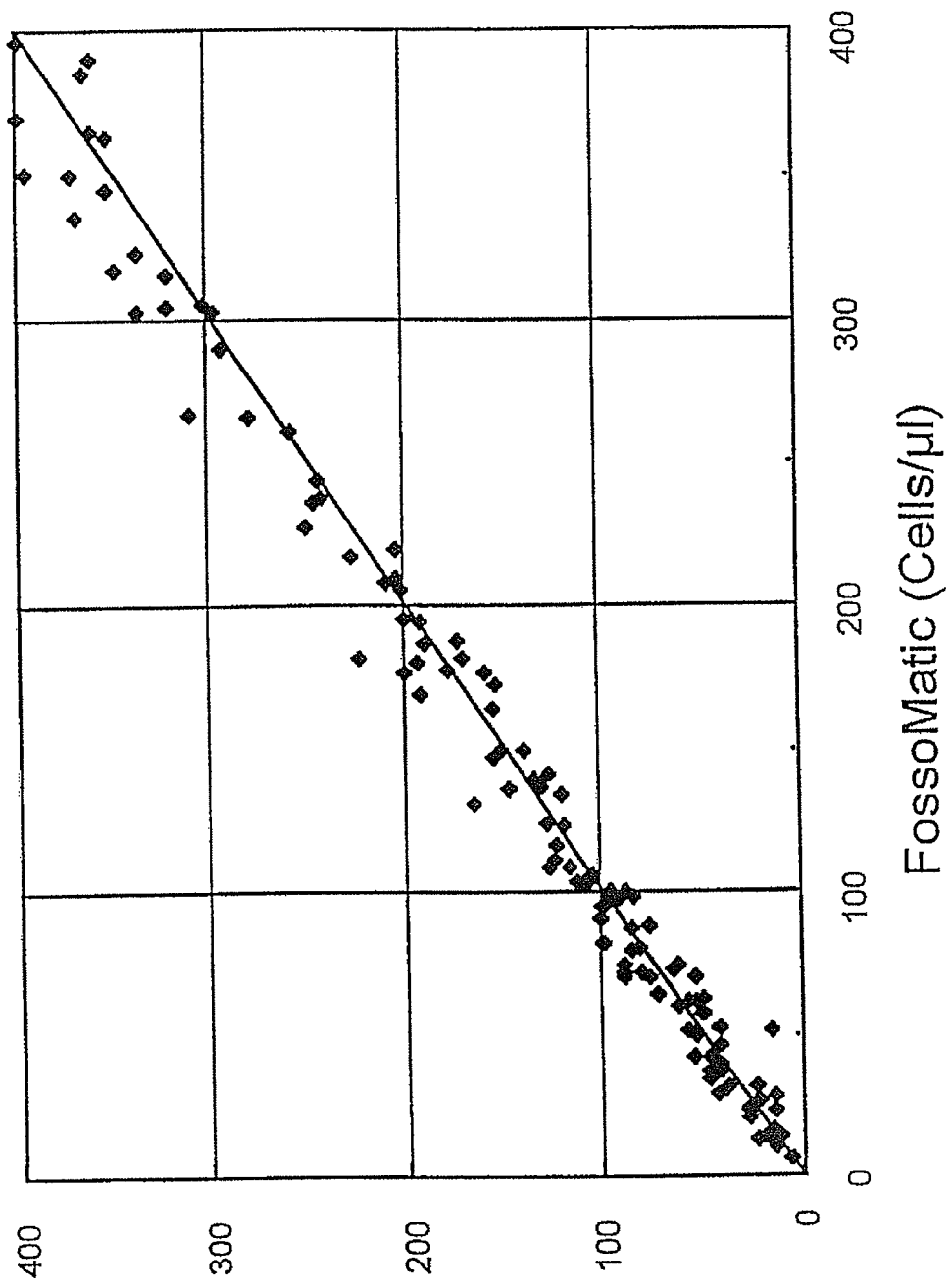

The results obtained by the two methods are given in FIG. 9 as a graph of the assessment according to the present invention (labelled "Cell Counter") vs. results obtained by the FossoMatic instrument. FIG. 9A shows the graph of the result of the 191 samples. FIG. 9B shows the result obtained when considering those samples having an estimated number of somatic cells of less than 400 cells/µl.

Conclusion

The conclusion from the test described above as shown in FIG. 9 is that the assessment of the number of somatic cells in milk according to the present invention is generally in good agreement to the results obtained by the FossoMatic instrument.

EXAMPLE 9

The Effect of the Concentration of Fluorochrome on the Assessment of Biological Particles in a Scattering Biological Sample Material According to the Present Invention When performing the assessment of biological particles in biological sample material according to the present invention it is often of interest to maximise the volume of the sample solution being analysed. This can for instance be accomplished by increasing the depth of the sample being analysed.

Apart from any limitation by effective focusing depth can imply the scattering or attenuating property of the sample being analysed can limit the effective depth of the sample.

When analysing samples containing a high number of particles or other constituents being capable of causing scattering or other attenuation of any signal being measured this can limit the effective depth of the sample. The cause of this can be that any signal originating from a particle situated relatively deep in the sample is attenuated while trawling towards the boundaries of the sample.

One such sample material is milk. Milk contains both a high number of fat globules and protein micelles. As a result of this milk is a highly scattering media.

When assessing the number of somatic cells in a volume of milk by the use of a method based on the measurement of a fluorescence signal from the sample the scattering properties of the milk can limit the effective depth of the sample being analysed. This is partly due to the attenuation of any signal originating from cells situated deep in the sample but also due to the fact that the variations in the background signal, caused by any fluorochrome molecules on free form, increases, thus making it more difficult to identify the signals originating from the somatic cells.

The present example illustrates the effect of the concentration of the fluorochrome on the number of somatic cells which can be identified in a milk sample. The sample was a single cow sample, preserved with bronopol. The estimated number of somatic cells in the sample suggested that between 1150 and 1200 objects should be counted under the present conditions.

The sample was measured in a measuring cell consisting of two substantially parallel glass plates, separated by a distance of about 100 µm, representing the depth of the sample. Two measurement of different portions of the sample were taken and the resulting image was constructed by subtracting the later measurement from the first measurement and then multiplying those results which were negative by the value −1 thus producing a final image consisting entirely of values larger than or equal to 0.

Reagents were added to the milk sample, amounting to about 5% of the volume of the sample being analysed (resulting in an effective thickness of the milk equivalent to about 95 µm). The reagents contained Triton X100 (t-Octylphenoxypolyethoxyethanol) resulting in a final concentration of 0.24% (w/v) and Propidium Iodide (CAS-25535-16-4) as fluorochrome resulting in final concentrations ranging between 89 and 2.4 µg/ml.

To compensate for the reduced signal due to the decreasing concentration of Propidium Iodide the electronical gain of the detection system was adjusted accordingly.

Figure 10:
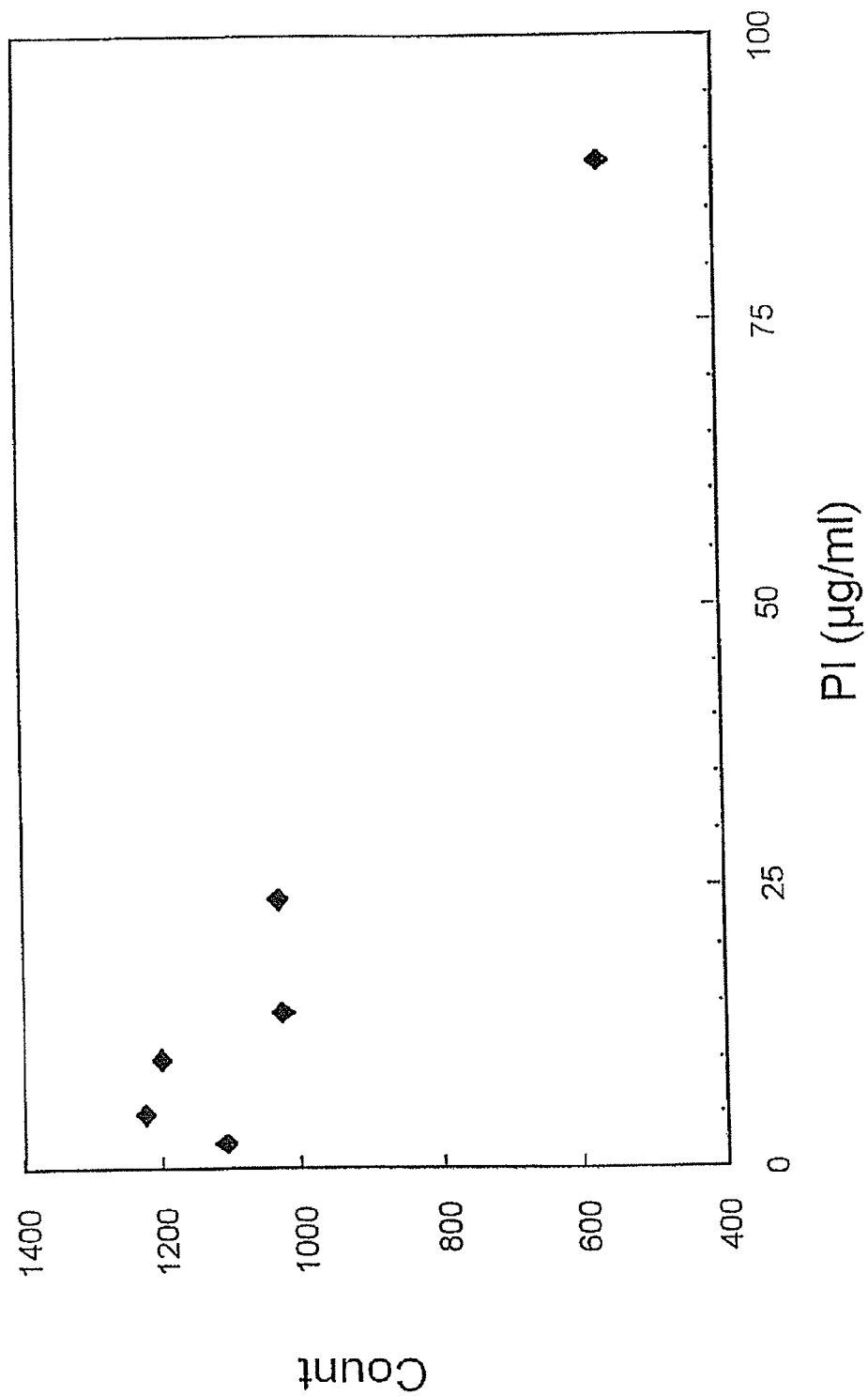
FIG. 10 is a graph of the number of counted objects in a milk sample vs. the concentration of the fluorochrom.

The result of the experiment is given in FIG. 10 which shows a graph of the number of objects which were counted vs. the concentration of the Propidium Iodide.

Conclusion

The conclusion from the investigation as described above is that when measuring samples having scattering properties, it can be possible to extend the depth of the sample being analysed by reducing the concentration of the fluorochrome.

EXAMPLE 10

Processing of a Two Dimensional Image

The result of a measurement of signals from particles by an array of detection elements, such as a charged coupled deceive (CCD), for instance SONY-CX 045 BL, according to the present invention, can be visualised as a two dimensional image where the intensity of each detection element can be represented by a density or a colour.

Figure 11:
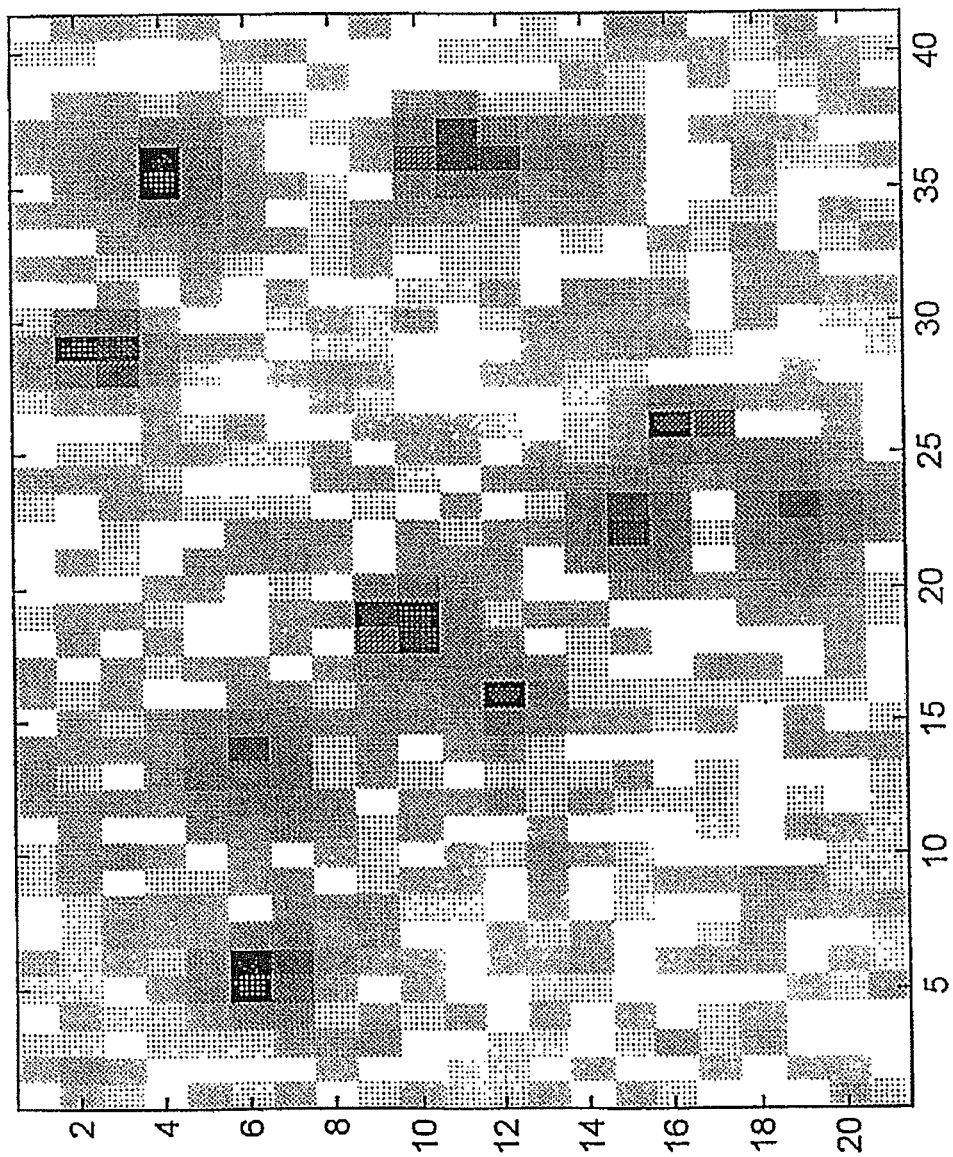
FIG. 11 illustrates the effect of processing two dimensional image.
Figure 11:
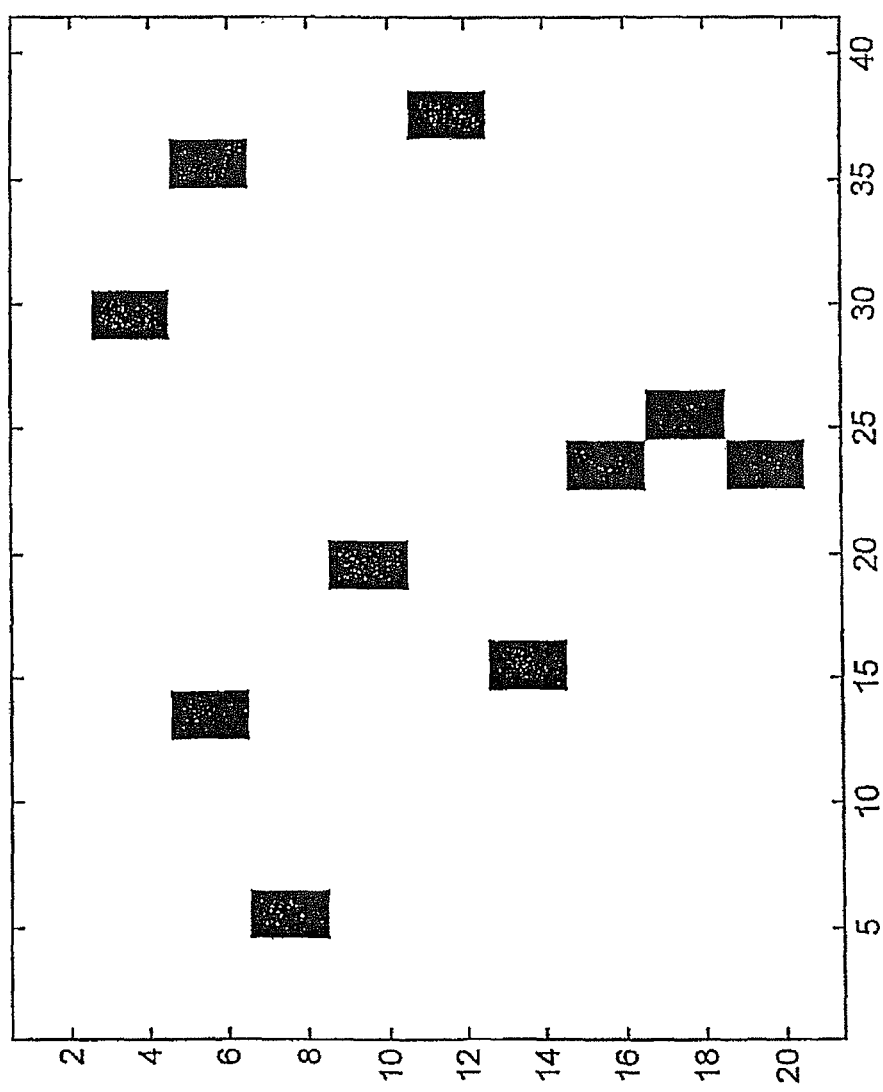

FIG. 11A gives a presentation of a segment of an image from a measurement of somatic cells in milk. The intensities on which FIG. 11A is based is given in Table 1 below. In FIG. 11 the intensity is represented by shades of grey, such that low intensity has a lighter shade and high intensity has a darker shade.

Assuming that each somatic cell gives rise to an image which has the size of approximately 2×2 detection elements we can estimate the number of somatic cells being represented in FIG. 11A to be approximately 10.

The task of having a computer determining the number of particles being represented in a measurement involves the construction of a set of rules or instructions for the computer, which when applied to the result of a measurement gives an estimate of the number objects.

One such simple rule could be to identify the number of detection elements which have intensity above a given threshold value. Assuming that each object on average is represented by an intensity in a given number of detection elements the number of identified detection element can be adjusted to give an estimate of the number of objects. Such a method is dependent on that an approximately correct estimate of the size of the image of an object is available.

In the following a pre-processing of the image is presented which makes the previous method of assessment less dependent on the size of an image of an object. The effect of the processing is to concentrate the intensity information in a given region of the image to substantially one number.

a) The first step of the processing is to define a region which has a size which is at least the same as the size of the image of an object which is to be detected. In the present example this region is of the size 5×5 detection elements but regions of different size can be used depending on the nature of the image of the object being analysed. This region is placed in the two dimensional co-ordinate system defined by the detection elements. In this example this region is initially placed in the upper left corner of the co-ordinate system. For each of such region a data value is defined which will hold the value representing the region.

The next step is to adjust the value of the data element representing the region. This is done by firstly by considering the intensity gradient around the centre of the region and secondly by considering the intensities of the detection elements positioned adjacent to the centre of the region. It is possible to interchange the order of these steps. This produces different result, depending on the order chosen.

b) The investigation of the gradient around the centre of the region is based on investigating the intensity values of at least two detection elements. In the present example we estimate the intensity values of three detection elements including the detection element situated in the centre of the region. A total of 8 gradients originating at the centre of the region and with a direction horizontal, vertical or diagonal relative to the centre of the region.

Assuming the identification of detection elements as follows, where the centre of the region is identified as A:

|   | 1 | 2 | 3 | 4 | 5 |
|---|---|---|---|---|---|
| 1 | I | — | B | — | C |
| 2 | — | $I_o$ | $B_o$ | $C_o$ | — |
| 3 | H | $H_o$ | A | $D_o$ | D |
| 4 | — | $G_o$ | $F_o$ | $E_o$ | — |
| 5 | G | — | F | — | E |

The eight different gradients are defined by the following detection elements: [A,$B_o$,B], [A,$C_o$,C], [A,$D_o$,D], [A,$E_o$,E], [A,$F_o$,F], [A,$G_o$,G], [A,$H_o$,H], [A,$I_o$,I].

The value representing the region can be adjusted in different way depending on the result of the gradient testing. In the present example the value is adjusted to zero if one of the following gradient test is true, defined as following:

The value of the region is zero if ((A<B AND A<$B_o$) OR (A<C AND A<$C_o$) OR (A<D AND A<$D_o$) OR (A<E AND A<$E_o$) OR (A<F AND A<$F_o$) OR (A<=G AND A<$G_o$) OR) (A<=H AND A<$H_o$) OR (A<I AND A<$I_o$)) is true The value of the region can either be stored separately for the region or it can be used to replace the value of the detection element identified as A. In the present example the value of the region is used to replace the value of A and will be used as intensity value of the detection element in subsequent analysis.

When the previous step has been completed a new range according to a) is defined. The new range is placed on a different position of the image. In the present example the position of the new range is defined by moving the range down a column by two rows. When the end of the column has been reached the next range is position by moving to the first row and two columns to the right. The range is moved in this way until substantially the entire image has been investigated.

c) When substantially the entire image has been investigated according to b), the second step in defining a value representing the region involves adjusting the value of each range based on the detection elements which are situated immediately adjacent to the centre value of the region. In the present example this is done by assigning the result of the following expressions to the value of each range:

A=if(A>=B & A>=H AND A>=I & A>=C & A>=D) then max(A,$B_o$) else A)

A=if(A>=B & A>=C & A>=D) then max(A,$C_o$) else A)

A=if(A>=D & A>=B & A>=C & A>=E & A>=F) then max(A,$D_o$) else A)

A=if(A>D & A>E & A>F) then max(A,$E_o$) else A)

A=if(A>=F & A>D & A>E & A>G & A>H) then max(A, $F_o$) else A)

A=if(A>F & A>G & A>H) then max(A,$G_o$) else A)

A=if(A>=H & A>F & A>G & A>I & A>B) then max(A, $H_o$) else A)

A=if(A>H & A>I & A>G) then max(A,$I_o$) else A)

Value=A ("&" represents the logical operation AND)

When the previous step has been completed a new range is defined preferably in the same manner as was done previously.

The results of processing the data in Table 1 and FIG. 11A according to the method outlined above is given in Table 2 below and in FIG. 11B.

When both steps b) and c) have been completed for substantially the entire range of detection elements the estimation of the number of objects being represented in the image can be done on the bases of the values estimated for each range.

The image of each object which signal is represented in a range of detection elements which is of comparable size to the ranges being used for the processing, or smaller, will substantially result in only one value when both steps b) and c) have been completed for substantially the entire range of detection elements. This makes it possible to estimate the total number of objects represented in an image by comparing the value of each of the ranges to give a threshold value since each object is substantially only represented in one value.

TABLE 1

|  |  |  | | 1 | | 2 | | 3 | | 4 | | 5 | | 6 | | 7 | | 8 | | 9 | | 10 | |
|---|---|---|---|---|---|---|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|  | 1 | 1 | 8 | 4 | 1 | 5 | 11 | 2 | 2 | 5 | 4 | 2 | 9 | 17 | 12 | 3 | 6 | 14 | 2 | 5 | 2 | 2 | 1 |
|  | 2 | 8 | 12 | 5 | 6 | 4 | 5 | 4 | 4 | 10 | 10 | 8 | 9 | 4 | 7 | 9 | 5 | 3 | 9 | 6 | 2 | 8 | 2 |
| 1 | 3 | 5 | 6 | 3 | 5 | 2 | 8 | 12 | 9 | 2 | 16 | 3 | 12 | 2 | 6 | 5 | 8 | 9 | 2 | 8 | 3 | 5 | 4 |
|  | 4 | 3 | 3 | 4 | 4 | 8 | 5 | 8 | 8 | 4 | 7 | 3 | 7 | 9 | 8 | 11 | 2 | 5 | 7 | 5 | 6 | 2 | 1 |
| 2 | 5 | 6 | 3 | 5 | 7 | 21 | 15 | 8 | 6 | 5 | 3 | 9 | 9 | 49 | 29 | 20 | 3 | 7 | 3 | 3 | 7 | 9 | 2 |
|  | 6 | 5 | 2 | 4 | 16 | 171 | 179 | 22 | 2 | 6 | 6 | 7 | 34 | 71 | 132 | 53 | 12 | 10 | 3 | 3 | 2 | 12 | 13 |
| 3 | 7 | 6 | 3 | 11 | 17 | 81 | 109 | 31 | 14 | 14 | 2 | 15 | 20 | 41 | 38 | 25 | 10 | 3 | 7 | 6 | 5 | 12 | 9 |
|  | 8 | 3 | 6 | 11 | 4 | 10 | 18 | 7 | 12 | 3 | 6 | 10 | 14 | 5 | 4 | 14 | 4 | 7 | 2 | 13 | 2 | 8 | 13 |
| 4 | 9 | 4 | 2 | 12 | 8 | 2 | 6 | 9 | 9 | 5 | 5 | 5 | 3 | 11 | 9 | 12 | 9 | 20 | 83 | 165 | 22 | 3 | 2 |
|  | 10 | 8 | 2 | 2 | 5 | 8 | 7 | 2 | 4 | 6 | 2 | 6 | 7 | 5 | 2 | 14 | 8 | 30 | 167 | 171 | 53 | 7 | 9 |
| 5 | 11 | 5 | 4 | 3 | 10 | 1 | 1 | 2 | 5 | 8 | 6 | 3 | 6 | 2 | 7 | 10 | 23 | 30 | 31 | 18 | 10 | 7 | 5 |
|  | 12 | 4 | 5 | 5 | 1 | 3 | 6 | 7 | 2 | 1 | 4 | 2 | 15 | 4 | 10 | 43 | 169 | 25 | 10 | 5 | 6 | 11 | 6 |
| 6 | 13 | 7 | 1 | 4 | 7 | 4 | 8 | 5 | 8 | 11 | 14 | 7 | 5 | 4 | 5 | 12 | 33 | 14 | 3 | 11 | 3 | 2 | 9 |
|  | 14 | 3 | 7 | 2 | 3 | 5 | 13 | 8 | 3 | 2 | 7 | 2 | 10 | 4 | 2 | 6 | 5 | 5 | 4 | 10 | 1 | 22 | 39 |
| 7 | 15 | 8 | 3 | 4 | 7 | 2 | 2 | 2 | 4 | 5 | 4 | 3 | 4 | 11 | 2 | 7 | 4 | 2 | 6 | 2 | 15 | 74 | 162 |
|  | 16 | 4 | 2 | 14 | 2 | 2 | 7 | 2 | 3 | 7 | 3 | 1 | 5 | 2 | 1 | 5 | 4 | 1 | 2 | 2 | 15 | 40 | 60 |
| 8 | 17 | 2 | 6 | 5 | 4 | 3 | 9 | 5 | 3 | 8 | 2 | 5 | 5 | 4 | 3 | 8 | 5 | 12 | 3 | 3 | 6 | 1 | 4 |
|  | 18 | 2 | 2 | 9 | 8 | 2 | 11 | 9 | 10 | 9 | 1 | 2 | 3 | 3 | 3 | 2 | 5 | 7 | 2 | 12 | 11 | 19 | 37 |
| 9 | 19 | 1 | 6 | 3 | 2 | 7 | 2 | 3 | 8 | 10 | 2 | 11 | 5 | 3 | 12 | 7 | 5 | 2 | 3 | 7 | 18 | 30 | 69 |
|  | 20 | 10 | 6 | 2 | 2 | 5 | 6 | 1 | 7 | 4 | 5 | 7 | 1 | 1 | 7 | 2 | 5 | 8 | 8 | 8 | 11 | 7 | 30 |
|  | 21 | 5 | 2 | 2 | 3 | 13 | 4 | 4 | 11 | 4 | 4 | 5 | 5 | 4 | 8 | 4 | 3 | 3 | 2 | 4 | 4 | 1 | 11 |

|  |  | | 11 | | 12 | | 13 | | 14 | | 15 | | 16 | | 17 | | 18 | | 19 | | | |
|---|---|---|---|---|---|---|---|---|---|---|---|---|---|---|---|---|---|---|---|---|---|---|
|  |  | 23 | 24 | 25 | 26 | 27 | 28 | 29 | 30 | 31 | 32 | 33 | 34 | 35 | 33 | 37 | 38 | 39 | 40 | 41 |
|  | 1 | 4 | 11 | 3 | 3 | 5 | 16 | 13 | 5 | 1 | 8 | 2 | 7 | 1 | 6 | 7 | 3 | 2 | 5 | 2 |
|  | 2 | 3 | 7 | 4 | 2 | 8 | 57 | 172 | 33 | 2 | 10 | 2 | 10 | 11 | 13 | 9 | 6 | 1 | 5 | 8 |
| 1 | 3 | 6 | 7 | 4 | 3 | 7 | 93 | 166 | 53 | 6 | 4 | 9 | 8 | 30 | 16 | 11 | 9 | 2 | 1 | 6 |
|  | 4 | 8 | 4 | 7 | 6 | 8 | 20 | 20 | 6 | 3 | 4 | 7 | 25 | 171 | 175 | 29 | 5 | 2 | 1 | 4 |
| 2 | 5 | 5 | 3 | 8 | 5 | 3 | 4 | 9 | 1 | 6 | 9 | 13 | 24 | 69 | 63 | 20 | 7 | 3 | 2 | 8 |
|  | 6 | 5 | 2 | 4 | 9 | 3 | 2 | 10 | 3 | 3 | 5 | 13 | 12 | 14 | 6 | 6 | 5 | 5 | 8 | 1 |
| 3 | 7 | 4 | 2 | 5 | 1 | 2 | 6 | 2 | 5 | 7 | 1 | 9 | 2 | 6 | 3 | 2 | 4 | 2 | 10 | 3 |
|  | 8 | 2 | 11 | 10 | 2 | 6 | 14 | 4 | 6 | 3 | 5 | 4 | 4 | 5 | 2 | 5 | 2 | 6 | 3 | 3 |
| 4 | 9 | 5 | 9 | 3 | 8 | 4 | 8 | 5 | 4 | 1 | 6 | 8 | 10 | 2 | 6 | 6 | 2 | 3 | 1 | 6 |
|  | 10 | 2 | 4 | 6 | 6 | 2 | 2 | 3 | 10 | 4 | 2 | 4 | 11 | 21 | 83 | 44 | 9 | 2 | 3 | 3 |
| 5 | 11 | 9 | 3 | 9 | 8 | 3 | 1 | 3 | 1 | 4 | 5 | 4 | 6 | 68 | 164 | 164 | 19 | 2 | 4 | 2 |
|  | 12 | 1 | 11 | 3 | 4 | 2 | 8 | 3 | 4 | 9 | 4 | 4 | 5 | 33 | 123 | 54 | 4 | 2 | 5 | 1 |
| 6 | 13 | 5 | 9 | 8 | 1 | 1 | 8 | 7 | 9 | 3 | 3 | 1 | 11 | 11 | 38 | 17 | 5 | 3 | 4 | 5 |
|  | 14 | 35 | 9 | 4 | 5 | 4 | 4 | 6 | 6 | 13 | 2 | 5 | 11 | 21 | 41 | 11 | 4 | 7 | 5 | 3 |
| 7 | 15 | 125 | 20 | 7 | 6 | 6 | 4 | 10 | 7 | 10 | 2 | 1 | 6 | 7 | 10 | 12 | 5 | 5 | 7 | 12 |
|  | 16 | 44 | 10 | 36 | 169 | 40 | 3 | 13 | 8 | 11 | 4 | 7 | 3 | 3 | 3 | 2 | 2 | 3 | 7 | 13 |
| 8 | 17 | 3 | 7 | 31 | 87 | 25 | 3 | 4 | 3 | 3 | 3 | 4 | 5 | 1 | 2 | 6 | 1 | 7 | 6 | 2 |
|  | 18 | 57 | 25 | 23 | 1 | 11 | 3 | 1 | 10 | 11 | 8 | 12 | 4 | 8 | 14 | 6 | 4 | 3 | 4 | 4 |
| 9 | 19 | 91 | 25 | 16 | 2 | 7 | 7 | 3 | 2 | 9 | 6 | 1 | 3 | 2 | 4 | 7 | 1 | 5 | 9 | 12 |
|  | 20 | 42 | 8 | 9 | 6 | 11 | 1 | 2 | 4 | 6 | 2 | 4 | 6 | 3 | 4 | 2 | 8 | 10 | 6 | 2 |
|  | 21 | 13 | 10 | 3 | 3 | 2 | 3 | 4 | 5 | 6 | 2 | 6 | 5 | 2 | 8 | 2 | 9 | 3 | 4 | 3 |

TABLE 2

|  |  |  | | 1 | | 2 | | 3 | | 4 | | 5 | | 6 | | 7 | | 8 | | 9 | | 10 | |
|---|---|---|---|---|---|---|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|  | 1 |  |  |  |  |  |  |  |  |  |  |  |  |  |  |  |  |  |  |  |  |  |  |
|  | 2 |  |  |  |  |  |  |  |  |  |  |  |  |  |  |  |  |  |  |  |  |  |  |
| 1 | 3 |  |  | 0 |  | 0 |  | 12 |  | 0 |  | 0 |  | 0 |  | 0 |  | 9 |  | 0 |  | 6 |  |
|  | 4 |  |  |  |  |  |  |  |  |  |  |  |  |  |  |  |  |  |  |  |  |  |  |
| 2 | 5 |  |  | 4 |  | 0 |  | 0 |  | 7 |  | 0 |  | 132 |  | 0 |  | 0 |  | 0 |  | 0 |  |
|  | 6 |  |  |  |  |  |  |  |  |  |  |  |  |  |  |  |  |  |  |  |  |  |  |
| 3 | 7 |  |  | 0 |  | 179 |  | 14 |  | 6 |  | 0 |  | 0 |  | 12 |  | 10 |  | 0 |  | 13 |  |
|  | 8 |  |  |  |  |  |  |  |  |  |  |  |  |  |  |  |  |  |  |  |  |  |  |
| 4 | 9 |  |  | 12 |  | 0 |  | 12 |  | 6 |  | 14 |  | 9 |  | 14 |  | 0 |  | 171 |  | 0 |  |
|  | 10 |  |  |  |  |  |  |  |  |  |  |  |  |  |  |  |  |  |  |  |  |  |  |
| 5 | 11 |  |  | 0 |  | 7 |  | 0 |  | 8 |  | 7 |  | 7 |  | 23 |  | 0 |  | 0 |  | 0 |  |
|  | 12 |  |  |  |  |  |  |  |  |  |  |  |  |  |  |  |  |  |  |  |  |  |  |
| 6 | 13 |  |  | 7 |  | 8 |  | 0 |  | 14 |  | 15 |  | 10 |  | 169 |  | 0 |  | 11 |  | 0 |  |
|  | 14 |  |  |  |  |  |  |  |  |  |  |  |  |  |  |  |  |  |  |  |  |  |  |
| 7 | 15 |  |  | 7 |  | 13 |  | 0 |  | 0 |  | 0 |  | 11 |  | 7 |  | 0 |  | 0 |  | 0 |  |
|  | 16 |  |  |  |  |  |  |  |  |  |  |  |  |  |  |  |  |  |  |  |  |  |  |
| 8 | 17 |  |  | 2 |  | 7 |  | 3 |  | 0 |  | 5 |  | 0 |  | 8 |  | 12 |  | 15 |  | 0 |  |
|  | 18 |  |  |  |  |  |  |  |  |  |  |  |  |  |  |  |  |  |  |  |  |  |  |
| 9 | 19 |  |  | 0 |  | 11 |  | 0 |  | 10 |  | 11 |  | 0 |  | 7 |  | 0 |  | 11 |  | 0 |  |
|  | 20 |  |  |  |  |  |  |  |  |  |  |  |  |  |  |  |  |  |  |  |  |  |  |
|  | 21 |  |  |  |  |  |  |  |  |  |  |  |  |  |  |  |  |  |  |  |  |  |  |

TABLE 2-continued

|  |  | 11 | | 12 | | 13 | | 14 | | 15 | | 16 | | 17 | | 18 | | 19 | | |
|---|---|---|---|---|---|---|---|---|---|---|---|---|---|---|---|---|---|---|---|---|
|  |  | 23 | 24 | 25 | 26 | 27 | 28 | 29 | 30 | 31 | 32 | 33 | 34 | 35 | 36 | 37 | 38 | 39 | 40 | 41 |
|  | 1 |  |  |  |  |  |  |  |  |  |  |  |  |  |  |  |  |  |  |  |
|  | 2 |  |  |  |  |  |  |  |  |  |  |  |  |  |  |  |  |  |  |  |
| 1 | 3 | 7 |  | 0 |  | 0 |  | 172 |  | 0 |  | 0 |  | 0 |  | 0 |  | 0 |  |  |
|  | 4 |  |  |  |  |  |  |  |  |  |  |  |  |  |  |  |  |  |  |  |
| 2 | 5 | 0 |  | 9 |  | 0 |  | 0 |  | 4 |  | 0 |  | 175 |  | 7 |  | 0 |  |  |
|  | 6 |  |  |  |  |  |  |  |  |  |  |  |  |  |  |  |  |  |  |  |
| 3 | 7 | 0 |  | 11 |  | 6 |  | 0 |  | 7 |  | 0 |  | 0 |  | 5 |  | 0 |  |  |
|  | 8 |  |  |  |  |  |  |  |  |  |  |  |  |  |  |  |  |  |  |  |
| 4 | 9 | 0 |  | 0 |  | 14 |  | 0 |  | 0 |  | 10 |  | 5 |  | 5 |  | 0 |  |  |
|  | 10 |  |  |  |  |  |  |  |  |  |  |  |  |  |  |  |  |  |  |  |
| 5 | 11 | 9 |  | 9 |  | 2 |  | 10 |  | 5 |  | 11 |  | 0 |  | 164 |  | 0 |  |  |
|  | 12 |  |  |  |  |  |  |  |  |  |  |  |  |  |  |  |  |  |  |  |
| 6 | 13 | 0 |  | 0 |  | 0 |  | 8 |  | 4 |  | 11 |  | 0 |  | 0 |  | 0 |  |  |
|  | 14 |  |  |  |  |  |  |  |  |  |  |  |  |  |  |  |  |  |  |  |
| 7 | 15 | 162 |  | 5 |  | 0 |  | 10 |  | 13 |  | 11 |  | 0 |  | 41 |  | 0 |  |  |
|  | 16 |  |  |  |  |  |  |  |  |  |  |  |  |  |  |  |  |  |  |  |
| 8 | 17 | 0 |  | 169 |  | 0 |  | 0 |  | 0 |  | 5 |  | 0 |  | 0 |  | 7 |  |  |
|  | 18 |  |  |  |  |  |  |  |  |  |  |  |  |  |  |  |  |  |  |  |
| 9 | 19 | 91 |  | 0 |  | 3 |  | 0 |  | 11 |  | 4 |  | 0 |  | 14 |  | 0 |  |  |
|  | 20 |  |  |  |  |  |  |  |  |  |  |  |  |  |  |  |  |  |  |  |
|  | 21 |  |  |  |  |  |  |  |  |  |  |  |  |  |  |  |  |  |  |  |

EXAMPLE 11

Assessment of the Number of Bacteria in an Aqueous Sample

Using the instrument described in example 7 the number of bacteria in an aqueous sample was assessed according to the present invention. The experiment was conducted as follows:

Glucose, in the amount of 0.3 g, was added to a portion of 30 ml of Buffered Peptone Water (LAB03627, Bie & Berntsen, Denmark). This broth was inoculated with 100 µl of a raw milk sample containing a natural bacterial microflora. After inoculation the broth was incubated for 24 hours at approximately 30° C.

Following incubation the broth was strongly turbid. Empirically such a culture contains from $1\times10^9$ to $2\times10^9$ colony forming units per ml.

A 25 µl portion of the incubated broth was transferred to 1 ml of an aqueous reagent solution containing 0.13% Triton X-100, 13 µg/ml propidium iodide and 0.5% ethylenediaminetetraacetic acid (EDTA, Sigma E 4884).

After mixing a portion of the broth/reagent solution was placed between two substantially parallel glass plates, placed approximately in the focus plane of the detection module, and irradiated by excitation light emitted from the excitation module.

The distance between the two parallel glass plates was approximately 100 µm. The volume being detected by the detection module, defined by the size of the CCD, the magnification used, and the distance between the parallel glass plates was equivalent to approximately 0.04 µl, thus containing approximately 0.001 µl of the incubated broth.

Two measurements of different portions of the sample were taken. The result from the second measurement was subtracted from the first measurement, transforming those values which are below zero to zero by the formula: $Signal_{(ij)} = MAX((meas1_{(ij)} - meas2_{(ij)}), 0)$.

Results

Figure 12:
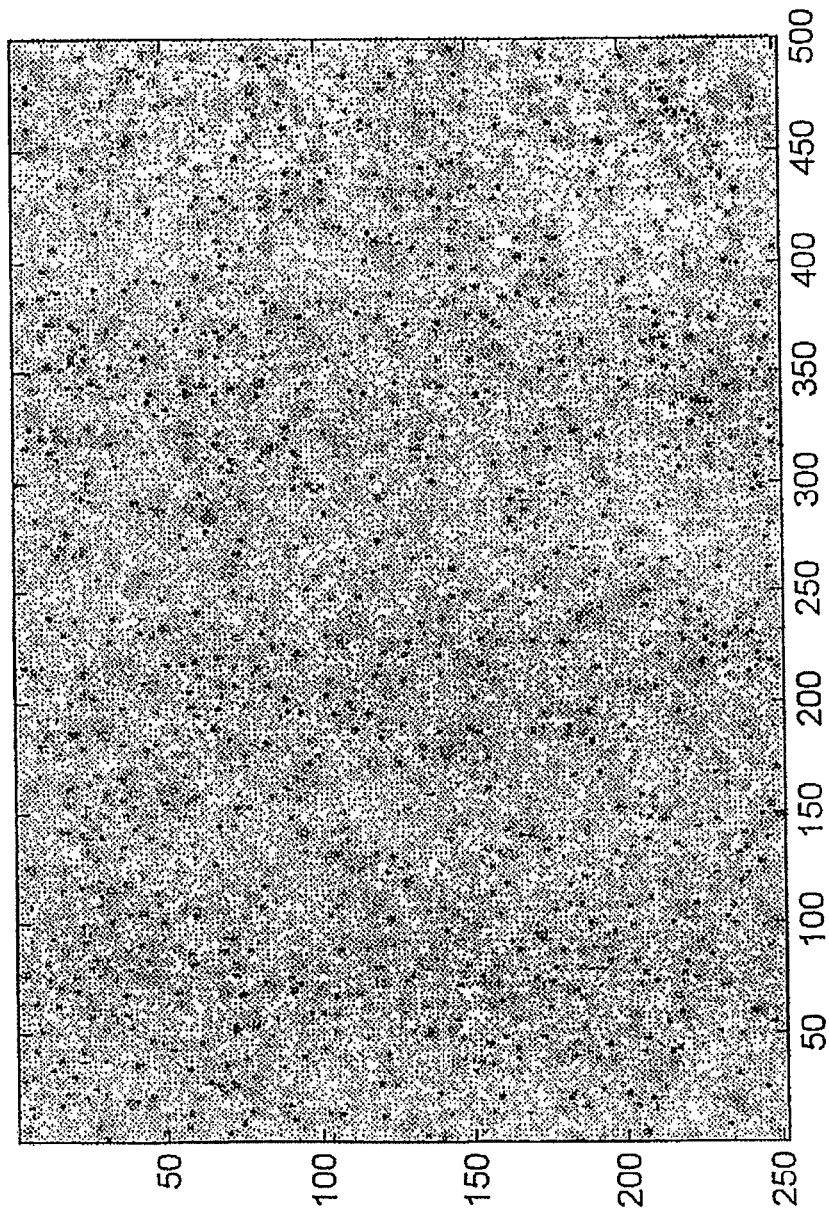
FIG. 12 illustrates the representations of intensities in the measurement of bacteria in an aqueous sample.

The result from the subtraction of the intensities from the two measurements as described above, is represented in FIG. 12. The result from the subtraction of intensities are presented by converting the resulting value for each detection element to the shade of grey, the light shads representing low intensities and the dark shads representing high intensities.

The number of objects represented in the measurement was counted according to a method of the present invention, as described in Example 10 resulted in an assessment of the number of bacteria in the sample volume was 1601.

The number of counts in one observation was expected to be in the range of 1000 to 2000. Thus it is reasonable to conclude that the instrument described in example 7 is able to assess the number of bacteria in an a aqueous sample.

DETAILED DESCRIPTION OF EMBODIMENTS

While a number of preferred embodiments have been described above, the present invention can be performed and exploited in a large number of ways. In the following, a discussion of a number of measures and details relevant to the invention is given, comprising both preferred embodiments and embodiments which illustrate possibilities of working the invention. Some of the embodiments are given as numbered items, to be understood as brief indications of possible and preferred embodiments in the light of the remaining claims and description herein.

Detection Elements

In the method of the present invention, the assessment of biological particles in a volume of liquid sample material is made by arranging a sample of the liquid sample material in a sample compartment having a wall defining an exposing area, transparent to electromagnetic signals emitted from the sample being exposed to the exterior, and forming an image of electromagnetic signals from the sample in the sample compartment on an array of detection elements, and processing the image formed on the array of detection elements in such a manner that signals from the biological particles are identified as distinct from the sample background, and based on the signals from the biological particles identified assessing biological particles in a volume of liquid sample material.

In the present specification and claims, the term "biological particle" designates a particle originating from, or found in living matter, such as somatic cells, red blood cells, blood platelets, bacteria, yeast cells, fragments of cells, lipid globules, protein micelles, plankton, algae or fraction thereof.

In the present specification and claims, the term "biological sample material" designates a liquid sample material of, often biological origin, or material where biological particles might be found, such as: specimen of human origin, specimen of animal origin, drinking water, waste water, process water, sea water, lake water, river water, ground water, food, feed or components of food and feed, milk or a milk product, blood or a blood product, urine, faeces, saliva, specimen from an inflammation, specimen from the petrochemical industry, specimen from the pharmaceutical industry, specimen from the food or feed industry, or product thereof.

The method allows a sample of the sample material to be analysed when practically all components in the sample material are present in the sample during the measurement on which the assessment is based. This is often practical when the liquid sample material is a biological sample material, since it is often associated with considerable difficulties to selectively remove one, or several, or substantially every component from a sample of sample material prior to analysis.

Detection Array

The array of detection elements can be arranged in such a way that they form a substantially straight line. When using a high number of detection elements they can be arranged in two directions in such a way that the detection elements form a series of substantially parallel straight lines, and often the array of detection elements is arranged in one plane. This plane of detection elements is often arranged parallel to an inner boundary of the sample compartment.

Signal Conditioning—Hardware

The signal detected by the detection elements is normally an electromagnetic radiation and it is therefore preferable to have methods to transform those signals to measurable signal, such as voltage, or electrical current. Many such signals have a varying background signal, or bias, and it is therefore preferable to have methods which at least partly can eliminate those effects. This can often be accomplished by using a signal in one or several neighbouring detection elements as reference.

Another useful method is one where any varying intensity of the detection elements is adjusted, preferably by the use of results from one or several of previous measurements.

Arrays of detection elements are often made up by a high number of detection elements, and it can therefore be advantageous to reduce the number of measured signals prior to assessment, preferably without the loss of any significant information. One such method is to combine the signal from one or more detection element to one signal, for instance by combining 2, maybe more than 2 and even as many as 8 or 16 or 32 or more into one signal.

In some situations e.g. in an analog-to-digital conversion it could also be of interest to adjust the level of 2, preferably 3, more preferably 4, more preferably 5, more preferably 6, more preferably 7, more preferably 8, more preferably more than 8, separate output channels in such a way that one, preferably more than one, of the output channels has/have substantially different level from the other output channel(s), where the identification of which of the output channels, or combination thereof, has substantially different output level, is correlated to the intensity of said signal.

For the analysis of any measured signal it is often necessary to digitalise the signal, in such a way that a given intensity of any signal is transformed into a digital representation. This can be done by having a series of channels, were the information about which of these channels has signal which differs from the other channels determines the intensity, or even by having more than one of this channels forming a combination, preferably in a way similar to binary representation.

Focusing—Lenses

Signals from at least a portion of the sample are focused onto the array of detection elements, by the use of a focusing mean, preferably by the use of one lens, more preferably by the use of two lenses, more preferably by the use of more than two lenses. The number of lenses used for the focusing system can affect the complexity of any measuring system. A system with two or more lenses is normally preferred while a system with only two or even only one lens is preferable.

Adaptive Focusing

The focusing of a signal from the sample onto any detector is dependent on the position of the sample relative to any detector. When the construction of measuring system is such, that the relative position of the sample and any detector can vary, then there is advantage in being able to adjust the focusing of the system. This can often be achieved by first taking at least one measurement of any signal from the sample and then on the bases of is, to adjust the focusing of the system. This procedure can be repeated a number of times in order to obtain acceptable focusing. In the same manner the focusing of signal from the sample or sample material is adjusted, preferably where the extend of the adjustment is determined by at least one measurement of a signal from the sample.

Focusing—Enlargement

In order to increase the amount of electromagnetic radiation which is detected by a detection element, it is often preferable to use one or more lenses to focus the signal from the sample onto the array of detection elements. The magnification of such focusing can be different from 1/1, depending on the set-up of other components of the system, or the particles or sample material used. For instance can enlargement be practical when assessing morphological properties of a particle.

In situations where the particles are relatively small the ratio of the size of a biological particle, to the size of the image of the biological particle on the array of detection elements could be 1/1 or less, preferably less than 1/1 and higher than 1/100, and even less than 1/1 and higher than 1/40, or in other preferred situations less than 1/1 and higher than 1/10, and even in some situations it is preferred the ratio being less than 1/1 and higher than 1/4, more preferably less than 1/1 and higher than 1/2.

Focusing—1/1

When the particles in question have dimensions which is comparable to the size of a detection element, it is often preferred to have magnification of about 1/1, thus focusing the image of any particle on any one or just few detection elements. This can under some condition give favourable detection of any signal.

In these situations it is preferred that the ratio of the size of a biological particle, to the size of the image of the biological particle on the array of detection elements is in the interval between 5/10 and 20/10, preferably in the interval between 6/10 and 18/10, more preferably in the interval between 7/10 and 16/10, more preferably in the interval between 8/10 and 14/10, more preferably in the interval between 9/10 and 12/10, more preferably substantially equal to 10/10.

Focusing—Reduction

When analysing particles which have dimensions which are comparable to, or bigger than the detection elements used, it is often advantageous to reduce the size of the image of such particle, to a degree where the size of the image is comparable to the size of a detection element.

In these situations it is preferred that the ratio of the size of a biological particle, to the size of the image of the biological particle on the array of detection elements is 1/1 or less, preferably less than 1/1 and higher than 1/100, more preferably less than 1/1 and higher than 1/40, more preferably less than 1/1 and higher than 1/10, more preferably less than 1/1 and higher than 1/4, more preferably less than 1/1 and higher than 1/2.

Focusing—Aspect Ratio

Surprisingly it was found that the aspect ratio of an image can be considerably distorted on the array of detection elements, without that having considerable negative effect on the assessment of particles. In such a situation it preferred that the ratio of the shorter to the longer of the two dimensions of the image of a biological particle on the array of detection elements is substantially 1 or less, preferably 1/2 or less, more preferably 1/4 or less, more preferably 1/10 or less, more preferably 1/50 or less, more preferably 1/100 or less, more preferably 1/200 or less, relative to the ratio of the corresponding dimensions of the biological particle. In such situation the ratio of the shorter to the longer of the two dimensions of the image of a biological particle on the array of detection elements is in certain circumstances substantially not the same within the area spanned by the array of detection elements.

Focusing—Collection Angle

The collection angle of a focusing arrangement used can have effect on the intensity of any signal collected on the array of detection elements. When high sensitivity is needed it is therefore practical to increase the collection angle. The preferred size of the collection angle can also be determined by other requirements which are made to the system, such as focusing depth. In these situations the collection angle of the focusing means is 15 degrees or less, preferably more than 15 degrees, more preferably more then 30 degrees, more preferably more than 60 degrees, more preferably more than 90 degrees, more preferably more than 120 degrees, more preferably more than 150 degrees.

Detection Element—Size

The size of the detection elements determines to some extend its sensitivity. In some applications it is therefore of interest to have detection elements of size of about 1 $\mu m^2$ or less. In certain situations the size of the detection elements in the array of detection elements is less than 20 $\mu m^2$, preferably less than 10 $\mu m^2$, more preferably less than 5 $\mu m^2$, more preferably less than 2 $\mu m^2$, more preferably less than or equal to 1 $\mu m^2$. In other situations the size of the detection elements in the array of detection elements is greater than or equal to 5000 $\mu m^2$, preferably greater than or equal to 2000 $\mu m^2$, more preferably greater than or equal to 1000 $\mu m^2$, more preferably greater than or equal to 500 $\mu m^2$, more preferably greater than or equal to 200 $\mu m^2$, more preferably greater than or equal to 100 and less than 200 $\mu m^2$, more preferably greater than or equal to 50 and less than 100 $\mu m^2$, more preferably greater than or equal to 20 and less than 50 $\mu m^2$.

Detection Element—Aspect Ratio

The aspect ratio of the detection elements can be important in the collection of signals for the assessment of particles. A ratio of about 1/1 is some times preferred, but under some conditions it can be preferably to use ratio different from 1/1. In particular when this facilitates detection of signals from increased volume of any sample, thus allowing simultaneous assessment of more particles. In those circumstances the ratio of the shorter of the height or the width, to the longer of the height or the width of the detection elements in the array of detection elements is substantially equal or less than 1, preferably less than 1/2, more preferably less than 1/4, more preferably less than 1/10, more preferably less than 1/50, more preferably less than 1/100, more preferably less than 1/200.

Storage Capacity

Storage capacity, for instance used for storing information about measured signals from the detection elements, is often one of those components which have considerable effect on the cost of production. It is therefore of interest to be able to perform the assessment of particles without substantial any use of such storage capacity, such that the assessment of biological particles in a sample is performed without the use of substantially any storage capacity means being used to store measured signals from the detection elements in the array of detection elements.

On the other hand, it is often difficult to accomplish assessment without the use of any storage capacity, but preferably the amount of such storage capacity should not be more than what is needed to store the information from all measured detection elements, preferably where only a fraction of the information can be stored.

In some situations measured signal from the detection elements in the array of detection elements is stored by means of storage capacity, the storage capacity being able to store a number of measurements equivalent to, or less than, the number of detection elements, preferably less than ½ the number of detection elements, more preferably less than ¼ the number of detection elements, more preferably less than ⅛ the number of detection elements, more preferably less than 1/16 the number of detection elements, more preferably less than 1/32 the number of detection elements, more preferably less than 1/64 the number of detection elements, more preferably less than 1/128 the number of detection elements, more preferably less than 1/256 the number of detection elements, more preferably less than 1/512 the number of detection elements, more preferably less than 1/1024 the number of detection elements in the array of detection elements.

In other certain circumstances it is advantageous that the measured signal from the detection elements in the array of detection elements is stored by means of storage capacity, the storage capacity being able to store a number of measurements greater than the number of detection elements, preferably equivalent to, or greater than, 2 times the number of detection elements, more preferably equivalent to, or greater than, 4 times the number of detection elements, more preferably equivalent to, or greater than, 8 times the number of detection elements, more preferably equivalent to, or greater than, 16 times the number of detection elements, more preferably equivalent to, or greater than, 32 times the number of detection elements, more preferably equivalent to, or greater than, 64 times the number of detection elements, more preferably equivalent to, or greater than, 128 times the number of detection elements, more preferably equivalent to, or greater than, 256 times the number of detection elements, more preferably equivalent to, or greater than, 512 times the number of detection elements, more preferably equivalent to, or greater than, 1024 times the number of detection elements in the array of detection elements.

Other, more complicated aspects of the assessment of particles, can require the use of considerable amount of storage capacity. In this aspect it can therefore be necessary to have storage capacity which can store more information than is collected in one measurement of the detection elements used.

Cuvette

A sample compartment, containing the sample being analysed, arranges preferably as much sample volume as possible in such a way that it can be exposed to the array of detection elements, thus allowing the analysis of many particles simultaneously. One method for accomplishing this, is to define the thickness of sample compartment in a direction which is not parallel to the plane of detection elements, thus increasing the effective volume per are of sample compartment exposed to the detection elements. The optimum thickness often being determined by any effective focus depth of a focusing system.

In such cases the sample compartment limits the dimension of the sample in the direction which is substantially not parallel to the plane of array of detection elements, to a thickness of 20 μm or less, preferably to a thickness of more than 20 μm, more preferably to a thickness of more than 40 μm, more preferably to a thickness of more than 60 μm, more preferably to a thickness of more than 80 μm, more preferably to a thickness of more than 100 μm, more preferably to a thickness of more than 140 μm, more preferably to a thickness of more than 180 μm, more preferably to a thickness of more than 250 μm, more preferably to a thickness of more than 500 μm, more preferably to a thickness of more than 1000 μm.

Similarly, it is advantageous to extend the window of the sample compartment in a direction parallel to the array of detection elements, thus increasing the effective area of the sample being exposed to the array of detection elements. For some of these applications, the length of the dimension being 1 mm or more, preferably 2 mm or more, more preferably 4 mm or more, more preferably 10 mm or more, more preferably 20 mm or more, more preferably 40 mm or more, more preferably 100 mm or more, more preferably 200 mm or more, more preferably 400 mm or more.

For some applications a tubular sample compartment is used whereby it also is possible to increase the number of particles being analysed simultaneously by increasing the radius of such tubular sample compartment. The optimum radius of such sample compartment is often determined by the arrangement of the various components of the system, such as focus depth. The tube can in these circumstances have an inner radius of more than 0.01 mm, preferably 0.02 mm or more, more preferably 0.04 mm or more, more preferably 0.1 mm or more, more preferably 0.2 mm or more, more preferably 0.4 mm or more, more preferably 1 mm or more, more preferably 2 mm or more, more preferably 4 mm or more, more preferably 10 mm or more.

As mentioned above, the focus depth of the system, is often important for the determination of optimal dimensions of a sample compartment. Surprisingly it was found that it was possible to use dimension which exceeded the focus depth of a focusing system, even to an extend where the dimension was greater than 1 times and less than 1.5 times the focusing depth, more preferably equal to, or greater than 1.5 times and less than 2 times said focusing depth, more preferably equal to, or greater than 2 times and less than 3 times said focusing depth, more preferably equal to, or greater than 3 times and less than 4 times said focusing depth, more preferably equal to, or greater than 4 times and less than 6 times said focusing depth, more preferably equal to, or greater than 6 times said focusing depth.

In the present specification and claims, the term "focus depth" designates the distance an object can move along the axis of a focusing system, without its image is distorted, such distortion being defined as when an image, which when in focus illuminates a single detection element, illuminates an area extending to 2 detection elements in one or two directions, when distorted. When two or more detection elements are combined prior to analysis, the combined detection elements should be considered in the definition of focus depth.

The aspect ratio of a window region of the sample compartment can vary from about 1/1, preferably less than 1/2, more preferably less than 1/4, more preferably less than 1/10, more preferably less than 1/20, more preferably less than 1/33, more preferably less than 150, more preferably less than 1/100, more preferably less than 1/200, more preferably less than 1/500, more preferably less than 1/1000, more preferably less than 1/2000, more preferably less than 1/4000, more preferably less than 1/10000, depending on a focusing method, or other aspects of other components of the system The area of the exposing window can be as little as 0.01 $mm^2$ or more, preferably with an area of 0.1 $mm^2$ or more, more preferably with an area of 1 $mm^2$ or more, preferably with an area of 2 $mm^2$ or more, preferably with an area of 4 $mm^2$ or more, preferably with an area of 10 $mm^2$ or more, preferably with an area of 20 $mm^2$ or more, preferably with an area of 40 $mm^2$ or more, more preferably with an area of 100 $mm^2$ or more, preferably with an area of 200 $mm^2$ or more, preferably with an area of 400 $mm^2$ or more, preferably with an area of 1000 $mm^2$ or more, preferably with an area of 2000 $mm^2$ or more, preferably with an area of 4000 $mm^2$ or more, preferably with an area of 10000 $mm^2$ or more. The optimal are of the window often being defined by one or more aspects of this invention Generally the volume of the sample being analysed should be as large as possible. This allows the simultaneous assessment of a higher number of particles, but the optimal volume is often defined by one or more aspects of this invention. For some applications according to the invention the sample compartment limits the boundary of the sample in three directions, in such a way that the volume of the sample is 0.01 μl or more, preferably 0.02 μl or more, more preferably 0.04 μl or more, more preferably 0.1 μl or more, more preferably 0.2 μl or more, more preferably 0.4 μl or more, more preferably 1 μl or more, more preferably 2 μl or more, more preferably 4 μl or more, more preferably 10 μl or more, more preferably 20 μl or more, more preferably 40 μl or more, more preferably 100 μl or more, more preferably 200 μl or more, more preferably 400 μl or more.

In order to increase the effective volume of a sample being measured it can be possible to include means in the sample compartment which can retain completely or partly the particles which are present in the sample. In this way it is possible to analyse a volume which is substantially greater than the physical volume of the sample compartment by sending the sample through the sample compartment prior to analysis and retaining particles from the sample volume inside the sample compartment. Such means for retaining particles could be chemically active means, electronical or magnetic field, or filter. In these circumstances it is preferred that at least one of the boundaries which limit the sample compartment, or a substantially flat surface contained substantially within the boundaries of the sample compartment is a means which can retain particles being assessed, preferably a chemically binding means capable of binding particles, more preferably electronic or magnetic field means capable of withholding particles, more preferably a filtering means capable of passing liquid sample or sample material and retaining particles.

In many preferred embodiments of the present invention, at least one dimension of the sample compartment could be so small that it could be difficult for the sample to flow into or through the sample compartment. By using one aspect of the present invention it is possible to vary at least one of the dimensions defining the sample compartment in such a way that the dimension is substantially greater during the flowing of the sample into or through the sample compartment than during the measurement of any signal from the sample. One effect of such a variation of at least one dimension of the sample compartment can be to partly or substantially completely replace the sample in the sample compartment between the measurement of any signal from the sample. Such embodiments could be where at least one of the dimensions defining boundaries which limit the sample compartment before or during the introduction of the sample to the sample compartment, is substantially different from the dimension during the measurement of any signal from the sample, preferably where the dimension is substantially greater before or during the introduction of the sample to the sample compartment than during the measurement of any signal from the sample, preferably where the dimension being varied is substantially not parallel to the plane of array of detection elements, preferably where the effect of the difference in the dimension is to replace at least a part of the sample in the sample compartment with a different part between measurement of any signal from the sample, preferably where the effect of the difference in the dimension is to improve the flowing of the sample into or through the sample compartment.

Sample Pre-Treatment

Often it is preferred to analyse a sample of a sample material without substantially any modification of the sample in full or in part. Other conditions are favoured by imposing one or more modification upon the sample prior to measurement, for instance by removing interfering components or phenomena, or by allowing some modification of a particle or a part of a particle prior to measurement.

In other circumstances the sample, or parts of said sample, being analysed has been given a chemical, a mechanical or a physical treatment prior to analysis. This treatment could be one or several of the following: exposure to gravity and/or centrifugation, filtering, heating, cooling, mixing, sedimentation, solvation, dilution, homogenisation, sonification, crystallisation, chromatography, ion exchange, electrical field, magnetic field, electromagnetic radiation. The effects of the treatment will normally be an enhancement of any signal observed from the sample used in the assessment of biological particles in the sample, and/or suppression of any interfering signal.

In some of the embodiments of the invention the temperature of the sample can be controlled, either by addition or removal of heat from the sample and the temperature of the sample during measurement of the biological particle containing sample is between 0° C. and 90° C., more preferable between 5° C. and 90° C., more preferable between 10° C. and 90° C., more preferable between 20° C. and 90° C., more preferable between 25° C. and 90° C., more preferable between 30° C. and 90° C., more preferable between 35° C. and 90° C., more preferable between 40° C. and 90° C.

In one situation of assessment the temperature of the sample is controlled by the ambient temperature and the temperature of the sample during measurement of the biological particle containing sample is between 0 C and 90° C., more preferable between 5° C. and 90° C., more preferable between 10° C. and 90° C., more preferable between 20° C. and 90° C., more preferable between 25° C. and 90° C., more preferable between 30° C. and 90° C., more preferable between 35° C. and 90° C., more preferable between 40° C. and 90° C.

Colouring of Objects

Often the particles in question exhibits properties which facilitate the detection of a signal which can be used for the assessment, but sometimes it is preferred to add one or more type of molecules in order to enhance or facilitate any detection of a signal. The number of different types of molecules added depends on the complexity of the assessment, and on the nature of the particles and sample material being analysed. It is for instance often advantageous to use two or more such as 3 or even 4 types of molecules when the assessment concerns the identification of two or more types of particles, where the different particles interact differently with the different molecules, for instance by giving rise to a fluorescent signal at different wavelength. Often the addition of such two or more types of molecules is done simultaneously, but under some conditions it is preferred to add the molecules at different times, preferably in such a way that one or more measurements are carried out between the addition of molecules. These added molecules can interact with the particles for instance by being retained within them, interacting with them or being propelled by them. The molecules being intentionally added to the sample before or during the measurement, preferably one at a time, more preferably more than one at a time.

It is preferred that at least one of the types of molecules is added to a first sample of a sample material and at least another of the types of molecules is added to a second sample of the sample material, preferably where the number of samples of a sample material is equal or less to the number of said different types of molecules, and where at least one measurement is taken from each sample.

In situations where an initial measurement is preferred, the initial measurement is one taken with any intentionally added molecules, a measurement of a sample is taken before at least one of said molecules have been added to the sample and at least one measurement of the sample is taken after all said types of molecules have been added.

The intentionally added molecules can give rise to one or several of the following phenomena assisting in the assessment of biological particles: attenuation of electromagnetic radiation, photoluminescence when illuminated with electromagnetic radiation, scatter of electromagnetic radiation, raman scatter.

The assessment of biological particles can be based on the use of nucleic acid dye as an intentionally added molecule in an amount of more than 30 µg per ml of the sample, more preferable in an amount of less than 30 µg per ml of the sample, more preferable in an amount of less than 20 µg per ml of the sample, more preferable in an amount of less than 10 µg per ml of the sample, more preferable in an amount of less than 5 µg per ml of the sample, more preferable in an amount of less than 2 µg per ml of the sample, more preferable in an amount of less than 1 µg per ml of the sample, more preferable in an amount of less than 0.3 µg per ml of the sample, more preferable in an amount of less than 0.03 µg per ml of the sample, more preferable in an amount of less than 0.003 µg per ml of the sample, more preferable in an amount of less than 0.0003 µg per ml of the sample, the nucleic acid stain being one or several of the following, but not limited to: phenanthridines (e.g. ethidium bromide CAS-1239-45-8, propidium iodide CAS-25535-16-4), acridine dyes (e.g. acridine orange CAS-65-61-2/CAS-10127-02-3), cyanine dyes (e.g. TOTO™-1 iodide CAS#: 143 413-84-7-Molecular Probes, YO-PRO™-1 iodide CAS#: 152 068-09-2-Molecular Probes), indoles and imidazoles (e.g. Hoechst 33258 CAS#: 023 491-45-4, Hoechst 33342 CAS#: 023 491-52-3, DAPI CAS#:28718-90-3, DIPI (4',6-(diimidazolin-2-yl)-2-phenylindole)).

The assessment of biological particles can be based on the use of potentiometric membrane dye as an intentionally added molecule in an amount of either more than 30 µg per ml of the sample, or, more preferable in an amount of at the most 30 µg per ml of the sample, more preferable in an amount of less than 20 µg per ml of the sample, more preferable in an amount of less than 10 µg per ml of the sample, more preferable in an amount of less than 5 µg per ml of the sample, more preferable in an amount of less than 2 µg per ml of the sample, more preferable in an amount of less than 1 µg per ml of the sample, more preferable in an amount of less than 0.3 µg per ml of the sample, more preferable in an amount of less than 0.03 µg per ml of the sample, more preferable in an amount of less than 0.003 µg per ml of the sample, more preferable in an amount of less than 0.0003 µg per ml of the sample, the nucleic acid stain being one or several of the following, but not limited to: Rhodamine-123, Oxonol V.

In order to assure fast assessment of a sample it is of interest to be able to perform analysis shortly after the mixing of any chemical components with sample. This time should therefore be less than 60 seconds, or preferably less than 30 seconds or even as low as 15 seconds and in other preferred situations as low as 10 seconds, and preferably as short as 2 seconds or less and even shorter than 1 second.

One useful method for the introduction of chemical components to the sample is to place one or more chemical component in a container. The container should then be connected to a flow system where the sample flows, and at least a portion of the sample flown through the chemical container and thus allowing the mixing of the chemical components with the sample. In order to control the use of chemical components it is of interest to limit the amount of chemical components to substantially the amount needed for the analysis. The chemical components could be on the form of a liquid solution or suspension, as liquid, or solid. Of particular interest would be to have the chemical components on a form which would allow fast mixing with the sample, for instance by using freeze dried matter. The possibility of being able to replace the chemical container with another chemical container between analysis is of interest in order to assure reproducible addition of chemical components in the measurement of each sample.

Variation in Addition

When performing a quantitative assessment of particles it is normally necessary to control the addition of any component to the sample, in order not to affect the result of the assessment. The present invention offers embodiments where such requirements are less important than under conventional situations. This can be accomplished by introducing the components on a form which has only limited effect on the assessment, such as introducing any component as solid matter, thereby substantially not altering the volume of any sample being analysed, even though the final concentration of any added component displays considerable variation. Further it is possible that the variation in the concentration of one or more intentionally added component(s) or one or more intentionally added molecules in a sample, is less than, or equal to 1%, preferably more than 1%, more preferably more than 2%, more preferably more than 5%, more preferably more than 10%, more preferably more than 25%, more preferably more than 50%, of the average concentration of said component when expressed as 1 standard deviation.

Flow Conditions

In a preferred embodiment of the invention the particles being assessed are substantially at stand-still during measurement, thus allowing the optimal use of measurement time in order to improve any signal to noise conditions. This arrangement also eliminates any error which could be inherent in the assessment of particles caused by variation in flow conditions, particularly when an assessment of a property is a volume related property such as the counting of particles in a volume of sample.

In other preferred embodiments the particles are moving during measurement, thus producing the image of a moving particle on the array of detection elements. This can offer advantage in the assessment of particles, especially when any image of the movement can be used for the identification of a particle. Such movement of image can be homogeneous throughout the array of detection elements, or it can be varying for instance depending on the position of the particle within the sample compartment.

It is also possible to have movements of image, consisting of more than one directional component, which can give advantage when it is necessary to distinguish a particle travelling in a predefined way, from a background signal which is substantially random.

When applying a relative movement between the sample and the array of detecting elements, either by physically moving the sample or by moving the image of the sample relative to the array by, e.g., optical or computer means, the rate of the movement will normally be adapted to the effect to be obtained. Thus, e.g., where the concentration of a type of particle to be counted is very low, it may be advantageous to pass a large volume of sample through of flow system during one exposure, in order to increase the chance that one or more particles will in fact be detected by the array.

The movement of the sample can preferably be accomplished by applying a positive or negative pressure difference across the sample compartment. Such pressure difference can be created by one or several means such as peristaltic pump, piston pump, membrane pump, or syringe.

Flow System

When a sample compartment is substantially mechanically fixed in a measuring system, it is an advantage to make use of a method of flow system, which is capable to flow the sample, and/or any other liquid or component into the sample compartment through an inlet, and out of the sample compartment through an outlet, possibly using the inlet for outlet and thereby reducing the complexity of any flow system. Any such flow is often controlled by the use of one or more valves which can control the flow of sample or any other component. Preferably where the flow of liquid in the sample compartment is brought about by a pump, said pump being situated either upstream to the sample compartment or downstream to the sample compartment, the pump being one or several of the following: peristaltic pump, piston pump, membrane pump, centrifugal pump, hypodermic syringe. Other types of pump could of course be used for this specific topic, but the ones listed above are the ones normally used.

In other preferred situations the flow of liquid in the sample compartment can brought about by a vacuum, the vacuum being applied from a reservoir having a low pressure before the analysis. The vacuum can be established by a mechanical or physical action creating the vacuum substantially simultaneously with the introduction of the sample. These mechanical or physical actions can be: a peristaltic pump, a piston pump, a membrane pump, a centrifugal pump and a hypodermic syringe.

Due to the fact that flow only in one direction is preferred, it is of particular interest to use valves which substantially only allow the flow in one direction. Such valves can be placed up- and/or downstream from the sample compartment. One effect of the use of such valves could be to confine at least a part of the sample in a flow system.

When other components are added to the sample this can be accomplished by means of a flow system which can mix two or more streams of liquid.

In a preferred embodiment of the invention this flow system allows the mixing of the sample material with a solid material which preferably is a mixture of two or more chemical component. The solid material is preferably a freeze dried material.

After any measurement has been carried out, it is preferred that any sample, or other component used being directed to a waste reservoir which is substantially closed to prevent spilling or evaporation from the reservoir whereby a substantially closed flow system is provided according to the invention.

The outlet from the sample compartment is passed through a flow controlling means, such as a valve, which only allows fluid in gas phase to pass through. One such type of valves which often is preferred, is one which allows gas and air to pass but can close when the valve comes in contact with liquid sample.

Disposable Cuvette

Another aspect of the present invention, which is particularly of interest when the sample, or any component added to the sample can be considered hazardous, or difficult to handle, is the use of a removable sample compartment. Such sample compartment is readily removed from the measuring system, allowing another sample compartment to take its place. Preferably such sample compartments can be reused or regenerated, maybe after rinsing.

One interesting aspect of a replaceable sample compartment is the possibility of a method for the substantial irreversible closing of the sample compartment after the addition of a sample or any other components, thus preventing any accidental spill or leakage from the sample compartment during storing or transport.

Such a replaceable sample compartment is preferably with substantially no connection to the flow system during analysis and the sample compartment can preferably be removed from the sensing area between observations for the purpose of replacing the sample within the sample compartment and/or preferably for the purpose of replacing the sample compartment with another sample compartment which preferably containing another sample.

The sample compartment can in some situations be used for the analysis of limited number of samples or sample materials, preferably less than 10, more preferably less than 5, more preferably less than 2, more preferably only 1, before said removable sample compartment being subjected to emptying and/or rinsing and/or addition of one or more components.

In situations where no spilling is preferred and/or where the removable sample compartment is intended to be used only for measurement of one sample or sample material it is preferred that any access to the removable sample compartment is substantially irreversibly closed prior to, during or after analysis, preferably in such a way that any part of the sample material, or any component added to the sample material can not be removed from the removable sample compartment after it has been introduced therein.

When the compartment is intended to be destroyed or re-used after use it is preferred that the compartment is made up by a material which allows destruction by means such as burning or illumination by electromagnetic radiation. In the situations where the destruction comprises a re-use of the material from which the compartment is made of, a process of regeneration of the materials is preferred to comprise one or several of the following steps: emptying the sample compartment for any sample material or any other components, rinsing or washing, removal of one or more physical component of the sample compartment, replacing of one or more physical component of the sample compartment or addition of one or more chemical component.

When addition of a chemical to a sample in the sample compartment it is preferred that the sample compartment can comprise one or more compartments where chemical or physical components can be stored such that the chemical or physical components can be added to any sample present in the sample compartment one at a time or more than one at a time. In this way, the sample compartment can be formed in such a way that it comprises more than one compartments where a portion of the same sample material, or portions of different sample material, or portion of other components can be placed. This is also of interest where, for instance, the assessment involve or allow a controlled mixing of liquids.

A sample compartment with more than one compartment could also allow the analysis of more than one portion of the same sample material, or the analysis of more than one sample materials by allowing the different compartment to be exposed to the array of detection elements.

One aspect of such removable sample compartment is that more than one portions of the same sample material can be subjected to analysis by exposure to the array of detection elements. This can be done by allowing the sample compartment to be moved, thus exposing a different portion of the sample compartment, or by allowing the sample within the sample compartment to flow and thereby substantially replace any sample volume exposed with a different sample volume.

This invention offers also methods for the assessment of particles in a removable sample compartment, where more than one such sample compartments are loaded with sample and placed in a transport means which can move the different sample compartment in a position which allows exposure of signals to the array of detection elements. This allows substantial automation of the assessment of particles since more than one sample can be handled at once.

One preferred implementation of the method is one which allows the substantially simultaneous assessment of more than one sample. This can be accomplished by placing two or more, or even four or more preferably independent measuring systems, comprising at least one sample compartment each, in one disposable sample unit. The signals from the two or more sample compartments can be measured one at a time, or two or more simultaneously.

Sample Volume

In the present section and other sections of this part of the description, the term "sample" does not necessarily mean the sample present in the compartment, but rather the sample introduced into a flow system used according to the invention. It is of interest to minimise the use of sample material and any chemical component used for the analysis. This can be accomplished by the use of the present invention. Sample volumes as small as 5 ml or less and even as small as 0.02 ml can be used. The volume of the sample needed is highly dependent on the number of particles present in the sample and the predetermined statistical quality parameter sought, whereby typical volumes applied is less than 5 ml of a liquid sample, preferably by using less than 2 ml of a liquid sample, more preferably by using less than 1 ml of a liquid sample, more preferably by using less than 0.5 ml of a liquid sample, more preferably by using less than 0.2 ml of a liquid sample, more preferably by using less than 0.1 ml of a liquid sample, more preferably by using less than 0.05 ml of a liquid sample, more preferably by using less than 0.02 ml of a liquid sample, more preferably by using less than 0.01 ml of a liquid sample, the volume being defined as the total volume of any liquid sample introduced to the sample compartment, or any flow system connected to the sample compartment before or after or during the measurement of the sample.

Preferred embodiments of the present invention make it possible to assess particles from a considerably large volumes of sample. This can allow the measurement of samples with only few particles of interest per volume of sample. Sample volumes larger than 10 ml and even larger than 100 ml can be used for the analysis. using more than 1 ml of a liquid sample, preferably by using more than 2 ml of a liquid sample, more preferably by using more than 3 ml of a liquid sample, more preferably by using more than 5 ml of a liquid sample, more preferably by using more than 10 ml of a liquid sample, more preferably by using more than 20 ml of a liquid sample, more preferably by using more than 50 ml of a liquid sample, more preferably by using more than 100 ml of a liquid sample, the volume being defined as the total volume of any liquid sample introduced to any flow system connected to the sample compartment before or after or during the measurement of the sample.

Sampling

Large volume of the sample can be measured by passing the volume of sample through a particle retaining means, such as filter, electrical field, magnetic field, gravitational field. When the particles from a large sample are retained, those particles can be resuspend in a volume which is less than the volume of sample passed through the particle retaining means, preferably where the volume used for the resuspension is only ½ the volume passed through the particle retaining means, more preferably ¼ or less the volume passed through the particle retaining means, more preferably ⅛ or less the volume passed through the particle retaining means, more preferably 1/20 or less the volume passed through the particle retaining means, more preferably 1/50 or less the volume passed through the particle retaining means, more preferably 1/100 or less, or even only 1/100 or less the volume which originally was passed through the particle retaining means. The particle retaining means should preferably be able to retain substantially all particles present in a sample, or at least a substantially representative fraction of at least one type of particles present in the sample.

In one embodiment of the present invention a signal from the particles being analysed is detected while the particles are still substantially retained by a particle retaining means. In such embodiment the particle retaining means are integrated with, or in close connection to a sample compartment.

In the following, the information is given as numbered items, starting with the arbitrary item number 87:

Multiple Exposure

87. A method according to any of the preceding items, where the assessment of the biological objects is based on observation from 2, preferably more than 2 and less than 4, more preferably more than or equal to 4 and less than 8, more preferably more than or equal to 8 and less than 16, more preferably more than or equal to 16 and less than 32, more preferably more than or equal to 32 and less than 64, more preferably more than or equal to 64 and less than 128, more preferably more than or equal to 128 and less than 256, more preferably more than or equal to 256 and less than 512, more preferably more than or equal to 512 and less than 1024, more preferably more than or equal to 1024 measurement periods.

88. A method according to item 87, where at least one of the measurement periods is divided up into at least two periods, where in at least one of the periods the array of detection element is substantially exposed with signals from the sample and where in at least one of the periods the array of detection elements are substantially not exposed to signals from the sample, the periods being controlled by means which can activate the transmission of electromagnetic radiation on the sample, or the emission of, or the transmission of electromagnetic radiation from the sample.

89. A method according to items 87 or 88, where the number of the active periods within a measurement period are 2, preferably 3, more preferably 4, more preferably more than 4 and less than 8, more preferably 8 or more and less than 16, more preferably 16 or more and less than 32, more preferably 32 or more and less than 64, more preferably 64 or more.

90. A method according to any of the items 87 through 89, where each detection element in the array of detection elements measures signal from substantially the same fraction of the sample in two or more of the active periods within a measurement period.

91. A method according to any of the items 87 through 90, where each detection element in the array of detection elements measures signal from substantially different fraction of the sample, preferably where no fraction of the sample is measured by more than one detection elements on the array of detection elements, in two or more of the active periods within a measurement period.

92. A method according to any of the items 87 through 91, where duration of the measurement periods is shorter than or equal to $1 \times 10^{-6}$ seconds, preferably longer than $1 \times 10^{-6}$ seconds and shorter than $1 \times 10^{-5}$ seconds, more preferably longer than $1 \times 10^{-5}$ seconds and shorter than $1 \times 10^{-4}$ seconds, more preferably longer than $1 \times 10^{-4}$ seconds and shorter than $1 \times 10^{-3}$ seconds, more preferably longer than $1 \times 10^{-3}$ seconds and shorter than $1 \times 10^{-2}$ seconds, more preferably longer than $1 \times 10^{-2}$ seconds and shorter than $1 \times 10^{-1}$ seconds, more preferably longer than $1 \times 10^{-1}$ seconds and shorter than 1 second, more preferably longer than 1 second and shorter than 10 seconds, more preferably longer than 10 seconds.

93. A method according to any of the items 87 through 92, where duration of all the measurement periods is substantially equal.

94. A method according to any of the items 87 through 92, where duration of at least 2 said measurement periods is substantially different.

95. A method according to any of the items 87 through 94, where each detection element in the array of detection elements measures signal from substantially the same fraction of the sample in two or more of the measurement periods.

96. A method according to any of the items 87 through 95, where each detection element in the array of detection elements measures signal from substantially different fraction of the sample, preferably where no fraction of the sample is measured by more than one detection elements in the array of detection elements, in two or more of the measurement periods.

Detection Error

97. A method according to any of the preceding items, which can assess the number of biological particles in a sample with total error, expressed as standard prediction error which is more than or equal to 30%, preferably less than 30%, more preferably less than 20%, more preferably less than 10%, more preferably less than 6%, more preferably less than 4, more preferably less than 2%, more preferably less than 1% of the average value of number of biological particles per volume sample.

Sample Throughput

98. A method according to any of the preceding items, where the assessment of biological particles can be carried out at a rate which is less than or equal to 10 assessments per hour, preferably greater than 10 assessments per hour, more preferably greater than 30 assessments per hour, more preferably greater than 50 assessments per hour, more preferably greater than 100 assessments per hour, more preferably greater than 200 assessments per hour, more preferably greater than 300 assessments per hour, more preferably greater than 400 assessments per hour, more preferably greater than 500 assessments per hour, more preferably greater than 600 assessments per hour, more preferably greater than 700 assessments per hour, more preferably greater than 1000 assessments per hour.

99. A method according to any of the preceding items, which uses 2, preferably 3, more preferably 4, more preferably more than 4 parallel detection systems for the substantially simultaneous assessment of biological particles in a sample.

Detection Limits

100. A method according to any of the preceding items, where the assessment of biological particles in a sample is carried out when the number of biological particles in the sample material is grater than $1\times10^8$, preferably less than or equal to $1\times10^8$, more preferably less than $1\times10^7$, more preferably less than $1\times10^6$, more preferably less than $1\times10^5$, more preferably less than $1\times10^4$, more preferably less than $1\times10^3$, more preferably less than $1\times10^2$, more preferably less than 10, more preferably less than 1, more preferably less than 0.1, per ml sample.

Signal Source

101. A method according to any of the preceding items, where the signal which is detected is substantially caused by one or several of the following: photoluminescence with lifetime of the exited state of less than or equal to $10^{-6}$ seconds, photoluminescence with lifetime of the exited state of garter than $10^{-6}$ seconds, chemiluminescence, rayleigh scatter, raman scatter, attenuation of electromagnetic radiation, absorption of the electromagnetic radiation, scatter of the electromagnetic radiation.

Wavelength Sensitivity

102. A method according to any of the preceding items, where the array of detection elements is sensitive to electromagnetic radiation of wavelength in one or several of the following regions: 100 nm to 200 nm, 200 nm to 600 nm, 300 nm to 700 nm, 400 nm to 800 nm, 600 nm to 1 μm, 800 nm to 2 μm, 2 μm to 10 μm, 5 μm to 10 μm, 10 μm to 20 μm, 20 μm to 40 μm.

Wavelength Separation

103. A method according to any of the preceding items, where spectrally rich electromagnetic radiation can be separated into substantially 1 wavelength component or waveband which is transmitted onto the sample, preferably into 2 or more wavelength components or wavebands which are transmitted onto the sample, one at a time or two or more simultaneously.

104. A method according to any of the preceding items, spectrally rich electromagnetic radiation emitted from, or transmitted through the sample is separated into substantially 1 wavelength component or waveband, which is measured by a detection element in said array of detection elements, preferably into 2 or more wavelength components or wavebands, which are measured by a detection element in the array of detection elements, one at a time or two or more simultaneously.

105. A method according to any of the preceding items, where spectrally rich electromagnetic radiation transmitted onto the sample is spatially separated into a plurality of wavelength components, in such a way that at least two fractions of the sample, are exposed to substantially different wavelength components.

106. A method according to any of the preceding items, where spectrally rich electromagnetic radiation emitted from, or transmitted through the sample is spatially separated into a plurality of wavelength components, in such a way that each of the detection elements in the array of detection elements, measuring information from substantially the same fraction of the sample, is exposed to substantially different wavelength components.

107. A method according to any of the items 103 through 106, where the separation of spectrally rich electromagnetic radiation is brought about by one or several of the following, but not limited to: interference filters, coloured filters, an optical grating, a prism, an optically active crystals.

108. A method according to any of the preceding items, where electromagnetic radiation which is transmitted onto, or emitted from, or transmitted through the sample is intensity modulated.

109. A method according to any of the preceding items, where electromagnetic radiation which is transmitted onto, or emitted from, or transmitted through the sample is modulated by optically active crystals or interferometry, preferably by the use of a Michelson interferometer, more preferably by the use of an interferometer where at least one reflecting surface can be moved.

Light Sources

110. A method according to any of the preceding items, where the transmission of electromagnetic radiation onto the sample is accomplished by the use of illuminating means.

111. A method according to item 110, where the illumination means are 2 or more, preferably 3 or more, more preferably 4 or more, more preferably 6 or more, more preferably 8 or more, more preferably 10 or more, light emitting diodes preferably emitting electromagnetic radiation of substantially the same wavelength band.

112. A method according to item 110 or 111, where the electromagnetic radiation transmitted onto the sample is focused by a focusing mean, the focusing mean having the effect of substantially increasing the intensity of said electromagnetic radiation in or at said sample.

113. A method according to any of the items 110 through 112, where the electromagnetic radiation transmitted onto the sample is accomplished by two or more illuminating means, at least two of the illuminating means having substantially different radiation properties in at least one waveband, the illuminating means being operated in such a way that all transmit substantially simultaneously, preferably at least one of the illuminating means transmitting while at least one other of the illuminating means is not transmitting, more preferably where only one of the illuminating means is transmitting at a time.

114. A method according to any of the items 110 through 113, where the illuminating means are one or several of the following, but not limited to: light emitting diodes, lasers, laser diodes, thermal light source, gas discharge lamp.

Reflection

115. A method according to any of the items 110 through 114, where at least a portion of electromagnetic radiation which is transmitted through a sample is reflected back onto or through the sample by the use of a reflecting means, preferably including reflectance means which also can reflect electromagnetic radiation which is scattered or reflected from the boundaries of the sample compartment or the sample is reflected back onto the sample, more preferably where said reflectance means are substantially included in the means which define the boundaries of said sample compartment, preferably where the reflectance mean is one or several dichroic mirrors.

Incidence Angle.

116. A method according to any of the items 110 through 115, where the electromagnetic radiation is transmitted onto said sample from a position which forms an angle which is substantially 0 degrees, preferably between 0 and 15 degrees, more preferably between 14 and 30 degrees, more preferably between 29 and 45 degrees, more preferably between 44 and 60 degrees, more preferably between 59 and 75 degrees, more preferably between 74 and 90 degrees, from the direction between said sample and said array of detection elements.

117. A method according to any of the items 110 through 116, where the electromagnetic radiation is transmitted onto said sample from a position which forms an angle which is substantially 90 degrees, from the direction between said sample and said array of detection elements.

118. A method according to any of the items 110 through 117, where the electromagnetic radiation is transmitted onto said sample from a position which forms an angle which is between 106 and 90 degrees, preferably between 121 and 105 degrees, more preferably between 136 and 120 degrees, more preferably between 151 and 135 degrees, more preferably between 166 and 150 degrees, more preferably between 180 and 165 degrees, more preferably substantially 180 degrees, from the direction between said sample and said array of detection elements.

Detector Types

119. A method according to any of the preceding items, where said array of detection elements is one or several of the following types: full frame CCD, frame transfer CCD, interline transfer CCD, line scan CCD.

120. A method according to any of items #1 through #118, where said array of detection elements is a CMOS image sensor, preferably a CMOS image sensor with on-chip integrated signal condition and/or signal processing, more preferably a CMOS image sensor with on-chip integrated computing means capable of performing image processing.

Signal Conditioning—Software

121. A method according to any of the preceding items, where a measured signal from one or more detection elements is corrected for systematic or varying bias by the use of a calculating means, the bias correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

122. A method according to item 121 where the bias correction is performed by subtracting the results obtained in one or several of other measurements from the measured signal, preferably where the other measurements are one or several of measurements of the same sample, or sample material, more preferably where the other measurement is the measurement taken previously of the same sample or sample material.

123. A method according to any of the preceding items, where a measured signal from one or more detection elements is corrected for intensity by the use of a calculating means, said correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

124. A method according to any of the preceding items, where the assessment of biological particles is done on the bases of two measurements of the same sample, or sample material, where the two measurements are combined by subtracting one of the measurements from the other measurements thereby creating a measurement result where signals occurring in only one of the measurements are represented by either a positive or negative measurement result, and signals occurring in both measurements are represented by substantially zero measurement result, preferably using only positive measurement results in the assessment of biological particles, more preferably using both positive and negative measurement results in the assessment of biological particles, more preferably using the absolute value of the measurement results in the assessment of biological particles.

125. A method according to item 124 where two measurement results are combined by simple addition, preferably where three measurement results are combined, more preferably where four measurement results are combined, more preferably where five measurement results are combined, more preferably where six measurement results are combined, more preferably where more than six measurement results are combined, and used in the assessment of biological particles.

Assessment—One Dimension

126. A method according to any of the preceding items, where the distinction between signals from particles and signal from sample background is based on substantially simultaneous use of more than 1, preferably 2 or more, more preferably 4 or more, more preferably 8 or more, more preferably 16 or, more preferably 32 or, more preferably 64 or more measured signals and/or bias corrected signals and/or sensitivity corrected signals from said detection elements in said array of detection elements.

Assessment—Two Dimensions

127. A method according to any of the preceding items, where signals from more than 1, preferably more than 4, more preferably 10 or more, more preferably 50 or more, more preferably 100 or more, more preferably 200 or more substantially parallel, substantially straight lines of detection elements are used for substantially simultaneous distinction between signal from particles and signal from sample background, preferably by combining the signals from said substantially straight lines into one array of values, each value being obtained by combining one or more signals from substantially each straight lines of detection elements thus allowing data from two dimensional array of detection elements to be analysed in the same manner as data from one dimensional array of detection elements.

128. A method according to any of the preceding items, where the result from the distinction between signal from particles and sample background of the number of objects in 1, preferably 2 or more, more preferably 4 or more, more preferably 8 or more line(s) is/are used in the assessment of biological particles in an adjacent line of detection elements.

Qualitative Assessment

129. A method according to any of the preceding items, where the assessment of biological particles in a sample is used to confirm the presence of any predetermined biological particles in said sample.

Image Processing

130. A method according to any of the preceding items, where the assessment of biological particles is done by subjecting signals from two dimensional array of detection elements to the methods of image processing or image analysis.

Power

131. A method according to any of the preceding items, where the source of electrical power is a transformer, capable of transforming alternating electrical source with alternating voltage between −150 and 150 volt, or with alternating voltage between −250 and 350 volt, or with alternating voltage between −350 and 350 volt, into substantially direct current voltage.

132. A method according to any of the preceding items, where the source of electrical power is one of several of: an accumulator, a removable accumulator, a battery, a rechargeable battery.

Objects

133. A method according to any of the preceding items, where the biological particles are somatic cells and the liquid sample material is milk.

134. A method according to any of the items 1 through 132, where the biological particles are bacteria and the liquid sample material is milk.

135. A method according to any of the items 1 through 132, where the biological particles are bacteria and the liquid sample material is blood.

136. A method according to any of the items 1 through 132, where the biological particles are somatic cells and the liquid sample material is blood.

137. A method according to any of the items 1 through 132, where the biological particles are bacteria and the liquid sample material is urine.

138. A method according to any of the items 1 through 132, where the biological particles are somatic cells and the liquid sample material is urine.

139. A method according to any of the items 1 through 132, where the biological particles are bacteria and the liquid sample material is water.

140. A method according to any of the items 1 through 132, where the biological particles are blood cells and the liquid sample material is blood.

141. A method according to any of the items 1 through 132, where the biological particles are blood platelets and the liquid sample material is blood.

Application

142. A method according to any of the items 1 through 134, where the assessment is the determination of the number of somatic cells in a volume of milk or a milk product, the type of the milk or milk product being one or several of the following: cow milk, goats milk, sheep milk, or buffalo milk.

143. A method according to any of the items 1 through 134, where the assessment is the determination of the number of bacteria in a volume of milk or a milk product, the type of the milk or milk product being one or several of the following: cow milk, goats milk, sheep milk, or buffalo milk.

144. A method according to any of the items 1 through 134, where the assessment is the determination of the types of bacteria in a volume of milk or a milk product, the type of the milk or milk product being one or several of the following: cow milk, goats milk, sheep milk, or buffalo milk.

145. A method according to any of the items 142 through 144, where said assessment is carried out substantially simultaneously with the milking, preferably by including the system at-line, more preferably by including the system in-line with a milking system.

146. A method according to any of the items 142 through 145, where the milk sample is collected during milking, preferably in such a way that the composition of the sample is substantially a representation of the composition of the entire milk being milked, the milk being collected in a container unit, preferably where the container unit also contains at least one sample compartment, the milk sample or a portion of the milk sample being flown into the sample compartment upon completion of the milking.

147. A method according to any of the items 142 through 146, where the results of the assessment are transferred to one or several information storage means, preferably the information storage means also being able to store other information about the milking, more preferably the information storage means also being able to store information about the bulk of milk previously collected.

148. A method according to any of the items 142 through 147, where the information storage means includes means to indicate whether the milk being milked should be directed to one or several of storage facilities or outlet, the indication being based on the assessment of the number of somatic cells per volume, preferably the indication being based on the assessment as well as other information present in the information storage means about milking of individual animals or the bulk of milk, the other information being one or several of, but limited to: conductivity, impedance, temperature, fat content, protein content, lactose content, urea content, citric acid content, ketone content, somatic cell count.

149. A method according to any of the items 142 through 148, where the purpose of the direction of any milk being milked to one or several of storage facilities or outlets is to adjust the properties of any bulk of milk, preferably with regard to the number of somatic cells per volume.

150. A method according to any of the items 142 through 149, where the assessment is carried out after the milking has taken place, preferably the milk being substantially not altered before measurement.

151. A method according to any of the items 142 through 149, where the assessment is carried out after the milking has taken place, the milk being modified before measurement, preferably in such a way that the modification extends the durability of the sample material, the modification being one or several of, but not limited to; addition of one or more chemical component which substantially inhibits bacterial growth in the sample material, addition of one or more chemical component which substantially inhibits the growth of fungus, addition of one or more chemical component which has colouring properties said colouring being used to aid visual identification of the milk.

152. A method according to any of the items 142 through 151, where the assessment is carried out substantially simultaneously with the assessment of the amount of any constituent in said sample material, preferably by using substantially a same portion of the sample material for the assessment, said constituent being one or several of, but not limited to: fat, protein, lactose, urea, citric acid, glucose, ketones, carbon dioxide, oxygen, pH, potassium, calcium, sodium.

153. A method according to item 152, where the assessment of any chemical constituent is based on spectrophotometric measurement, the spectrophotometric measurement being one or several of, but not limited to; mid-infrared attenuation, near-infrared attenuation, visible attenuation, ultra-violet attenuation, photoluminescence, raman scatter, nuclear magnetic resonance.

154. A method according to item 152 through 153, where the assessment of any chemical constituent is based on potentiometric measurement, preferably by the use of ion selective electrode.

155. A method according to any of the items 142 through 154, where the sample material is either a milk sample used for heard improvement purposes, or a milk sample used in a payment scheme.

156. A method according to any of the items 142 through 155, where the sample material is a milk sample taken from one quarter of the udder, preferably where the purpose of the assessment of biological particles is to determine the status of health.

157. A method according to any of the items 1 through 132 or item 136, where the assessment is the determination of the number of somatic cells in a volume of blood or a blood product, the type of the blood or blood product being one or several of the following: human blood, animal blood, cow blood, goats blood, sheep blood, or buffalo blood.

158. A method according to any of the items 1 through 132 or item 135, where the assessment is the determination of the number of bacteria in a volume of blood or a blood product, the type of the blood or blood product being one or several of the following: human blood, animal blood, cow blood, goats blood, sheep blood, or buffalo blood.

159. A method according to any of the items 1 through 132 or item 135, where the assessment is the determination of the types of bacteria in a volume of blood or a blood product, the type of the blood or blood product being one or several of the following: human blood, animal blood, cow blood, goats blood, sheep blood, or buffalo blood.

160. A method according to any of the items 1 through 132 or any of item 135 or 136, where the assessment is the estimation of rate of sedimentation of biological particles in a volume of blood or a blood product, the type of the blood or blood product being one or several of the following: human blood, animal blood, cow blood, goats blood, sheep blood, or buffalo blood.

161. A method according to any of the items 1 through 132 or item 138, where the assessment is the determination of the number of somatic cells in a volume of urine or a urine product, the type of the urine or urine product being one or several of the following: human urine, animal urine, cow urine, goats urine, sheep urine, or buffalo urine.

162. A method according to any of the items 1 through 132 or item 137, where the assessment is the determination of the number of bacteria in a volume of urine or a urine product, the type of the urine or urine product being one or several of the following: human urine, animal urine, cow urine, goats urine, sheep urine, or buffalo urine.

163. A method according to any of the items 1 through 132 or item 137, where the assessment is the determination of the types of bacteria in a volume of urine or a urine product, the type of the urine or urine product being one or several of the following: human urine, animal urine, cow urine, goats urine, sheep urine, or buffalo urine.

164. A method according to any of the items 1 through 132 or any of item 137 or 138, where the assessment is the estimation of rate of sedimentation of biological particles in a volume of urine or a urine product, the type of the urine or urine product being one or several of the following: human urine, animal urine, cow urine, goats urine, sheep urine, or buffalo urine.

165. A method according to any of the items 157 through 164, where the purpose of the assessment is to obtain information about the status of health, such as infection, preferably where the assessment is carried out in medical doctor office, physician office or veterinary office.

166. A method according to any of the items 157 through 165, where the assessment is carried out substantially simultaneously with the assessment of the amount of any constituent in said sample material, preferably by using substantially a same portion of the sample material for the assessment, said constituent being one or several of, but not limited to: fat, cholesterol, protein, lactose, urea, citric acid, glucose, ketones, carbon dioxide, oxygen, pH, potassium, calcium, sodium.

167. A method according to any of the items 157 through 166, where said assessment of any chemical constituent is based on spectrophotometric measurement, the spectrophotometric measurement being one or several of, but not limited to mid-infrared attenuation, near-infrared attenuation, visible attenuation, ultra-violet attenuation, photoluminescence, raman scatter, nuclear magnetic resonance.

168. A method according to any of the items 157 through 167, where said assessment of any chemical constituent is based on potentiometric measurement, preferably by the use of ion selective electrode.

169. A method according to any of the preceding items, where substantially entirely all the sample material used for the assessment along with any components intentionally added to the sample material or portion of the sample material is returned to a vial after the completion of the assessment, preferably the vial being substantially closed to prevent spilling or evaporation of any material contained within the vial, more preferably the vial prior to the addition of any sample material, contains one or more chemical components, the function of the chemical components being one, or several, but not limited to: substantial inhibition of bacterial growth, substantial inhibition of growth of fungus.

170. A method according to any of the preceding items, where the sample material to be measured is contained in substantially closed, preferably where the container, or at least a part of the container, can be used as a sample compartment, substantially entirely all the sample material used for the assessment along with any components intentionally added to the sample material or portion of the sample material is retained in the container after the completion of the measurement.

Sample Media

171. A method according to any of the preceding items, where the sample being analysed is substantially an aqueous solution or an organic solution.

172. A method according to any of the preceding items, where the sample being analysed contains two or more phases in suspension, at least one of the phases being immiscible under the condition the measurements are carried out.

173. A method according to any of the preceding items, where all the phases of the sample are substantially liquid under the condition the measurements are carried out.

174. A method according to any of the preceding items, where at least one of the phases of the sample is/are substantially solid under the condition the measurements are carried out.

175. A method according to any of the preceding items, where the sample contains material, the material being dissolved and/or suspended, the amount of the material being substantially more than or equal 25%, preferably less than 25%, more preferably less than 10%, more preferably less than 5%, more preferably less than 1%, more preferably less than 0.1%, more preferably less than 0.01%, more preferably less than 0.001%, more preferably less than 0.0001%, more preferably less than 0.00001%, more preferably less than 0.000001%, of the total weight of said sample.

176. A method according to any of the preceding items, where substantially entirely no components have intentionally been added to the sample being analysed.

177. A method according to any of the preceding items, where the sample has been intentionally modified by the addition of 1 solid, liquid, dissolved or suspended component equivalent to more than or equal to 50%, preferably less than 50%, more preferably less than 35, more preferably less than 20%, more preferably less than 10%, more preferably less than 5%, more preferably less than 2%, more preferably less than 1%, more preferably less than 0.1%, more preferably less than 0.01%, more preferably less than 0.001%, more preferably less than 0.0001%, more preferably less than 0.00001%, more preferably less than 0.000001% of the total weight of the sample.

178. A method according to item 177, where the addition comprises more than or equal to 10, preferably less than 10, more preferably less than 6, more preferably less than 4, more preferably less than 3 solid, liquid, dissolved, or suspended components.

179. A method according to item 177 or 178, where said addition of said 1 or more components enhances the signal detected from the objects in a sample.

180. A method according to any of the items 177 through 179, where said addition of said 1 or more components suppresses one or more signals from the sample which is being measured, the signal being a signal interfering with the signal detected from the biological particles in a sample.

181. A method according to any of the items 177 through 179, where one of intentionally added chemical components has the effect of adjusting the pH of the sample before or during the assessment, the chemical component being one or several of the following, but not limited to: citric acid, citrate, acidic acid, acetate, phosphor acid, phosphate, carbonate, bicarbonate, boric acid, borate.

182. A method according to any of the items 177 through 179, where one intentionally added chemical components has the effect of adjusting the pH of the sample before or during the assessment, the chemical component being a mixture of citric acid and citrate.

183. A method according to any of the items 177 through 179, where one intentionally added chemical components has the effect of enhancing any signal detected from the biological particles, the chemical component being a mixture of citric acid and citrate.

184. A method according to any of the items 177 through 179, where one of intentionally added chemical components has the effect of surfactant, the chemical component being of one or several of the following groups of surfactants, but not limited to: anionic surfactant, cationic surfactant, amphoteric surfactant, nonionic surfactant.

185. A method according to item 184 where one intentionally added chemical component is t-Octylphenoxypolyethoxyethanol (Triton X-100).

186. A method according to any of the items 177 through 179, where one of intentionally added chemical components has the effect of binding one or several of metal ions present in the sample, preferably the chemical component being one capable of forming a metal ion complex with the metal ion.

187. A method according to item 186, where the intentionally added chemical component is one or several of the following, but not limited to: EDTA, Oxalic acid, Oxalate, Ethylene glycol-bis(β-aminoethyl ether) N,N,N',N'-tetraacetec acid (EGTA).

Type of Objects

188. A method according to any of the preceding items, where the biological particles to be assessed are one or several of the following, but not limited to: somatic cells, red blood cells, blood platelets, bacteria, yeast cells, fragments of cells, lipid globules, protein micelles, plankton, algae.

189. A method according to any of the preceding items, where the biological particles to be assessed comprises polymer beads bound to biological particles or components in connection with assessment of these biological molecules or components.

Type of Specimen

190. A method according to any of the preceding items, where the sample material is one or several of the following, but not limited to: specimen of human origin, specimen of animal origin, drinking water, waste water, process water, sea water, lake water, river water, ground water, water used for heating, water used for cooling, water used for adjusting humidity, water used for washing or bathing, water used in pool or swimming pool, food, feed or components of food and feed, milk or a milk product, blood or a blood product, urine, faeces, saliva, specimen from an inflammation, specimen from the petrochemical industry, specimen from the pharmaceutical industry, specimen from the food or feed industry.

Object Size

191. A method according to any of the preceding items, where the average size of the biological particle to be assessed is less than 0.01 μm, preferably less than 0.1 μm, more preferably less than 1 μm, more preferably less than 2 μm, more preferably less than 3 μm, more preferably less than 4 μm, more preferably less than 6 μm, more preferably less than 10 μm, more preferably less than 20 μm, more preferably less than 50 μm, more preferably less than 100 μm.

192. A method according to any of the preceding items, where the average size of the biological particle to be assessed is larger than or equal to 100 μm, preferably larger than 150 μm, more preferably larger than 200 μm, more preferably larger than 400 μm.

Licences

Somatic Cells in Milk

193. A method according to any of the preceding items, wherein the biological particles are somatic cells or fragments thereof, and the sample material is a milk sample, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

194. A method according to item 193, wherein the signal originates from one or several types of molecules intentionally added to said sample which interact or bind to or interact with the somatic cells or parts of the somatic cells, preferably by binding to or interacting with DNA material contained within or originating from the somatic cells.

On-Farm

195. A method according to any of items #1 through #192, wherein the biological particles are somatic cells or fragments thereof, and the sample material is a milk sample, the purpose of the assessment being to obtain information about the health status of a milking animal, preferably to obtain information about subclinical or clinical mastitis, the sample of the sample material is placed in a sample compartment by the use of a flow means capable of replacing the sample within the sample compartment with a different sample, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

196. A method according to item 195, wherein the signal originates from one or several types of molecules intentionally added to said sample which interact or bind to or interact with the somatic cells or parts of the somatic cells, preferably by binding to or interacting with DNA material contained within or originating from the somatic cells.

Central Laboratory

197. A method according to any of items #1 through #192, wherein the biological particles are somatic cells or fragments thereof, and the sample material is a milk sample, the sample of the sample material is placed in a sample compartment by the use of a flow means capable of replacing the sample within the sample compartment with a different sample the time between the replacement of sample material being shorter than 30 seconds, preferably shorter than 15 seconds, more preferably shorter than 10 seconds, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

198. A method according to item 197, wherein the signal originates from one or several types of molecules intentionally added to said sample which interact or bind to or interact with the somatic cells or parts of the somatic cells, preferably by binding to or interacting with DNA material contained within or originating from the somatic cells.

On-Line

199. A method according to any of items #1 through #192, wherein the biological particles are somatic cells or fragments thereof, and the sample material is a milk sample, the assessment being performed substantially at the beginning of milking, or during milking, or immediately after milking has taken place, the sample of the sample material is placed in a sample compartment by the use of a flow means capable of replacing the sample within the sample compartment with a different sample flowing milk directly from a milking unit or flowing milk from an intermediate reservoir which is gradually filled during milking, preferably where said reservoir is filled with milk substantially representing the composition of the total volume of milk being milked, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

200. A method according to item 199, wherein the signal originates from one or several types of molecules intentionally added to said sample which interact or bind to or interact with the somatic cells or parts of the somatic cells, preferably by binding to or interacting with DNA material contained within or originating from the somatic cells.

Disposable Cuvette

201. A method according to any of items #1 through #192, wherein the biological particles are somatic cells or fragments thereof, and the sample material is a milk sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

202. A method according to item 201, wherein the signal originates from one or several types of molecules intentionally added to said sample which interact or bind to or interact with the somatic cells or parts of the somatic cells, preferably by binding to or interacting with DNA material contained within or originating from the somatic cells.

Bacteria in Milk

203. A method according to any of items #1 through #192, wherein the biological particles are bacteria or fragments thereof, and the sample material is a milk sample, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

204. A method according to item 203, wherein the signal originates from one or several types of molecules intentionally added to said sample which interact or bind to or interact with the bacteria or parts of the bacteria, preferably by binding to or interacting with DNA material contained within or originating from the bacteria.

On-Farm

205. A method according to any of items #1 through #192, wherein the biological particles are bacteria or fragments thereof, and the sample material is a milk sample, the purpose of the assessment being to obtain information about the health status of a milking animal, preferably to obtain information about subclinical or clinical mastitis, the sample of the sample material is placed in a sample compartment by the use of a flow means capable of replacing the sample within the sample compartment with a different sample, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

206. A method according to item 205, wherein the signal originates from one or several types of molecules intentionally added to said sample which interact or bind to or interact with the bacteria or parts of the bacteria, preferably by binding to or interacting with DNA material contained within or originating from the bacteria.

Central Laboratory

207. A method according to any of items #1 through #192, wherein the biological particles are bacteria or fragments thereof, and the sample material is a milk sample, the sample of the sample material is placed in a sample compartment by the use of a flow means capable of replacing the sample within the sample compartment with a different sample the time between the replacement of sample material being shorter than 30 seconds, preferably shorter than 15 seconds, more preferably shorter than 10 seconds, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

208. A method according to item 207, wherein the signal originates from one or several types of molecules intentionally added to said sample which interact or bind to or interact with the bacteria or parts of the bacteria, preferably by binding to or interacting with DNA material contained within or originating from the bacteria.

On-Line

209. A method according to any of items #1 through #192, wherein the biological particles are bacteria or fragments thereof, and the sample material is a milk sample, the assessment being performed substantially at the beginning of milking, or during milking, or immediately after milking has taken place, the sample of the sample material is placed in a sample compartment by the use of a flow means capable of replacing the sample within the sample compartment with a different sample flowing milk directly from a milking unit or flowing milk from an intermediate reservoir which is gradually filled during milking, preferably where said reservoir is filled with milk substantially representing the composition of the total volume of milk being milked, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

210. A method according to item 209, wherein the signal originates from one or several types of molecules intentionally added to said sample which interact or bind to or interact with the bacteria or parts of the bacteria, preferably by binding to or interacting with DNA material contained within or originating from the bacteria.

Disposable Cuvette

211. A method according to any of items #1 through #192, wherein the biological particles are bacteria or fragments thereof, and the sample material is a milk sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

212. A method according to item 211, wherein the signal originates from one or several types of molecules intentionally added to said sample which interact or bind to or interact with the bacteria or parts of the bacteria, preferably by binding to or interacting with DNA material contained within or originating from the bacteria.

Somatic Cells in Blood

213. A method according to any of items #1 through #192, wherein the biological particles are somatic cells or fragments thereof, and the sample material is a blood sample, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

214. A method according to item 213, wherein the signal originates from one or several types of molecules intentionally added to said sample which interact or bind to or interact with the somatic cells or parts of the somatic cells, preferably by binding to or interacting with DNA material contained within or originating from the somatic cells.

Disposable Cuvette

215. A method according to any of items #1 through #192, wherein the biological particles are somatic cells or fragments thereof, and the sample material is a blood sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

216. A method according to item 215, wherein the signal originates from one or several types of molecules intentionally added to said sample which interact or bind to or interact with the somatic cells or parts of the somatic cells, preferably by binding to or interacting with DNA material contained within or originating from the somatic cells.

Somatic Cells in Urine

217. A method according to any of items #1 through #192, wherein the biological particles are somatic cells or fragments thereof, and the sample material is a urine sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

218. A method according to item 217, wherein the signal originates from one or several types of molecules intentionally added to said sample which interact or bind to or interact with the somatic cells or parts of the somatic cells, preferably by binding to or interacting with DNA material contained within or originating from the somatic cells.

Disposable Cuvette

219. A method according to any of items #1 through #192, wherein the biological particles are somatic cells or fragments thereof, and the sample material is a urine sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said somatic cells or portions of said somatic cells or components interacting with or bound to the somatic cells or portions thereof.

220. A method according to item 219, wherein the signal originates from one or several types of molecules intentionally added to said sample which interact or bind to or interact with the somatic cells or parts of the somatic cells, preferably by binding to or interacting with DNA material contained within or originating from the somatic cells.

Bacteria in Urine

221. A method according to any of items #1 through #192, wherein the biological particles are bacteria or fragments thereof, and the sample material is a urine sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

222. A method according to item 221, wherein the signal originates from one or several types of molecules intentionally added to said sample which interact or bind to or interact with the bacteria or parts of the bacteria, preferably by binding to or interacting with DNA material contained within or originating from the bacteria.

Disposable Cuvette

223. A method according to any of items #1 through #192, wherein the biological particles are bacteria or fragments thereof, and the sample material is a urine sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

224. A method according to item 223, wherein the signal originates from one or several types of molecules intentionally added to said sample which interact or bind to or interact with the bacteria or parts of the bacteria, preferably by binding to or interacting with DNA material contained within or originating from the bacteria.

Bacteria Water

225. A method according to any of items #1 through #192, wherein the biological particles are bacteria or fragments thereof, and the sample material is a water sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

226. A method according to item 225, wherein the signal originates from one or several types of molecules intentionally added to said sample which interact or bind to or interact with the bacteria or parts of the bacteria, preferably by binding to or interacting with DNA material contained within or originating from the bacteria.

Disposable Cuvette

227. A method according to any of items #1 through #192, wherein the biological particles are bacteria or fragments thereof, and the sample material is a water sample, a portion of the sample material is placed in a sample compartment being at least a part of a unit which can be replaced between substantially every assessment or where each of said units can only be used for said assessment of one of said sample materials, the sample of the sample material is illuminated in the sample compartment with electromagnetic radiation where at least a portion of said electromagnetic radiation has energy which can give rise to a photoluminescence signal, preferably fluorescent signal, the signal originating at least from said bacteria or portions of said bacteria or components interacting with or bound to the bacteria or portions thereof.

228. A method according to item 227, wherein the signal originates from one or several types of molecules intentionally added to said sample which interact or bind to or interact with the bacteria or parts of the bacteria, preferably by binding to or interacting with DNA material contained within or originating from the bacteria.

229. A device capable of the assessment of biological particles in a volume of liquid sample material according to any of the preceding items.

229. A device capable of the assessment of biological particles in a volume of liquid sample material according to any of the items 1 through 229 comprising at least means for flowing the sample to a sample compartment, means for the detection of any signal from the sample and means for the electronical or digital transformation of any such signal.

229. A device capable of the assessment of biological particles in a volume of liquid sample material according to any of the items 1 through 229 comprising at least a sample compartment, means for the detection of any signal from the sample and means for the electronical or digital transformation of any such signal.

Multiple Exposure

In order to allow optimal assessment of particles it is possible to base such assessment on a number of measurements which are taken from a sample. One advantage is to make repeated measurement of the same portion of a sample, thus improving any signal to noise condition by the use of propagation of error. Another aspect is to increase the total volume of sample which is analysed by taking more than one measurements from different portion of a sample.

Under some conditions it can be advantageous to adjust the measurement time, for instance when the intensity of signals is varying, maybe depending on which type of particles are being analysed.

Detection Error

The present invention offers methods for the assessment of the number of biological particles in a sample with total error, expressed as relative prediction error in percent of the average number of particles in a volume, which preferably is less than 30% and often as low as 10% or even as low or less than 1%. This can be obtained for instance by controlling the volume of sample which is analysed.

Sample Throughput

The method of the present invention allow the assessment of biological particles at a rate which preferably amounts to 10 or more assessments per hour, and even as many as 100 or more assessments per hour, even as many as 1000 or more assessments per hour.

It is also possible to combine more than one more or less identical analysing systems, in such a way that they work in parallel and thereby constitute a method which can assess even higher number of samples per hour.

Detection Limits

The extensive flexibility of the method of the present invention, makes it possible to analyse volumes, which can allow the assessment of particles in samples where the total number of such particles per volume is ranging from more than $1 \times 10^8$ particles per ml sample to less and 1 particle per ml sample. one of the most important aspect for that purpose being the total volume being analysed.

Signal Source

The signals which the assessment of particles can be based on are virtually any type of electromagnetic radiation, and in particular where the source of such electromagnetic radiation or mechanism having influence of it can be photoluminescence with lifetime of the exited state of less than or equal to $10^{-6}$ seconds, photoluminescence with lifetime of the exited state of garter than $10^{-6}$ seconds, chemiluminescence, rayleigh scatter, raman scatter, attenuation of electromagnetic radiation, absorption of the electromagnetic radiation, scatter of the electromagnetic radiation.

Wavelength Sensitivity

When the signal being detected is an electromagnetic radiation it is preferred to use a detection element which is sensitive to such radiation. Preferred embodiments use arrays of detection elements which are sensitive to electromagnetic radiation of wavelength in one or several of the following regions: 100 nm to 200 nm, 200 nm to 600 nm, 300 nm to 700 nm, 400 nm to 800 nm, 600 nm to 1 µm, 800 nm to 2 µm, 2 µm to 10 µm, 5 µm to 10 µm, 10 µm to 20 µm, 20 µm to 40 µm.

Wavelength Separation

It is often of interest to separate electromagnetic radiation into separate wavelengths or wavebands, especially when the source of such radiation emits energy over a broad spectrum of wavelengths. In methods of assessment of particles which are based on attenuation of energy, detection of emitted or scattered energy or the like, the ability of being able to separate energy into separate wavelengths or wavebands, is important. This applies also to any electromagnetic radiation which originates from within the sample, for instance by means of photoluminescence or chemiluminescence. In some methods of this invention it is possible to use information obtained when using two or more different wavelengths or wavebands, for instance to distinguish between two or more types of particles on the bases of how those react to different energies.

One method of performing such wavelength separation is to illuminate a portion of a sample with more than one wavelength or waveband simultaneously, preferably in such a way that different portions of the sample are illuminated with different wavelengths or wavebands of energy. This is particularly of interest when the assessment of particles concerns the identification of one or more types of particles since particles are exposed to different wavelength energy depending on their position within the sample compartment.

Another method of performing such wavelength separation is to separate any electromagnetic radiation emitted from the sample, preferably where more than two detection elements observe signals from substantially the same portion of the sample but due to the wavelength separation these detection elements detect different wavelengths or wavebands of energy. Thereby it is possible to derive spectral characteristics of any particle which can be used for its assessment.

One method is the intensity modulation of electromagnetic radiation. When such modulation is controlled it is possible to use it for the improvement of signal to noise ratio, for instance by observing any background signal in a period where the intensity is low or zero, and then correcting any signal measured when the intensity is high, by the background information.

It is also possible to frequency modulate electromagnetic radiation by the use of an optically active crystals or by the use of an interferometer. The effect of such modulation could be to obtain spectral information about any particle present in the sample.

Light Sources

In methods based on attenuation of electromagnetic radiation, or illumination of the sample it is preferred to use a source of radiation such as light emitting diodes, lasers, laser diodes, thermal light source or gas discharge lamp. When the intensity of the illuminating energy is of interest it is possible to use more than one energy source, even when the different light sources have different energy spectrum, for instance when two different light emitting diodes are used which emit energy in different wavebands.

To improve the efficiency of such light source in illuminating the sample it is often desirable to use a focusing system for focusing energy onto the sample.

Reflection

When the electromagnetic radiation is used to illuminate a sample for the purpose of causing photoluminescence or the like, it is of interest to be able to increase the efficiency of such radiation source by being able to reflect any energy which is transmitted through the sample back onto the sample, preferably by the use of a reflecting means, for instance dichroic mirrors, which reflect energy of certain wavelengths while allowing the transmission of energies at other wavelengths.

Incidence Angle.

In a method of this invention using photoluminescence as sources of detected signal, it is possible to arrange the light source, relative to the axis of the sample compartment, and particularly relative to an axis which the array of detection elements and the sample compartment form, in such a way that the angle between the axis and the light source is between 0 and 180 degrees.

Detector Types

As detection elements, it is possible to use one of several commercially available arrays of detection elements, such as array of charge coupled devices (CCD) or array of light sensitive diodes (CMOS image sensor). Such arrays of detection elements can have on-chip integrated signal condition and/or signal processing facilities.

Signal Conditioning—Software

At least one embodiment makes use of a calculating means, such as a digital computer, which at least can be used for the correction of any measured signal for a systematic or varying bias, for instance by using one or more predetermined variable to adjust the measured signal. The determination of the predefined variable can be done on the bases of values form measured signals of one or more reference element situated close to the element being corrected, or it can be done on the bases of values from one or several of any other measurements.

In particular it is of interest to subtract one of the other measured signals, often one of previously measured signals, from the measured signal, thereby removing any bias effect which also was present in the other measurement. The other measurement can be another measurement of a different portion of the same sample, or a measurement of a different sample.

Such calculating means can also be used to correct a measured signal for variation in sensitivity, by using one or more predefined variable. The determination of the predefined variable can be done on the bases of values form measured signals of one or more reference element situated close to the element being corrected, or it can be done on the bases of values from one or several of any previous measurements.

One suitable method for the correction of measured signals is to subtract one result from an array of detection elements from another results, obtained form a different portion of the same sample, or from a different sample. Such subtraction has the effect of reducing, or removing any systematic variation in baseline levels of the signals from the array of detection elements, caused by dark-current or possibly by particles which are immobilised on the interior of the sample compartment, any assessment being based on substantially only the positive results of such subtraction. If the two measurement originate from different portion of the same sample, then it is also possible to perform assessment on the bases of the result from the subtraction by treating any negative result from the subtraction as positive number, thus effectively performing an assessment of more than one measurement with the same efforts as when a single measurement is used. In this way it is possible to combine the result from more than one subtraction, preferably as many as the actual noise level allows, for instance by keeping the noise in the combined results less than a given fraction of the smallest signals which are used for the assessment of particles.

Image Processing

The present invention is well suited for making use of state of the art image processing in the assessment of particles, for instance when the assessment is the identification of one or more of different types of particles.

Power

Any instrument constructed according to the present invention can be operated on electrical power, such as 110 or 220 V AC, by the use of appropriate transformer system. A battery or an accumulator can also be used as a source of power, and this is in particular of interest when the instrument is intended for use where the transport of the instrument is required. Such battery or accumulator can also be one which can be recharged, thereby making it possible to regenerate and reuse.

The invention claimed is:

1. A system for the assessment of at least one quantity parameter and/or at least one quality parameter of biological particles in a liquid analyte material, comprising
   a sample compartment having a wall part defining an exposing area, the wall part allowing electromagnetic radiation from a liquid sample in the sample compartment to pass through the wall and to be exposed to the exterior, the volume of the liquid sample from which electromagnetic radiation is exposed onto an array of active detection elements being in the range of 0.01 µl to 20 µl,
   one or more LEDs arranged to transmit light onto the sample,
   an array of active detection elements, onto which an at least one-dimensional spatial image of said volume can be exposed, the image being one which is detectable as an intensity by individual active detection elements, under conditions which will permit processing of the intensities detected by the array of detection elements during the exposure in such a manner that images of electromagnetic signals from the biological particles are identified as distinct from images of electromagnetic signals from background signals,
   a lens consisting of one or several elements for focusing an image of electromagnetic signals from at least part of the exposing domain onto the array of detection elements, the spatial representation exposed onto the array of detection elements being subject to such a linear enlargement that the ratio of a linear dimension of the image on the array of detection elements to the original linear dimension in the exposing domain is smaller than 10:1,
   at least one monochromatic device for separating electronic radiation into substantially one or more wavelength components or wavebands allowing the system to receive fluorescence, and
   a computer unit for processing the intensities detected by the detection elements in such a manner that signals from the biological particles are identified as distinct from background signals, and for correlating the results of the processing to the at least one quantity parameter and/or the at least one quality parameter of the liquid analyte material.

2. The system according to claim 1, wherein at least a major part of the electromagnetic radiation from the light source, has a direction which is transverse to the wall of the sample compartment or a plane defined by the domain.

3. The system according to claim 1, comprising a plurality of light emitting diodes.

4. The system according to claim 3, wherein the light emitting diodes emit electromagnetic radiation of substantially the same wavelength.

5. The system to claim 3, wherein at least two light emitting diodes have substantially different radiation properties in at least one waveband, the light emitting diodes being operated in such a way that all transmit substantially simultaneously or at least one source transmits while at least one diode is not transmitting, or at least one diode is transmitting at a time.

6. The system of claim 1, comprising one or more valves which can control the flow of sample or any other component.

7. The system according to claim 1, wherein the array of detection elements is arranged in two directions in such a way that the detection elements form a series of substantially parallel straight lines, the series forming a rectangle.

8. The system according to claim 1, wherein the ratio is at the most 6:1.

9. The system according to claim 1, wherein the ratio is smaller than 4.1.

10. The system according to claim 1, wherein the ratio is in the range between 10:1 and 1:10.

11. The system according to claim 1, wherein the ratio is in the range between 1:1 and 1:100.

12. The system according to claim 1, wherein the interior of the sample compartment has an average thickness of 20 µm to 200 µm.

13. The system according to claim 1, wherein the sample compartment has dimensions, in a direction substantially parallel to the array of detection elements, in the range between 1 mm by 1 mm and 10 mm by 10 mm.

14. The system according to claim 1, wherein the volume of the liquid sample from which electromagnetic radiation is exposed onto the array is in the range of 0.01 µl to 1 µl.

15. The system according to claim 1, wherein the volume of the liquid sample from which electromagnetic radiation is exposed onto the array is in the range of 0.04 µl to 4 µl.

16. The system according to claim 1, comprising a pump, said pump being situated either upstream to the sample compartment or downstream to the sample compartment.

17. The system according to claim 16, wherein the pump is one or several of the following: peristaltic pump piston pump, membrane pump, centrifugal pump, and hypodermic syringe.

18. The system according to claim 1, wherein the computer unit is capable of assessing the number of the biological particles per volume of the liquid analyte material.

19. The system according to claim 1, wherein the computer unit is capable of assessing the size and/or shape of the biological particles in the liquid analyte material.

20. The system according to claim 1, wherein the computer unit is capable of assessing is the presence or non-presence of a particular type of particles in the liquid analyte material.

21. The system according to claim 1, wherein the duration of the exposure is in the range from 100 milliseconds to 5 seconds.

22. The system according to claim 1, wherein the exposure is performed as a single exposure.

23. The system according to claim 1, where said array of detection elements is one or several of the following types: full frame CCD, frame transfer CCD, interline transfer CCD, line scan CCD, and CMOS image sensor.

24. The system according to claim 1, where the lens has the effect of substantially increasing the intensity of said electromagnetic radiation in or at said sample.

25. The system according to claim 1, further comprising a container for one or more chemical components, the container being connected to a flow system where the sample flows, at least a portion of the sample flowing through the chemical container and thus allowing the mixing of the chemical components with the sample.

26. The system according to claim 1, wherein at least one monochromatic device is selected from interference filters, colored filters, an optical grating, a prism, and optionally active crystals.

27. The system according to claim 1, wherein the sample compartment is a removable sample compartment, which can be readily removed from the system.

28. The system according to claim 1, wherein the sample compartment comprises one or more compartments, where chemical or physical components can be stored such that the chemical or physical components can be added to any sample present in the sample compartment one at a time or more than one at a time.

29. The system according to claim 1, comprising at least 2 of the following: interference filters, colored filters, an optical grating, a prism, and optically active crystals.

30. The system according to claim 1, being adapted to keep the sample in the sample compartment at stand still during the exposure.

* * * * *